(12) United States Patent
Wan et al.

(10) Patent No.: US 11,913,008 B2
(45) Date of Patent: *Feb. 27, 2024

(54) VECTOR COMPRISING SORGHUM TERMINATOR AND METHOD OF USE

(71) Applicant: Performance Plants Inc., Kingston (CA)

(72) Inventors: Jiangxin Wan, Bath (CA); Yafan Huang, Bath (CA); Shujun Yang, Kingston (CA); Monika Maria Kuzma, Battersea (CA)

(73) Assignee: Performance Plants, Inc., Kingston (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/048,002

(22) Filed: Oct. 19, 2022

(65) Prior Publication Data
US 2023/0193308 A1 Jun. 22, 2023

Related U.S. Application Data

(63) Continuation of application No. 16/678,306, filed on Nov. 8, 2019, which is a continuation of application No. 16/019,077, filed on Jun. 26, 2018, now Pat. No. 10,508,283, which is a continuation of application No. 15/266,276, filed on Sep. 15, 2016, now Pat. No. 10,036,035, which is a continuation of application No. 12/483,660, filed on Jun. 12, 2009, now Pat. No. 9,453,238.

(60) Provisional application No. 61/132,067, filed on Jun. 13, 2008.

(51) Int. Cl.
*C12N 15/82* (2006.01)
*C12N 9/12* (2006.01)

(52) U.S. Cl.
CPC ....... *C12N 15/8273* (2013.01); *C12N 9/1205* (2013.01); *C12N 15/8218* (2013.01); *C12N 15/8227* (2013.01); *C12N 15/8261* (2013.01); *C12N 15/8271* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 5,240,842 A | 8/1993 | Mets | |
| 5,349,124 A | 9/1994 | Fischhoff et al. | |
| 5,683,439 A | 11/1997 | Jensen | |
| 5,985,456 A | 11/1999 | Zhou et al. | |
| 6,809,232 B1 | 10/2004 | Held et al. | |
| 8,420,797 B2 | 4/2013 | Abbitt | |
| 9,115,368 B2 | 8/2015 | Abad et al. | |
| 9,453,238 B2 | 9/2016 | Wan et al. | |
| 10,036,035 B2 | 7/2018 | Wan et al. | |
| 11,220,696 B2 * | 1/2022 | Wan | C12N 15/8271 |
| 11,453,889 B2 * | 9/2022 | Wan | C12N 15/8261 |
| 2004/0034888 A1 * | 2/2004 | Liu | C07H 21/04 536/23.6 |
| 2006/0075522 A1 | 4/2006 | Cleveland et al. | |
| 2006/0150283 A1 | 7/2006 | Alexandrov et al. | |
| 2006/0162024 A1 | 7/2006 | Beetham et al. | |
| 2007/0214517 A1 | 9/2007 | Alexandrov et al. | |
| 2012/0023627 A1 | 1/2012 | Gampala et al. | |
| 2018/0312862 A1 | 11/2018 | Wan et al. | |
| 2020/0149059 A1 | 5/2020 | Wan et al. | |
| 2021/0348185 A1 | 11/2021 | Wan et al. | |
| 2022/0090116 A1 | 3/2022 | Wan et al. | |

FOREIGN PATENT DOCUMENTS

| | | |
|---|---|---|
| WO | WO-9630530 A1 | 10/1996 |
| WO | WO-2006063963 A1 | 6/2006 |
| WO | WO-2008027534 A2 | 3/2008 |

OTHER PUBLICATIONS

Alonso et al., "Genome-Wide Insertional Mutagenesis of *Arabidopsis thaliana*," Science, Aug. 1, 2003, vol. 301 No. 5633, pp. 653-657.
An et al., "Functional Analysis of the 3' Control Region of the Potato Wound-Inducible Proteinase Inhibitor II Gene", The Plant Cell, Jan. 1989, 1(1), pp. 115-122.
Araus et al., "Plant Breeding and Drought in C3 Cereals: What Should We Breed For?," Annals of Botany, Jun. 2002, 89(7), pp. 925-940.
Atanassova et al., "A 126 bp Fragment of a Plant Histone Gene Promoter Confers Preferential Expression in Meristems of Transgenic *Arabidopsis*," The Plant Journal, May 1992, 2(3), pp. 291-300.
Baulcombe, D. C., "Gene silencing: RNA makes RNA makes no protein", Current Biology, Aug. 1999, 9(16), pp. R599-R601.
Bedell et al., "Sorghum Genome Sequencing by Methylation Filtration," PLoS Biology, Jan. 2005, vol. 3, Issue 1, e13, 13 pages.
Beetham et al., "A Tool for Functional Plant Genomics: Chimeric RNA/DNA Oligonucleotides Cause in vivo Gene-Specific Mutations," Proceedings of the National Academy of Sciences, Jul. 1999, 96(15), pp. 8774-8778.
Bevan et al., "The Structure and Transcription Start Site of a Major Potato Tuber Protein Gene," Nucleic Acids Research, Jun. 1986, 14(11), pp. 4625-4636.
Bevan et al., "Structure and Transcription of the Nopaline Synthase Gene Region of T-DNA," Nucleic Acids Research, Jan. 1983, 11(2), pp. 369-385.

(Continued)

*Primary Examiner* — Jason Deveau Rosen
(74) *Attorney, Agent, or Firm* — COOLEY LLP; Cynthia A. Kozakiewicz; Jessica D. Cande

(57) ABSTRACT

The invention relates to methods of producing a desired phenotype in a plant by manipulation of gene expression within the plant. The method relates to means which inhibit the level of PK220 gene expression or activity, wherein a desired phenotype such as increased water use efficiency relative to a wild type control plant. The invention also relates to nucleic acid sequences and constructs useful such methods and methods of generating and isolating plants having decreased PK220 expression or activity.

11 Claims, No Drawings

Specification includes a Sequence Listing.

(56) References Cited

OTHER PUBLICATIONS

Cheong et al., "Two calcineurin B-like calcium sensors, interacting with protein kinase CIPK23, regulate leaf transpiration and root potassium uptake in *Arabidopsis*," The Plant Journal, Oct. 2007, 52(2), pp. 223-239.
Christensen et al., "Maize Polyubiquitin Genes: Structure, Thermal Perturbation of Expression and Transcript Splicing, and Promoter Activity Following Transfer to Protoplasts by Electroporation," Plant Molecular Biology, Feb. 1992, 18(4), pp. 675-689.
Condon et al., "Improving Intrinsic Water-Use Efficiency and Crop Yield," Crop Science, Jan. 2002, 42(1), pp. 122-131.
Datla et al., "Modified Binary Plant Transformation Vectors with the Wild-Type Gene Encoding NPTII", Gene, Dec. 1992, 122(2), pp. 383-384.
Davies et al., "Stomatal Control by Chemical Signalling and the Exploitation of this Mechanism to Increase Water Use Efficiency in Agriculture," New Phytologist, Mar. 2002, 153(3), pp. 449-460.
De Freitas et al., "Structural characterization and promoter activity analysis of the y-kafirin gene from sorghum," Mol Gen Genet, Mar. 1994, 245:177-186.
De Loose et al., "The Extensin Signal Peptide Allows Secretion of a Heterologous Protein from Protoplasts," Gene, Mar. 1991, 99(1), pp. 95-100.
Dong et al., "Oligonucleotide-Directed Gene Repair in Wheat Using a Transient Plasmid Gene Repair Assay System," Plant Cell Reports, May 2006, 25(5), pp. 457-465.
Dratewka-Kos et al., "Polypeptide Structure of Germin as Deduced from cDNA Sequencing," Journal of Biological Chemistry, Mar. 1989, 264(9), pp. 4896-4900.
Elomaa et al., "A bHLH transcription factor mediates organ, region and flower type specific signals on dihydroflavonol-4-reductase (dfr) gene expression in the inflorescence of Gerbera hybrida (*Asteraceae*)," The Plant Journal, Oct. 1998, 16(1), pp. 93-99.
Farquhar et al., "Photosynthesis and Carbon Assimilation," Physiology and Determination of Crop Yield, Madison, Oct. 1994, pp. 187-210.
Fraley et al., "Expression of bacterial genes in plant cells," Proceedings of the National Academy of Sciences, Aug. 1983, 80(15), pp. 4803-4807.
Goldberg, R. B., "Regulation of plant gene expression," Philosophical Transactions of the Royal Society of London, B, Biological Sciences, Nov. 1986, B314(1166), pp. 343-353.
Greene et al., "Spectrum of Chemically Induced Mutations from a Large-Scale Reverse-Genetic Screen in *Arabidopsis*," Genetics, Jun. 2003, 164(2), pp. 731-740.
Gruber et al., "Vectors for Plant Transformation," Methods in Plant Molecular Biology and Biotechnology, Boca Raton, FL, CRC Press, Inc., 1993, pp. 89-119.
Hardie, D.G., "Plant Protein Serine/Threonine Kinases: Classification and Functions," Annual Review of Plant Physiol., Plant Molecular Biology, Jun. 1999, 50(1), pp. 97-131.
Horsch et al., "A Simple and General Method for Transferring Genes into Plants," Science, Mar. 1985, 227(4691), pp. 1229-1231.
Huang et al., "ATMPK4, an *Arabidopsis* Homolog of Mitogen-Activated Protein Kinase, is Activated in vitro by ArMEK1 Through Threonine Phosphorylation," Plant Physiology, Apr. 2000, 122(4), pp. 1301-1310.
Kado, C.I. "Molecular Mechanisms of Crown Gall Tumorigenesis," Critical Reviews in Plant Sciences, Jan. 1991, 10(1), pp. 1-32.
Karaba et al., "Improvement of Water Use Efficiency in Rice by Expression of HARDY, an *Arabidopsis* Drought and Salt Tolerance Gene," Proceedings of the National Academy of Sciences, Sep. 2007, 104(39), pp. 15270-15275.
Keil et al., "Primary structure of a proteinase inhibitor II gene from potato (*Solanum tuberosum*)," Nucleic Acids Research, Jul. 1986, 14(14), pp. 5641-5650.

Kennerdell et al., "Heritable gene silencing in *Drosophila* using double-stranded RNA," Nature Biotechnology, Aug. 2000, 18(8), pp. 896-898.
Klein et al., "Transformation of Microbes, Plants and Animals by Particle Bombardment," Bio/technology, Mar. 1992, 10(3), pp. 286-291.
Koh et al., "T-DNA tagged knockout mutation of rice OsGSK1, an orthologue of *Arabidopsis* BIN2, with enhanced tolerance to various abiotic stresses," Plant Molecular Biology, Nov. 2007, 65(4), pp. 453-466.
Last et al., "pEmu: an improved promoter for gene expression in cereal cells," Theoretical and Applied Genetics, May 1991, 81(5), pp. 581-588.
Lepetit et al., "A plant histone gene promoter can direct both replication-dependent and -independent gene expression in transgenic plants," Molecular and General Genetics MGG, Jan. 1992, 231(2), pp. 276-285.
Lund et al., "A plant signal sequence enhances the secretion of bacterial ChiA in transgenic tobacco," Plant Molecular Biology, Jan. 1992, 18(1), pp. 47-53.
Martin et al., "Restriction Fragment Length Polymorphisms Associated with Water Use Efficiency in Tomato," Science, Mar. 1989, 243(4899), pp. 1725-1728.
Masle et al., "The ERECTA Gene Regulates Plant Transpiration Efficiency in *Arabidopsis*," Nature, Aug. 2005, 436(7052), pp. 866-870.
Matsuoka et al., "Propeptide of a precursor to a plant vacuolar protein required for vacuolar targeting," Proceedings of the National Academy of Sciences, Feb. 1991, 88(3), pp. 834-838.
McElroy et al., "Isolation of an Efficient Actin Promoter for Use in Rice Transformation," The Plant Cell, Feb. 1990, 2(2), pp. 163-171.
Mian et al., "Molecular Markers Associated with Water Use Efficiency and Leaf Ash in Soybean," Crop Science, Sep. 1996, 36(5), pp. 1252-1257.
Mittler, R. et al. (2006) "Gain- and loss-of-function mutations in Zat10 enhance the tolerance of plants to abiotic stress," FEBS Letters, Dec. 2006, 580(28-29), pp. 6537-6542.
Mogen et al., "Upstream sequences other than AAUAAA are required for efficient messenger RNA 3'-end formation in plants," The Plant Cell, Dec. 1990, 2(12), pp. 1261-1272.
Moloney et al., "High efficiency transformation of *Brassica napus* using Agrobacterium vectors," Plant Cell Reports, Apr. 1989, 8(4), pp. 238-242.
Morillo, S.A., et al., "Functional Analysis of Receptor-like Kinases in Monocots and Dicots," Current Opinion in Plant Biology, Oct. 2006, vol. 9 (5), pp. 460-469.
Mutisya, J. et al., "Transcriptional regulation of the sbeIIb genes in sorghum (*Sorghum bicolor*) and barley (*Hordeum vulgare*): Importance of the barley sbeIIb second intron," Journal of Plant Physiology, May 2006, 163(7):770-780.
NCBI EST Accession No. CX709060.1, Jan. 21, 2005.
NCBI EST Accession No. Os05g0319700, Jun. 8, 2010.
Needleman and Wunsch, "A General method applicable to the search for similarities in the Amino Acid Sequence of two proteins," Journal of Molecular Biology, Mar. 1970, 48(3), pp. 443-453.
Odell et al., "Identification of DNA sequences required for activity of the cauliflower mosaic virus 35S promoter", Nature, 313:810-812 (1985).
Oleykowski et al., "Mutation Detection Using a Novel Plant Endonuclease", Nucleic Acids Research, Oct. 1988, 26(20):4597-4602.
Price et al., "Linking Drought-Resistance Mechanisms to Drought Avoidance in Upland Rice Using a QTL Approach: Progress and New Opportunities to Integrate Stomatal and Mesophyll Responses," Journal of Experimental Botany, May 2002, 53:989-1004.
Saijo et al., "Over-expression of a single Ca2+-dependent protein kinase confers both cold and salt/drought tolerance on rice plants," The Plant Journal, Aug. 2000, 23(3):319-327.
Sanford et al., "Optimizing the Biolistic Process for Different Biological Applications," Methods Enzymology, Jan. 1993, 17:483-509.
Schwab et al., "Highly Specific Gene Silencing by Artificial MicroRNAs in *Arabidopsis*," The Plant Cell, May 2006, 18:1121-1133.

(56) References Cited

OTHER PUBLICATIONS

Shiu et al., "Receptor-Like Kinases from *Arabidopsis* Form a Monophyletic Gene Family Related to Animal Receptor Kinases," Proceedings of the National Academy of Sciences, Sep. 2001, 98(19):10763-10768.

Stockinger et al., "A Linkage Map of Sweet Cherry Based on RAPD Analysis of a Microspore-Derived Callus Culture Population," Journal of the Heredity, May 1996, 87:214-218.

TAIR Accession No. At2g25220, Nov. 17, 2010.
TAIR Accession No. At2g44790, May 2, 2003.
TAIR Accession No. At4g32000, Nov. 17, 2010.
TAIR Accession No. At5g11020, May 2, 2003.
TAIR Accession No. TC366835, Jun. 27, 2011.
TAIR Accession No. TC372789, Jun. 27, 2011.
TAIR Germplasm/Stock SALK_147838, release date Aug. 15, 2003., 2 pages.

Thomas, C. L. et al., "Size constraints for targeting post-transcriptional gene silencing and for RNA-directed methylation in Nicotiana benthamiana using a potato virus X vector", Plant J.; 25(4):417-25. (Feb. 2001).

Thumma et al., "Identification of Casual Relationship Among Traits Related to Drought Resistance in Stylosanthes scabra Using QTL Analysis", J. Exp. Botany, 52:203-214 (2001).

TIGR Accession No. CO439063, Jun. 8, 2005.

Torii et al., "The *Arabidopsis* ERECTA Gene Encodes a Putative Receptor Protein Kinase with Extracellular Leucine-Rich Repeats", Plant Cell., 8(4):735-746 (1996).

Tran et al., "Functional anaylsis of AHK1/ATHK1 and cytokinin receptor histidine kinases in response to abscisic acid, drought, and salt stress in *Arabidopsis*", Proc. Natl. Acad. Sci. U.S.A., 104(51):20623-20628 (2007).

Umezawa et al. "Engineering drought tolerance in plants: discovering and tailoring genes to unlock the future." Current Opinion In Biotechnology. 17.2(2006): 113-122.

Van der Meer et al., "Promoter analysis of the chalcone synthase (chsA) gene of Petunia hybrida: a 67 bp promoter region directs flower-specific expression", Plant Mol. Biol., 15(1):95-109 (1990).

Velten et al., "Isolation of a dual plant promoter fragment from the Ti plasmid of Agrobacterium tumefaciens", EMBO J., 3(12):2723-2730 (1984).

Verwoert et al., "Developmental specific expression and organelle targeting of the *Escherichia coli* fabD gene, encoding malonyl coenzyme A-acyl carrier protein transacylase in transgenic rape and tobacco seeds", Plant Mol. Biol., 26:189-202, (1994).

Visser et al., "Expression of a chimaeric granule-bound starch synthase-GUS gene in transgenic potato plants", Plant Mol. Biol., 17:691-699 (1991).

Walling et al., "Isolation, characterization and evolutionary relatedness of three members from the soybean multigene family encoding chlorophyll a/b binding proteins", Nucl. Acids Res., 16(22):10477-10492 (1988).

Whisstock et al., "Prediction of protein function from protein sequence and structure," Quarterly Reviews of Biophysics, Aug. 2003, 36(3), pp. 307-340.

Wilkins et al., "Role of Propeptide Glycan in Post-Translational Processing and Transport of Barley Lectin to Vacuoles in Transgenic Tobacco", Plant Cell, 2:301-313 (1990).

Yang et al., "Narrowing Down the Targets: Towards Successful Genetic Engineering of Drought-Tolerant Crops," Molecular Plant, May 2010, 3(3), pp. 469-490.

Yang et al., "Purification, Cloning, and Characterization of the CEL I Nuclease", Biochemistry, 39(13):3533-3541 (2000).

Yang et al. "Ribozyme-mediated high resistance against potato spindle tuber viroid in transgenic potatoes," Proceedings of the National Academy of Sciences, May 1997, 13:94(10), pp. 4861-4865.

Yenofsky et al., "A Mutant Neomyc in Phosphotransferase II Gene Reduces the Resistance of Transformants to Antibiotic Selection Pressure", Proc. Natl. Acad. Sci. USA, 87:3435-3439 (1990).

\* cited by examiner

SEQUENCE LISTING

```
Sequence total quantity: 200
SEQ ID NO: 1         moltype = DNA  length = 1299
FEATURE              Location/Qualifiers
source               1..1299
                     mol_type = genomic DNA
```

```
                    organism = Arabidopsis thaliana
SEQUENCE: 1
atgagagagc ttcttcttct tcttcttctt cattttcagt ctctaattct tttgatgatc    60
ttcatcactg tctctgcttc ttctgcttca aatccttctt tagctcctgt ttactcttcc   120
atggctacat tctctcctcg aatccaaatg ggaagtggtg aagaagatag atttgatgct   180
cataagaaac ttctgattgg tctcataatc agtttctctt ctcttggcct tataatcttg   240
ttctgttttg gcttttgggt ttatcgcaag aaccaatctc caaatccat caacaactca    300
gattctgaga gtgggaattc attttccttg ttaatgagac gacttggctc gattaaaact   360
cagagaagaa cttctatcca aaagggttac gtgcaatttt tcgatatcaa gaccctcgag   420
aaagcgacag gcggttttaa agaaagtagt gtaatcggac aaggcggttt cggatgcgtt   480
tacaagggtt gtttggacaa taacgttaaa gcagcggtca agaagatcga gaacgttagc   540
caagaagcaa aacgagaatt tcagaatgaa gttgacttgt tgagcaagat ccatcactcg   600
aacgttatat cattgttggg ctctgcaagc gaaatcaact cgagtttcat cgtttatgag   660
cttatggaga aaggatcatt agatgaacag ttacatgggc cttctcgtgg atcagctcta   720
acatggcaca tgcgtatgaa gattgctctt gatacagcta gaggactaga gtatctccat   780
gagcattgtc gtccaccagt tatccacaga gatttgaaat cttcgaatat tcttcttgat   840
tcttccttca acgccaagat ttcagatttc ggtcttgctg tatcgctgga tgaacatggc   900
aagaacaaca ttaaactctc tgggacactt ggttatgttg ccccggaata cctccttgac   960
ggaaaactga cggataagag tgatgtttat gcatttgggg tagttctgct gaactcttg  1020
ttgggtagac gaccagttga aaaattaact ccagctcaat gccaatctct tgtaacttgg  1080
gcaatgccac aacttaccga tagatccaag cttccaaaca ttgtggatgc cgttataaaa  1140
gatacaatgg atctcaaaca cttataccag gtagcagcca tggctgtgtt gtgcgtgcag  1200
ccagaaccaa gttaccggcc gttgataacc gatgttcttc actcacttgt tccactggtt  1260
ccggtagagc taggagggac tctccggtta acaagatga                         1299

SEQ ID NO: 2              moltype = AA    length = 432
FEATURE                   Location/Qualifiers
source                    1..432
                          mol_type = protein
                          organism = Arabidopsis thaliana
SEQUENCE: 2
MRELLLLLLL HFQSLILLMI FITVSASSAS NPSLAPVYSS MATFSPRIQM GSGEEDRFDA    60
HKKLLIGLII SFSSLGLIIL FCFGFWVYRK NQSPKSINNS DSESGNSFSL LMRRLGSIKT   120
QRRTSIQKGY VQFFDIKTLE KATGGFKESS VIGQGGFGCV YKGCLDNNVK AAVKKIENVS   180
QEAKREFQNE VDLLSKIHHS NVISLLGSAS EINSSFIVYE LMEKGSLDEQ LHGPSRGSAL   240
TWHMRMKIAL DTARGLEYLH EHCRPPVIHR DLKSSNILLD SSFNAKISDF GLAVSLDEHG   300
KNNIKLSGTL GYVAPEYLLD GKLTDKSDVY AFGVVLLELL LGRRPVEKLT PAQCQSLVTW   360
AMPQLTDRSK LPNIVDAVIK DTMDLKHLYQ VAAMAVLCVQ PEPSYRPLIT DVLHSLVPLV   420
PVELGGTLRL TR                                                      432

SEQ ID NO: 3              moltype = DNA    length = 1299
FEATURE                   Location/Qualifiers
source                    1..1299
                          mol_type = genomic DNA
                          organism = Arabidopsis thaliana
SEQUENCE: 3
atgagagagc ttcttcttct tcttcttctt cattttcagt ctctaattct tttgatgatc    60
ttcatcactg tctctgcttc ttctgcttca aatccttctt tagctcctgt ttactcttcc   120
atggctacat tctctcctcg aatccaaatg ggaagtggtg aagaagatag atttgatgct   180
cataagaaac ttctgattgg tctcataatc agtttctctt ctcttggcct tataatcttg   240
ttctgttttg gcttttgggt ttatcgcaag aaccaatctc caaatccat caacaactca    300
gattctgaga gtgggaattc attttccttg ttaatgagac gacttggctc gattaaaact   360
cagagaagaa cttctatcca aaagggttac gtgcaatttt tcgatatcaa gaccctcgag   420
aaagcgacag gcggttttaa agaaagtagt gtaatcggac aaggcggttt cggatgcgtt   480
tacaagggtt gtttggacaa taacgttaaa gcagcggtca agaagatcga gaacgttagc   540
caagaagcaa aacgagaatt tcagaatgaa gttgacttgt tgagcaagat ccatcactcg   600
aacgttatat cattgttggg ctctgcaagc gaaatcaact cgagtttcat cgtttatgag   660
cttatggaga aaggatcatt agatgaacag ttacatgggc cttctcgtgg atcagctcta   720
acatggcaca tgcgtatgaa gattgctctt gatacagcta gaggactaga gtatctccat   780
gagcattgtc gtccaccagt tatccacaga gatttgaaat cttcgaatat tcttcttgat   840
tcttccttca acgccaagat ttcagatttc ggttttgctg tatcgctgga tgaacatggc   900
aagaacaaca ttaaactctc tgggacactt ggttatgttg ccccggaata cctccttgac   960
ggaaaactga cggataagag tgatgtttat gcatttgggg tagttctgct gaactcttg  1020
ttgggtagac gaccagttga aaaattaact ccagctcaat gccaatctct tgtaacttgg  1080
gcaatgccac aacttaccga tagatccaag cttccaaaca ttgtggatgc cgttataaaa  1140
gatacaatgg atctcaaaca cttataccag gtagcagcca tggctgtgtt gtgcgtgcag  1200
ccagaaccaa gttaccggcc gttgataacc gatgttcttc actcacttgt tccactggtt  1260
ccggtagagc taggagggac tctccggtta acaagatga                         1299

SEQ ID NO: 4              moltype = AA    length = 432
FEATURE                   Location/Qualifiers
source                    1..432
                          mol_type = protein
                          organism = Arabidopsis thaliana
SEQUENCE: 4
MRELLLLLLL HFQSLILLMI FITVSASSAS NPSLAPVYSS MATFSPRIQM GSGEEDRFDA    60
HKKLLIGLII SFSSLGLIIL FCFGFWVYRK NQSPKSINNS DSESGNSFSL LMRRLGSIKT   120
QRRTSIQKGY VQFFDIKTLE KATGGFKESS VIGQGGFGCV YKGCLDNNVK AAVKKIENVS   180
QEAKREFQNE VDLLSKIHHS NVISLLGSAS EINSSFIVYE LMEKGSLDEQ LHGPSRGSAL   240
```

```
TWHMRMKIAL DTARGLEYLH EHCRPPVIHR DLKSSNILLD SSFNAKISDF GFAVSLDEHG   300
KNNIKLSGTL GYVAPEYLLD GKLTDKSDVY AFGVVLLELL LGRRPVEKLT PAQCQSLVTW   360
AMPQLTDRSK LPNIVDAVIK DTMDLKHLYQ VAAMAVLCVQ PEPSYRPLIT DVLHSLVPLV   420
PVELGGTLRL TR                                                      432

SEQ ID NO: 5           moltype = DNA  length = 1160
FEATURE                Location/Qualifiers
source                 1..1160
                       mol_type = genomic DNA
                       organism = Arabidopsis thaliana
SEQUENCE: 5
atgggaagtg gtgaagaaga tagatttgat gctcataaga aacttctgat tggtctcata    60
atcagtttct cttctcttgg ccttataatc ttgttctgtt ttggcttttg ggtttatcgc   120
aagaaccaat ctccaaaatc catcaacaac tcagattctg agagtgggaa ttcatttttcc  180
ttgttaatga gacgacttgg ctcgattaaa actcagagaa gaacttctat ccaaaagggt   240
tacgtgcaat ttttcgatat caagaccctc gagaaagcga caggcggttt taagaaagt   300
agtgtaatcg gacaaggcgg tttcggatgc gtttacaagg gttgtttgga cataacgtt   360
aaagcaagat tcaagaagat cgagaacgtt agccaagaag caaaacgaca atttcagaat   420
gaagttgact tgttgagcaa gatccatcac tcgaacgtta tatcattgtt gggctctgca   480
agcgaaatca actcgagttt catcgtttat gagcttatgg agaaaggatc attagatgaa   540
cagttacatg ggccttctcg tggatcagct ctaacatggc acatgcgtat gaagattgct   600
cttgatacag ctagaggact agagtatctc catgagcatt gtcgtccacc agttatccac   660
agagatttga atcttcgaa tattcttctt gattcttcct tcaacgccaa gatttcagat   720
ttcggtttg ctgtatcgct ggatgaacat ggcaagaaca acattaaact ctctgggaca   780
cttggttatg ttgccccgga atacctcctt gacgaaaaac tgacggataa gagtgatgtt   840
tatgcatttg gggtagttct gcttgaactc ttgttgggta gacgaccagt tgaaaaatta   900
actccagctc aatgccaatc tcttgtaact tgggcaatgc cacaacttac cgatagatcc   960
aagcttccaa acattgtgga tgccgttata aaagatacaa tggatctcaa acacttatac  1020
caggtagcag ccatggctgt gttgtgcgtg cagccagaaa caagttaccg gccgttgata  1080
accgatgttc tcactcact tgttccactg gttccggtag agctaggagg gactctccgg  1140
ttaacaagat gattcacaga                                             1160

SEQ ID NO: 6           moltype = AA  length = 383
FEATURE                Location/Qualifiers
source                 1..383
                       mol_type = protein
                       organism = Arabidopsis thaliana
SEQUENCE: 6
MGSGEEDRFD AHKKLLIGLI ISFSSLGLII LFCFGFWVYR KNQSPKSINN SDSESGNSFS    60
LLMRRLGSIK TQRRTSIQKG YVQFFDIKTL EKATGGFKES SVIGQGGFGC VYKGCLDNNV   120
KAAVVKKIENV SQEAKREFQN EVDLLSKIHH SNVISLLGSA SEINSSFIVY ELMEKGSLDE  180
QLHGPSRGSA LTWHMRMKIA LDTARGLEYL HEHCRPPVIH RDLKSSNILL DSSFNAKISD   240
FGFAVSLDEH GKNNIKLSGT LGYVAPEYLL DGKLTDKSDV YAFGVVLLEL LLGRRPVEKL   300
TPAQCQSLVT WAMPQLTDRS KLPNIVDAVI KDTMDLKHLY QVAAMAVLCV QPEPSYRPLI   360
TDVLHSLVPL VPVELGGTLR LTR                                          383

SEQ ID NO: 7           moltype = DNA  length = 1160
FEATURE                Location/Qualifiers
source                 1..1160
                       mol_type = genomic DNA
                       organism = Arabidopsis thaliana
SEQUENCE: 7
atgggaagtg gtgaagaaga tagatttgat gctcataaga aacttctgat tggtctcata    60
atcagtttct cttctcttgg ccttataatc ttgttctgtt ttggcttttg ggtttatcgc   120
aagaaccaat ctccaaaatc catcaacaac tcagattctg agagtgggaa ttcatttttcc  180
ttgttaatga gacgacttgg ctcgattaaa actcagagaa gaacttctat ccaaaagggt   240
tacgtgcaat ttttcgatat caagaccctc gagaaagcga caggcggttt taagaaagt   300
agtgtaatcg gacaaggcgg tttcggatgc gtttacaagg gttgtttgga cataacgtt   360
aaagcagcgg tcaagaagat cgagaacgtt agccaagaag caaaacgaca atttcagaat   420
gaagttgact tgttgagcaa gatccatcac tcgaacgtta tatcattgtt gggctctgca   480
agcgaaatca actcgagttt catcgtttat gagcttatgg agaaaggatc attagatgaa   540
cagttacatg ggccttctcg tggatcagct ctaacatggc acatgcgtat gaagattgct   600
cttgatacag ctagaggact agagtatctc catgagcatt gtcgtccacc agttatccac   660
agagatttga atcttcgaa tattcttctt gattcttcct tcaacgccaa gatttcagat   720
ttcggtcttg ctgtatcgct ggatgaacat ggcaagaaca acattaaact ctctgggaca   780
cttggttatg ttgccccgga atacctcctt gacggaaaac tgacggataa gagtgatgtt   840
tatgcatttg gggtagttct gcttgaactc ttgttgggta gacgaccagt tgaaaaatta   900
actccagctc aatgccaatc tcttgtaact tgggcaatgc cacaacttac cgatagatcc   960
aagcttccaa acattgtgga tgccgttata aaagatacaa tggatctcaa acacttatac  1020
caggtagcag ccatggctgt gttgtgcgtg cagccagaaa caagttaccg gccgttgata  1080
accgatgttc tcactcact tgttccactg gttccggtag agctaggagg gactctccgg  1140
ttaacaagat gattcacaga                                             1160

SEQ ID NO: 8           moltype = AA  length = 383
FEATURE                Location/Qualifiers
source                 1..383
                       mol_type = protein
                       organism = Arabidopsis thaliana
SEQUENCE: 8
```

```
MGSGEEDRFD AHKKLLIGLI ISFSSLGLII LFCFGFWVYR KNQSPKSINN SDSESGNSFS    60
LLMRRLGSIK TQRRTSIQKG YVQFFDIKTL EKATGGFKES SVIGQGGFGC VYKGCLDNNV   120
KAAVKKIENV SQEAKREFQN EVDLLSKIHH SNVISLLGSA SEINSSFIVY ELMEKGSLDE   180
QLHGPSRGSA LTWHMRMKIA LDTARGLEYL HEHCRPPVIH RDLKSSNILL DSSFNAKISD   240
FGLAVSLDEH GKNNIKLSGT LGYVAPEYLL DGKLTDKSDV YAFGVVLLEL LLGRRPVEKL   300
TPAQCQSLVT WAMPQLTDRS KLPNIVDAVI KDTMDLKHLY QVAAMAVLCV QPEPSYRPLI   360
TDVLHSLVPL VPVELGGTLR LTR                                           383

SEQ ID NO: 9            moltype = DNA   length = 1542
FEATURE                 Location/Qualifiers
source                  1..1542
                        mol_type = genomic DNA
                        organism = Arabidopsis thaliana
SEQUENCE: 9
atcaaaaact tttctttct tagcaaaaaa aacaaaaaaa tgagagagct tcttcttctt     60
cttcttcttc attttcagtc tctaattctt ttgatgatct tcatcactgt ctctgcttct   120
tctgcttcaa atccttcttt agctcctgtt tactcttcca tggctacatt ctctcctcga   180
atccaaatgg gaagtggtga agaagataga tttgatgctc ataagaaact tctgattggt   240
ctcataatca gtttctcttc tcttggcctt ataatcttgt tctgttttgg cttttgggtt   300
tatcgcaaga accaatctcc aaaatccatc aacaactcag attctgagag tgggaattca   360
ttttccttgt taatgagacg acttggctcg attaaaactc agagaagaac ttctatccaa   420
aagggttacg tgcaattttt cgatatcaag accctcgaga aagcgacagg cggttttaaa   480
gaaagtagtg taatcggaca aggcggtttc ggatgcgttt acaaggttgt tttgacaat   540
aacgttaaag cagcggtcaa gaagatcgag aacgttagcc aagaagcaaa acgaaattt   600
cagaatgaag ttgacttgtt gagcaagatc catcactcga acgttatatc attgttgggc   660
tctgcaagcg aaatcaactc gagtttcatc gtttatgagc ttatggagaa aggatcatta   720
gatgaacagt tacatgggcc ttctcgtgga tcagctctaa catggcacat gcgtatgaag   780
attgctcttg atacagctag aggactagag tatctccatg agcattgtcg tccaccagtt   840
atccacagag atttgaaatc ttcgaatatt cttcttgatt cttccttcaa cgccaagatt   900
tcagatttcg gtcttgctgt atcgctggat gaacatgggca agaacaacat taaactcctcg   960
gggacactttg gttatgttgc cccggaatac ctccttgacg gaaaactgac ggataagagt  1020
gatgtttatg catttgggt agttctgctt gaactcttgt tgggtagacg accagttgaa   1080
aaattaactc cagctcaatg ccaatctctt gtaacttggg caatgccaca acttaccgat  1140
agatccaagc ttccaaacat tgtggatgcc gttataaaag atacaatgga tctcaaacac  1200
ttataccagg tagcagccat ggctgtgttg tgcgtgcagc cagaaccaag ttaccggccg  1260
ttgataaccg atgttcttca ctcacttgtt ccactggttc cggtagagct aggagggact  1320
ctccggttaa caagatgatt cacagaaaca cgccaaaaga aatccaaagc catttagatg  1380
atttttcttt atccttgcc tttatatttt tttgtatagg gttatgatcc actcatctga  1440
aagtttgggg gtaagaatgt gagaatataa gttttcaggg ttgttgagtt ctatataatt  1500
atatttgttt ctttttattg tcaaatataa ttatattttt gt                     1542

SEQ ID NO: 10           moltype = DNA   length = 1309
FEATURE                 Location/Qualifiers
source                  1..1309
                        mol_type = genomic DNA
                        organism = Arabidopsis thaliana
SEQUENCE: 10
aaaatgagag agcttcttct tcttcttctt cttcatttc agtctctaat tcttttgatg     60
atcttcatca ctgtctctgc ttcttctgct tcaaatcctt ctttagctcc tgtttactct   120
tccatggcta cattctctcc tcgaatccaa atggggaagtg gtgaagaaga tagatttgat   180
gctcataaga aactttctgat tggtctcata atcagttctc cttctcttgg ccttataatc   240
ttgttctgtt ttggcttttg ggtttatcgc aagaaccaat ctccaaaatc catcaacaac   300
tcagattctg agagtgggaa ttcatttttcc ttgttaatga gacgacttgg ctcgattaaa   360
actcagagaa gaacttctat ccaaaagggt tacgtgcaat ttttcgatat caagaccctc   420
gagaaagcga caggcggttt taaagaaagt agtgtaatcg gacaaggcgg tttcggatgc   480
gtttacaagg gttgtttgga caataacgtt aaagcagcgg tcaagaagat cgagaacgtt   540
agccaagaag caaaacgaga atttcagaat gaagttgact tgttgagcaa gatccatcac   600
tcgaacgtta tcattgtt gggctctgca agcgaaatca actcgagttt catcgtttat    660
gagcttatgg agaaaggatc attagatgaa cagttacatg ggccttctcg tggatcagct   720
ctaacatggc acatgcgtat gaagattgct cttgatacag ctagaggact agagtatctc   780
catgagcatt gtcgtccacc agttatccac agagatttga aatcttcgaa tattcttctt   840
gattcttcct tcaacgccaa gatttcagat ttcggtcttg ctgtatcgct ggatgaacat   900
ggcaagaaca acattaaact ctctgggaca cttggttatg ttgcccccgga atacctcctt   960
gacggaaaac tgacggataa gagtgatgtt tatgcattttg gggtagtct gcttgaactc  1020
ttgttgggta gacgaccagt tgaaaaatta actccagctc aatgccaatc tcttgtaact  1080
tgggcaatgc cacaacttac cgatagatcc aagcttccaa acattgtgga tgccgttata  1140
aaagatacaa tggatctcaa acacttatac caggtagcag ccatggctgt gttgtgcgtg  1200
cagccagaac caagttaccg gccgttgata accgatgttc ttcactcact tgttccactg  1260
gttccggtag agctaggagg gactctccgg ttaacaagat gattcacag                1309

SEQ ID NO: 11           moltype = DNA   length = 1177
FEATURE                 Location/Qualifiers
source                  1..1177
                        mol_type = genomic DNA
                        organism = Arabidopsis thaliana
SEQUENCE: 11
tctgtgtcag gaatccaaat gggaagtggt gaagaagata gatttgatgc tcataagaaa     60
cttctgattg gtctccataat cagtttctct tctcttggcc ttataatctt gttctgttt   120
ggcttttggg tttatcgcaa gaaccaatct ccaaaatcca tcaacaactc agattctgag   180
```

```
agtgggaatt cattttcctt gttaatgaga cgacttggct cgattaaaac tcagagaaga    240
acttctatcc aaaagggtta cgtgcaattt tcgatatca agaccctcga gaaagcgaca    300
ggcggtttta aagaaagtag tgtaatcgga caaggcggtt tcggatgcgt ttacaagggt    360
tgtttggaca ataacgttaa agcagcggtc aagaagatcg agaacgttag ccaagaagca    420
aaacgagaat ttcagaatga agttgacttg ttgagcaaga tccatcactc gaacgttata    480
tcattgttgg gctctgcaag cgaaatcaac tcgagtttca tcgtttatga gcttatggag    540
aaaggatcat tagatgaaca gttacatggg ccttctcgtg gatcagctct aacatggcac    600
atgcgtatga agattgctct tgatacagct agaggactag agtatctcca tgagcattgt    660
cgtccaccag ttatccacag agatttgaaa tcttcgaata ttcttcttga ttcttccttc    720
aacgccaaga tttcagattt cggtcttgct gtatcgctgg atgaacatgg caagaacaac    780
attaaactct ctgggacact tggttatgtt gccccggaat acctccttga cggaaaactg    840
acggataaga gtgatgttta tgcatttggg gtagttctgc ttgaactctt gttgggtaga    900
cgaccagttg aaaaattaac tccagctcaa tgccaatctc ttgtaacttg ggcaatgcca    960
caacttaccg atagatccaa gcttccaaac attgtggatg ccgttataaa agatacaatg   1020
gatctcaaac acttatacca ggtagcagcc atggctgtgt tgtgcgtgca gccagaacca   1080
agttaccggc cgttgataac cgatgttctt cactcacttg ttccactggt tccggtagag   1140
ctaggaggga ctctccggtt aacaagatga ttcacag                           1177

SEQ ID NO: 12            moltype = DNA   length = 154
FEATURE                  Location/Qualifiers
source                   1..154
                         mol_type = genomic DNA
                         organism = Arabidopsis thaliana
SEQUENCE: 12
tcgcaagaac caatctccaa aatccatcaa caactcagat tctgagagtg ggaattcatt     60
ttccttgtta atgagacgac ttggctcgat taaaactcag agaagaactt ctatccaaaa    120
gggttacgtg caatttttcg atatcaagac cctc                               154

SEQ ID NO: 13            moltype = DNA   length = 288
FEATURE                  Location/Qualifiers
source                   1..288
                         mol_type = genomic DNA
                         organism = Arabidopsis thaliana
SEQUENCE: 13
tctgtgtcag gaatccaaat gggaagtggt gaagaagata gatttgatgc tcataagaaa     60
cttctgattg gtctcataat cagtttctct tctcttggcc ttataatctt gttctgtttt    120
ggcttttggg tttatcgcaa gaaccaatct ccaaaatcca tcaacaactc agattctgag    180
agtgggaatt cattttcctt gttaatgaga cgacttggct cgattaaaac tcagagaaga    240
acttctatcc aaaagggtta cgtgcaattt tcgatatca agaccctc                  288

SEQ ID NO: 14            moltype = DNA   length = 1510
FEATURE                  Location/Qualifiers
source                   1..1510
                         mol_type = genomic DNA
                         organism = Arabidopsis thaliana
SEQUENCE: 14
tgttaaaagc gatttataat ttacaccgtt ttggtgtata tttctatcta tccttttaca     60
agacctatat atgttatgtt atggtggtgt actattttaa gtgagcgaca tagtattttc    120
ttcatatagc taattaatca acaacaattt cccaacttac aactatttgc gtactttaaa    180
cttatattga aagagaacta caaaattatt tttttgtaca agagaattat ggtcttcgga    240
tcaataattt ctctagatat aatatgtaaa gccaaccctaa taattgtaa aatccatgat    300
ttgatataat tttctttaa aattgtgaat tggcagacaa aaacaacatt acattttgat    360
ttaaattcat aactttgact tgctaaggaa acaccatgat tcatttttg tcatttgtta    420
catcatcact agaaatattt gatctaactt tattatgata atagactaca tactacatat    480
gcagttacga ttttaaatac tacatattta agcgtgttta aactgtaacc atatcatata    540
aaatgacata tctaaaagtg attttcaata ttttgatatg atatgtgttg tagcacggat    600
aatgatctaa tttttaagta ataagcttgt tcattacaaa agaagaaa gtagtattgg    660
gccatgatta tgtaaggaca aaataggaag atgtggaaga agccattcga gggttttatt    720
acaaaaacag agtatataat tggtcataat gttttattca cttaatttaa cattattgca    780
ttatattttc atgaacacat atttctttaa ctaaaaatat acacatattt cttattgtag    840
atgaagtgaa aagaacaata tttggggttca catctatggg tgaatccttt taatcaccccc    900
ctaaaataaa aaaggtgcca tatttctatt tttagagaaa gatatagagc accattggag    960
tggttttgct ccaaatatag agtttagaga aatatataat acaccattgg agatgctcta   1020
aaatgaattt atttatttat ttagatgaa gattctaatt ggttagaaaaa agaggaagtg   1080
aataatagga ttcacctata agagtgaacc caagtatttt taagagataa tgtgtaaagt   1140
aaatagatg tcattgtgtg aattatgaat agaaccatgg ttttccattt ttaattgctt   1200
aacataggg aatcaacaat ggggttttaat atgtcaatag acaatagtaa agaaagtatt   1260
tgatctatcc caaatctttc ttcgttcgtt agttcatcac tttctttctt tttggttata   1320
ttaatggtag agaactaaaa attcaacttt ttattcaaaa gctccctttc tcttttccctc   1380
ctttatttgc cataaaagtg atttcaagaa gacagcgaga gagaaagtga tagttcgttc   1440
actcttcgct ttctcaagaa tttcaaaaca ccaaaaagt ctttagattg aatttcatca   1500
aaaactttc                                                          1510

SEQ ID NO: 15            moltype = DNA   length = 157
FEATURE                  Location/Qualifiers
source                   1..157
                         mol_type = genomic DNA
                         organism = Arabidopsis thaliana
SEQUENCE: 15
```

```
agacaagaaa aaaggaaaca aaattttatg aaagagatct ccattagaga aagagagagc    60
gagagagaga ttaatcttgg aagagcaatc tcacattctc acactgctct tagaaaatct   120
ctctttcacc attaaaaatc ccaaagagtc tggagaa                            157

SEQ ID NO: 16          moltype = DNA   length = 1257
FEATURE                Location/Qualifiers
source                 1..1257
                       mol_type = genomic DNA
                       organism = Arabidopsis thaliana
SEQUENCE: 16
atgggaaaga ttcttcatct tcttcttctt cttcttaagg tctctgttct tgaattcatc    60
attagtgttt ctgcttttac ttcacctgct tcacagcctt ctctttctcc tgtttacact   120
tccatggctt ccttttctcc agggatccac atgggcaaag gccaagaaca caagtctgat   180
gcacacaaga aacttctaat cgctctcata atcacctcat cttctctagg actaatactt   240
gtatcttgtt tatgcttttg ggtttattgg tctaagaaat ctcccaaaaa caccaagaac   300
tcaggtgaga gtaggatttc attatccaag aagggctttg tgcagtccct cgattacaag   360
acactagaga agcaacagg cggtttcaaa acggtaatc ttataggacg aggcgggttc    420
ggagatgttt acaaggcctg tttaggcaac aacactctag cagcagtcaa aaagatcgaa   480
aacgttagtc aagaagcaaa acgagaattt cagaatgaag ttgatttgtt gagcaagatt   540
caccacccga acatcatctc attgtttgga tatggaaatg aactcagttc gagttttatc   600
gtctacgagc tgatggaaag cggatcattg gatacacagt tacacggacc ttctcgggga   660
tcggcttaa catggcacat gcggatgaag attgctcttg atacagcaaa agctgttgag   720
tatctccacg agcgttgtcg tcctccggtt atccacagag atcttaaatc gtcaaatatt   780
ctccttgatt cttccttcaa cgccaagatt tcggattttg gtcttgcggt aatggtgggg   840
gctcacggca aaaacaacat taaactatca ggaacacttg ttatgttgc tccagaatat    900
ctcctagatg gaaaattgac ggataagagt gatgtttatg cgtttggtgt ggttttactt   960
gaactcttgt taggaagacg gccggttgag aaattgagtt cggttcagtg tcaatctctt  1020
gtcacttggg caatgcccca acttacggat agatcaaagc ttccgaaaat cgtggatccg  1080
gttatcaaaa atacaatgga tcataagcac ttataccagg tggcagccgt ggcagtgctt  1140
tgtgtacaac cagaaccgag ttatcgaccg ttgataaccg atgttcttca ctcactagtt  1200
ccattggttc cggtagagct aggagggact ctccggttaa taccatcatc gtcttga     1257

SEQ ID NO: 17          moltype = AA   length = 418
FEATURE                Location/Qualifiers
source                 1..418
                       mol_type = protein
                       organism = Arabidopsis thaliana
SEQUENCE: 17
MGKILHLLLL LLKVSVLEFI ISVSAFTSPA SQPSLSPVYT SMASFSPGIH MGKGQEHKLD    60
AHKKLLIALI ITSSSLGLIL VSCLCFWVYW SKKSPKNTKN SGESRISLSK KGFVQSFDYK   120
TLEKATGGFK DGNLIGRGGF GDVYKACLGN NTLAAVKKIE NVSQEAKREF QNEVDLLSKI   180
HHPNIISLFG YGNELSSSFI VYELMESGSL DTQLHGPSRG SALTWHMRMK IALDTARAVE   240
YLHERCRPPV IHRDLKSSNI LLDSSFNAKI SDFGLAVMVG AHGKNNIKLS GTLGYVAPEY   300
LLDGKLTDKS DVYAFGVVLL ELLLGRRPVE KLSSVQCQSL VTWAMPQLTD RSKLPKIVDP   360
VIKDTMDHKH LYQVAAVAVL CVQPEPSYRP LITDVLHSLV PLVPVELGGT LRLIPSSS    418

SEQ ID NO: 18          moltype = DNA   length = 1302
FEATURE                Location/Qualifiers
source                 1..1302
                       mol_type = genomic DNA
                       organism = Arabidopsis thaliana
SEQUENCE: 18
atgaagcaaa ttgttataac agctcttgtt ttactacaag cttatgttct tcatcaatcc    60
acatgtgtta tgtcccttac tacacaagaa tctccttctc ctcaaccttc tgctttcact   120
cccgccttat ctcctgatta tcaacagaga gagaaggaat tgcataaaca agagagtaac   180
aacatgagac tggttatttc actagcagct acattttcct tagttggtat aatcttactt   240
tgctctctgc tttattggtt tgccataggg agaagaaacc tcaagagctc aggttgtggg   300
tgtagtggaa tcacattctt gaatcggttt agtcgctcaa aaacattaga caagagaact   360
acaaagcagg gaacagtgtc attgatcgat tacaatatac gaagaaggg aactagtggt   420
ttcaaggaga gtaacatttt gggtcaaggt ggatttggat gtgtatattc tgccacatta   480
gagaacaaca tttcagctgc ggttaagaag ctagactgtg ccaatgaaga tgcagcaaag   540
gaatttaaga gtgaggttga gatattgagt aagctccagc accgaatat aatatcccctt   600
ttgggttata gcacgaatga tactgcgaga ttcattgtct atgagctgat gccaaacgtt   660
tctctggaat ctcatttaca cggatcttct caggggttcgg catcacatg gcctatgagg   720
atgaagattg ctcttgatgt aacaagggga ttagaatatt tgcatgaaca ttgtcatcca   780
gcaatcattc acagggactt gaaatcatcc aacatcttat tagatagcaa tttcaatgct   840
aagatttcag attttggtct agctgttgtt gatgggccaa gaacaagaa ccataaactt    900
tccgggacag ttggctacgt tgcaccagag tatcttctca acggcccaatt gacagaaaag   960
agcgacgtgt atgcttttgg agtagtgtta ttagagctta ctcgggaa aaaacctggg    1020
gagaaactag ctcccggtga atgccaatcc atcatcactt gggcaatgcc ttatctcact   1080
gatagaacca gttaccaag cgtcatagat cctgcgatta agatacgat ggacttgaaa    1140
cacctttacc aggtagcggc agtggcgatt tgtgcgtgc agcagaacc gagttataga    1200
ccgttgatta cagacgtctt gcattctctt ataccttttg ttccaatgga acttggtgga  1260
accttaaaaa ccatcaaatg tgcttcaatg gatcactgtt aa                     1302

SEQ ID NO: 19          moltype = AA   length = 433
FEATURE                Location/Qualifiers
source                 1..433
                       mol_type = protein
```

```
                          organism = Arabidopsis thaliana
SEQUENCE: 19
MKQIVITALV LLQAYVLHQS TCVMSLTTQE SPSPQPSAFT PALSPDYQQR EKELHKQESN    60
NMRLVISLAA TFSLVGIILL CSLLYWFCHR RRNLKSSGCG CSGITFLNRF SRSKTLDKRT   120
TKQGTVSLID YNILEEGTSG FKESNILGQG GFGCVYSATL ENNISAAVKK LDCANEDAAK   180
EFKSEVEILS KLQHPNIISL LGYSTNDTAR FIVYELMPNV SLESHLHGSS QGSAITWPMR   240
MKIALDVTRG LEYLHEHCHP AIIHRDLKSS NILLDSNFNA KISDFGLAVV DGPKNKNHKL   300
SGTVGYVAPE YLLNGQLTEK SDVYAFGVVL LELLLGKKPV EKLAPGECQS IITWAMPYLT   360
DRTKLPSVID PAIKDTMDLK HLYQVAAVAI LCVQPEPSYR PLITDVLHSL IPLVPMELGG   420
TLKTIKCASM DHC                                                     433

SEQ ID NO: 20            moltype = DNA   length = 2016
FEATURE                  Location/Qualifiers
source                   1..2016
                         mol_type = genomic DNA
                         organism = Arabidopsis thaliana
SEQUENCE: 20
atgaagacta tgtccaaatc gtctttgcgt ttgcattttc tctcgctact cttactttgt    60
tgtgtctccc cttcaagctt tgtcattata agattcatta cacataatca ttttgatggt   120
ctagtacgtt gtcatcccca caagtttcaa gcccttacgc agttcaagaa cgagttgat    180
acccgccgtt gcaaccacag taactacttt aatggaatct ggtgtgataa ctccaaggtg   240
cggtcacaaa gctacgaaca cgggactgtc tcagtgcaac tctcaaatca aacagtagcc   300
tcttccagtt tcatcatctt cgctaccttg atctctctca caacaacttc acctcctctt   360
ccctcccttc cgagtttgtt tcccactttg cggaatctaa ccaagctcac agttttagac   420
cttttctcata atcacttctc cggaactttg aagcccaaca atagcctctt tgagttacac   480
caccttcgtt acctctaatct cgaggtcaac aacttcagtt cctcactcct ttccgagttt   540
ggctatctca acaattaca gcactgtggc ctcaaagagt tcccaaacat attcaagacc   600
cttaaaaaaa tggaggctat agacgtatcc aacaatagaa tcaacgggaa aatccctgag   660
tggttatgga gccttcctct tcttcattta gtgaatattt aataattc ttttgacggt   720
ttcgaaggat caacgaagt tttagtaaat tcatcggttc ggatattact ttggagtca   780
aacaactttg aaggagcact tcctagtcta ccacactcta tcaacgcctt ctccgcgggt   840
cataacaatt tcactggaga gatacctctt tcaatctgca ccagaacctc acttggtgtc   900
cttgatctaa actacaacaa cctcattggt ccggtttctc aatgtttgag taatgtcacg   960
tttgtaaatc tccggaaaaa caatttggaa ggaactcttc ctgagacttt cattgtcggt  1020
tcctcgataa ggacacttga tgttggatac aatcgactaa cgggaaagct tccaaggtct  1080
cttttgaact gctcatctct agagtttcta agcgttgaca caacagaat caaagacaca  1140
tttcctttct ggctcaaggc tttaccaaag ttacaagtcc ttaccctaag ttcaaacaag  1200
ttttatggtc ctatatctcc tcctcatcaa ggtcctctcg ggtttccaga gctgagaata  1260
cttgagatat ctgataataa gttactggaa agcttgtcgt caagatactt tgagaattgg  1320
aaagcatcgt ccgccatgat gaatgaatat gtgggtttat atatggttta cgagaagaat  1380
ccttatggtg tagttgtcta tacctttttg gatcgtatag atttgaaata caaggtcta  1440
aacatggagc aagcgagggt tctcacttcc tacagcgcca ttgattttc tagaaatcta  1500
cttgaaggaa atattcctga atccattgga ctttttaaagg cattgattgc actaaactta  1560
tcgaacaacg cttttacagg ccatattcct cagtctttgg caaatcttaa ggagctccag  1620
tcactagaca tgtctaggaa ccaactctca gggactattc ctaatggact caagcaactc  1680
tcgttttttg cttacataag tgtgtctcat aaccaactca agggtgaaat accacaagga  1740
acacaaatta ctgggcaatt gaaatcttcc tttgaaggga atgtaggact ttgtggtctt  1800
cctctcgagg aaaggtgctt cgacaatagt gcatcccaa cgcagcacca caagcaagac  1860
gaagaagaag aagaagaaca agtgttacac tggaaagcgg tggcaatggg gtatggacct  1920
ggattgttgg tggatttgc aattgcatat gtcattgctt catacaagcc ggagtggcta  1980
accaagataa ttggtccgaa taagcgcaga aactag                            2016

SEQ ID NO: 21            moltype = AA   length = 671
FEATURE                  Location/Qualifiers
source                   1..671
                         mol_type = protein
                         organism = Arabidopsis thaliana
SEQUENCE: 21
MKTMSKSSLR LHFLSLLLLC CVSPSSFVII RFITHNHFDG LVRCHPHKFQ ALTQFKNEFD    60
TRRCNHSNYF NGIWCDNSKV RSQSYDYGTV SVELSNQTVA SSSFIIFATL ISLTTTSPPL   120
PSLPSLFPTL RNLTKLTVLD LSHNHFSGTL KPNNSLFELH HLRYLNLEVN NFSSSLPSEF   180
GYLNNLQHCG LKEFPNIFKT LKKMEAIDVS NNRINGKIPE WLWSLPLLHL VNILNNSFDG   240
FEGSTEVLVN SSVRILLLES NNFEGALPSL PHSINAFSGL HNNFTGEIPL SICTRTSLGV   300
LDLNYNNLIG PVSQCLSNVT FVNLRKNNLE GTIPETFIVG SSIRTLDVGY NRLTGKLPRS   360
LLNCSSLEFL SVDNNRIKDT FPFWLKALPK LQVLTLSSNK FYGPISPPHQ GPLGFPELRI   420
LEISDNKFTG SLSSRYFENW KASSAMMNEY VGLYMVYEKN PYGVVVYTFL DRIDLKYKGL   480
NMEQARVLTS YSAIDFSRNL LEGNIPESIG LLKALIALNL SNNAFTGHIP QSLANLKELQ   540
SLDMSRNQLS GTIPNGLKQL SFLAYISVSH NQLKGEIPQG TQITGQLKSS FEGNVGLCGL   600
PLEERCFDNS ASPTQHHKQD EEEEEQVLH WKAVAMGYGP GLLVGFAIAY VIASYKPEWL   660
TKIIGPNKRR N                                                       671

SEQ ID NO: 22            moltype = DNA   length = 1662
FEATURE                  Location/Qualifiers
source                   1..1662
                         mol_type = genomic DNA
                         organism = Arabidopsis thaliana
SEQUENCE: 22
atgacttcct ctcgccgtct tcttcttcct ctcggagcat cgctcactag aggaagattt    60
tcttccgatc aaatccgaaa tggatttcta gaaaacttcc gtggattcgc caccgtaact   120
```

```
tcgtcggaac cggccttagc caatctggaa gcgaaatatg ccgtagcgtt gccagaatgt    180
tcaacagtag aggacgagat cacgaagatc cgtcatgaat tcgagttagc gaaacagagg    240
tttcttaata tccctgaagc tattaatagt atgccgaaga tgaatcctca agggatatat    300
gtgaataaga atctgagatt ggataatata caagtttatg gatttgatta tgattacact    360
ttggcacatt actcttctca cttacagagt ttgatctata tcttgccaa gaaacatatg    420
gttaatgagt ttagatatcc tgatgtttgc actcagtttg agtatgatcc tactttccca    480
atccgtgggt tgtactatga taaactaaaa ggatgcctca tgaaattgga tttcttcggt    540
tcaatcgagc cagatgggtg ttattttggt cgtcgtaagc ttagtaggaa ggaaatagaa    600
agcatgtatg gaacgcggca cataggtcgt gatcaagcga gaggtttggt gggattgatg    660
gatttcttct gttttagcga ggcgtgtctt atagcagaca tggtgcaata ttttgttgac    720
gccaaacttg agtttgatgc ctctaacatc tacaatgatg tcaatcgtgc tattcaacat    780
gtccatagaa gtggattggt tcatagagga attcttgctg atcccaacag atatttgcta    840
aaaaatggtc agcttctacg tttcctgaga atgcaaaag ataaggaaa gaagcttttt    900
ttgctgacca actctccgta taattttgtt gatggcggaa tgcgctttct aatggaggaa    960
tcttttggct tcggagattc ctggcgagaa ctctttgatg ttgtgattgc taaagcaaat   1020
aaaccagaat tttacacatc tgagcaccct ttccgttgtt atgattcgga gagggataat   1080
ttggcattta caaaagtgga tgcatttgac ccaagaaaag tttattatca tggttgtctt   1140
aaatccttcc ttgaaatcac aaagtggcat ggccctgagg tgatttattt cggagatcac   1200
ttatttagtg atctaagagg gccttcaaaa gctggttggc gaactgctgc cataattcat   1260
gagctcgagc gagagataca gatacaaaat gatgatagct accggtttga gcaggccaag   1320
ttccatatta tccaagagtt actcggtaga tttcacgcga ctgtatcaaa caatcagaga   1380
agtgaagcat gccaatcact tttggatgag ctgaaccagg caggcagag acgcaagagac   1440
acgatgaaac aaatgttcaa cagatctgttt ggagctacat ttgtcacaga cactggtcaa   1500
gaatcagcat tctcttatca catccaccaa tacgcagacg tttataccag taaacctgag   1560
aactttctgt tataccgacc tgaagcctgg cttcacgttc cttacgatat caagatcatg   1620
ccacatcatg tcaaggttgc ttcaaccctt ttcaaaacct ga                      1662

SEQ ID NO: 23          moltype = AA   length = 553
FEATURE                Location/Qualifiers
source                 1..553
                       mol_type = protein
                       organism = Arabidopsis thaliana
SEQUENCE: 23
MTSSRRLLLP LGASLTRGRF SSDQIRNGFL RNFRGFATVT SSEPALANLE AKYAVALPEC    60
STVEDEITKI RHEFELAKQR FLNIPEAINS MPKMNPQGIY VNKNLRLDNI QVYGFDYDYT   120
LAHYSSHLQS LIYDLAKKHM VNEFRYPDVC TQFEYDPTFP IRGLYYDKLK GCLMKLDFFG   180
SIEPDGCYFG RRKLSRKEIE SMYGTRHIGR DQARGLVGLM DFFCFSEACL IADMVQYFVD   240
AKLEFDASNI YNDVNRAIQH VHRSGLVHRG ILADPNRYLL KNGQLLRFLR MLKDKGKKLF   300
LLTNSPYNFV DGGMRFLMEE SFGFGDSWRE LFDVVIAKAN KPEFYTSEHP FRCYDSERDN   360
LAFTKVDAFD PKKVYYHGCL KSFLEITKWH GPEVIYFGDH LFSDLRGPSK AGWRTAAIIH   420
ELEREIQIQN DDSYRFEQAK FHIIQELLGR FHATVSNNQR SEACQSLLDE LNNARQRARD   480
TMKQMFNRSF GATFVTDTGQ ESAFSYHIHQ YADVYTSKPE NFLLYRPEAW LHVPYDIKIM   540
PHHVKVASTL FKT                                                     553

SEQ ID NO: 24          moltype = DNA   length = 1386
FEATURE                Location/Qualifiers
source                 1..1386
                       mol_type = genomic DNA
                       organism = Brachypodium distachyon
SEQUENCE: 24
atggagattc cggcggcgcc gccgcctcca ttgccggtgc tgtgctcgta cgtcgtcttc     60
ttgctgctgc tgtcttcgtg ctcactggcc agagggagga tcgcggtttc ttccccgggc    120
ccgtcgcctg tggccgccgc cgttacagcc aatgagaccg cttcatcctc ttcttctccg    180
gtgtttccgg ccgctcctcc cgtcgtgatc acagtggtga ggcaccacca ttaccaccgg    240
gagctggtca tctccgctgt cctcgcctgc gtcgccacca ccatgatcct cctctccaca    300
ctctacgcct ggacgatgtg gcggcggtct cgccggaccc ccacggcgg caagggccgc    360
ggccggagat cagggatcac actggtgcca atcctgagca agttcaattc agtgaagatg    420
agcaggaagg ggggccttgt gacgatgatc gagtacccgt cgctggaggc ggcgacaggc    480
aagttcggcg agagcaatgt cgtcgtgtc ggcggcttcg gttgcgttta taagcggcg    540
tttgatgcg gtgccaccgc cgccgtgaag aggcttgaag gcggcgggcc ggattgcgag    600
aaggaattcg agaatgagct ggatttgctt ggcaggatca ggcacccaaa catagtgtct    660
ctcctggget tctgtgtcca tggtggcaat cactacattg tttatgagct catggagaag    720
ggatcattgg agacacagct gcatgggtct tcacatggat ctgctctgag ctggcacgtt    780
cggatgaaga tcgcgctcga tacggcgagg ggattagagt atcttcatga gcactgacat    840
ccacctgtga tccatagggaa tctgaaacct tctaatatac tttagatttc agacttcaat    900
gctaagattg cagattttgg ccttgcgtc accggtggga atctcaacaa agggaacctg    960
aagctttccg ggaccttggg ttatgtagcc cctgagtact tattagatgg gaagttgact   1020
gagaagacg atgtatacgc atttggagta gtgcttctag agctcctgat gggaaggaag   1080
cctgttgaga aaatgtcacc atctcagttg caatcaattg tgtcatggga tatgcctcag   1140
ctgaccgaca gatcgaagct ccccaacata attgactggg tgatcaagga caccatggac   1200
ccaaaacact tgtaccaagt tgcagcagtg gctgttctat gtgtgcagcc cgaaccgagc   1260
tacagaccac tgataacaga tgttctccac tctcttgttc ctctagtgcc tcggagctc   1320
ggaggaacac tcagggttgc agagccacct tcaccttctc cagaccaaag acattatcct   1380
tgttga                                                             1386

SEQ ID NO: 25          moltype = DNA   length = 1302
FEATURE                Location/Qualifiers
source                 1..1302
                       mol_type = genomic DNA
```

```
                        organism = Brassica napus
SEQUENCE: 25
atgaagaaac tggttcatct tcagttttg tttcttgtca agatcttgc tactcaattc        60
ctcactcctt cttcatcatc tttgctgct tcaaatcctt ctatagctcc tgtttacacc      120
tccatgacta cttttctctcc aggaattcaa atgggaagtg gtgaagaaca cagattagat    180
gcacataaga aactcctgat tggtcttata atcagttcct cttctcttgg tatcataatc    240
ttgatttgct ttggcttctg gatgtactgt cgcaagaaag ctcccaaacc catcaagatt   300
ccggatgccg agagtgggac ttcatcattt tcaatgtttg tgaggcggct aagctcaatt   360
aaaactcaca gaacatctag caatcagggt tatgtgcagc gtttcgattc caagacgcta   420
gagaaagcca caggcggttt caaagacagt aatgtaatcg gacagggcgg tttcggatgc   480
gtttacaagg cttctttgga cagcaacact aaagcagcgg ttaaaaagat cgaaaacgtt   540
acccaagaag caaaacgaga atttcagaat gaagttgagc tgttgagcaa gatccagcac   600
tccaatatta tatcattgtt gggctctgca agtgaaatca actcgagttt cgtcgtttat   660
gagttgatgg agaaaggatc cttagatgat cagttacatg gaccttcgtg tggatccgct   720
ctaacatggc atatgcgtat gaagattgct ctagatacag ctagaggact agagtatctc   780
catgaacatt gtcgtccacc agttatccac agggacctga atcgtcaa tattcttctt   840
gattcttcct tcaatgccaa gatttcagat tttggtctgg ctgtatcggt tggagtgcat   900
gggagtaaca acattaaact ctctgggaca cttggttatg ttgccccga atatctccca    960
gacgaaagt tgacggataa gagtgatgtc tatgcatttg gggtggttct tcttgaactt   1020
ttgttgggta gcggccggt tgagaaattg agtccatctc agtgtcaatc tcttgtgact   1080
tgggcaatgc cacaacttac cgatagatcg aaactcccaa acatcgtgga tccggttata   1140
aaagatacaa tggatcttaa gcacttatac caagtgcgtg ttctgtgcgta            1200
cagccagaac cgagttaccg gccgctgata accgatgttc ttcattcact tgttccattg   1260
gttccggtag agctaggagg gactctccgg ttaacccgat ga                     1302

SEQ ID NO: 26              moltype = AA   length = 433
FEATURE                    Location/Qualifiers
source                     1..433
                           mol_type = protein
                           organism = Brassica napus
SEQUENCE: 26
MKKLVHLQFL FLVKIFATQF LTPSSSSFAA SNPSIAPVYT SMTTFSPGIQ MGSGEEHRLD      60
AHKKLLIGLI ISSSSLGIII LICFGFWMYC RKKAPKPIKI PDAESGTSSF SMFVRRLSSI    120
KTHRTSSNQG YVQRFDSKTL EKATGGFKDS NVIGQGGFGC VYKASLDSNT KAAVKKIENV    180
TQEAKREFQN EVELLSKIQH SNIISLLGSA SEINSSFVVY ELMEKGSLDD QLHGPSCGSA    240
LTWHMRMKIA LDTARGLEYL HEHCRPPVIH RDLKSSNILL DSSFNAKISD FGLAVSVGVH    300
GSNNIKLSGT LGYVAPEYLL DGKLTDKSDV YAFGVVLLEL LLGRRPVEKL SPSQCQSLVT    360
WAMPQLTDRS KLPNIVDPVI KDTMDLKHLY QVAAMAVLCV QPEPSYRPLI TDVLHSLVPL    420
VPVELGGTLR LTR                                                       433

SEQ ID NO: 27              moltype = DNA   length = 657
FEATURE                    Location/Qualifiers
source                     1..657
                           mol_type = genomic DNA
                           organism = Cichorium endivia
SEQUENCE: 27
atttttggtg ttgaaatgat gcacaacgga tctttggaat cccaattgca tggtccgtct      60
catggaactg gcttaagctg gcagcatcga atgaaaattg cacttgatat tgcacgagga    120
ctagagtatc tccacgagcg ctgtaccccg cctgtgattc atagagatct gaaatcgtcc    180
aacattcttc taggttcgaa ctacaatgct aaactttctg atttcgggct cgcgattact    240
ggtgggattc agggcaagaa caacgtaaag ctttcggaca cattaggtta tgtagctcca    300
gaatacctct tagatggtaa acttactgat aaaagtgatg tttatgcgtt ggagttgta    360
cttcttgaac ttttgatagg tagaaaacca gtggagaaaa tgtcaccatc tcaatgccaa    420
tctatcgtta catgggcaat gcctcaacta accgaccgat caaagcttcc taacatcgtt    480
gatcccgtga ttagagatac aatggacttg aagcacttgt atcaagttgc tgcggttgct    540
gtgctatgtg tacaaccgga accgagttac aggccattga taacagatgt tttgcattcg    600
ttcatcccac ttgtacctgt tgagcttgga gggtcgctaa gagttaccga atcttga        657

SEQ ID NO: 28              moltype = AA   length = 218
FEATURE                    Location/Qualifiers
source                     1..218
                           mol_type = protein
                           organism = Cichorium endivia
SEQUENCE: 28
IFGVEMMHNG SLESQLHGPS HGTGLSWQHR MKIALDIARG LEYLHERCTP PVIHRDLKSS      60
NILLGSNYNA KLSDFGLAIT GGIQGKNNVK LSGTLGYVAP EYLLDGKLTD KSDVYAFGVV    120
LLELLIGRKP VEKMSPSQCQ SIVTWAMPQL TDRSKLPNIV DPVIRDTMDL KHLYQVAAVA    180
VLCVQPEPSY RPLITDVLHS FIPLVPVELG GSLRVTES                            218

SEQ ID NO: 29              moltype = DNA   length = 474
FEATURE                    Location/Qualifiers
source                     1..474
                           mol_type = genomic DNA
                           organism = Citrus clementina
SEQUENCE: 29
aattcggcac gagggctgga ttccagtttt aatgcaaagc tttcagattt tggcctttct      60
gtgactgctg gaaccagag taggaatgtt aagatctctg gaactctggg ttatgttgcc    120
ccggagtacc tattagaagg aaaactaact gataaagtg atgtatatgc tttcggagtt    180
gtattgctgg aactttttgat ggggagaagg cctgtggaaa agatgtcacc aactcaatgt    240
```

```
caatcaatgg tcacatgggc catgcctcag ctcaccgata gatcaaagct tccaaacatt    300
gtggatccag taattagaga cacaatggat ttaaagcact tataccaggt agccgctgtg    360
gcagtgctat gtatacaacc tgaaccaagt tataggccat tgataaccga cgttctgcat    420
tccctcattc ctcttgtacc taccgacctt ggagggtcac tccgagtgac ctaa          474

SEQ ID NO: 30            moltype = AA   length = 157
FEATURE                  Location/Qualifiers
source                   1..157
                         mol_type = protein
                         organism = Citrus clementina
SEQUENCE: 30
NSARGLDSSF NAKLSDFGLS VTAGTQSRNV KISGTLGYVA PEYLLEGKLT DKSDVYAFGV     60
VLLELLMGRR PVEKMSPTQC QSMVTWAMPQ LTDRSKLPNI VDPVIRDTMD LKHLYQVAAV    120
AVLCIQPEPS YRPLITDVLH SLIPLVPTDL GGSLRVT                             157

SEQ ID NO: 31            moltype = DNA   length = 770
FEATURE                  Location/Qualifiers
source                   1..770
                         mol_type = genomic DNA
                         organism = Citrus sinensis
SEQUENCE: 31
ggattgtgtt tgtggcttta tcatttgaag tactccttca aatccagtaa caagaatgca     60
aagagcaaag attctgagaa tggagttgtg ttatcatcat ttttgggcaa attcacttct    120
gtgaggatgg ttagtaagaa gggatctgct atttcattta ttgagtataa gctgttagag    180
aaagccaccg acagttttca tgagagtaat atattgggtg agggtggatt tggatgtgtt    240
tacaaggcta aattggatga taacttgcac gtcgctgtca aaaaattaga ttgtgcaaca    300
caagatgccg gcagagaatt tgagaatgag gtggatttgc tgagtaatat tcaccaccca    360
aatgttgttt gtctgttggg ttatagtgct catgatgaca aaggtttat tgtttatgaa     420
ttgatggaaa atcggtccct tgatattcaa ttgcatggtc cttctcatgg atcagcattg    480
acttggcata tgcgaatgaa aattgctctt gataccgcta aggattagaa atatttacat    540
gagcactgca accctgcagt cattcataga gatctgaaat cctccaatat acttctagat    600
tccaagttta atgctaagct ctcagatttt ggtcttgcca taaccgatgg atcccaaaac    660
aagaacaatc ttaagctttc gggcactttg ggatatgtgg ctcccgagta tctttagat    720
ggtaaattga cagacaagag tgatgtctat gcttttggag ttgtgcttct                770

SEQ ID NO: 32            moltype = AA   length = 257
FEATURE                  Location/Qualifiers
source                   1..257
                         mol_type = protein
                         organism = Citrus sinensis
SEQUENCE: 32
GLCLWLYHLK YSFKSSNKNA KSKDSENGVV LSSFLGKFTS VRMVSKKGSA ISFIEYKLLE     60
KATDSFHESN ILGEGGFGCV YKAKLDDNLH VAVKKLDCAT QDAGREFENE VDLLSNIHHP    120
NVVCLLGYSA HDDTRFIVYE LMENRSLDIQ LHGPSHGSAL TWHMRMKIAL DTARGLEYLH    180
EHCNPAVIHR DLKSSNILLD SKFNAKLSDF GLAITDGSQN KNNLKLSGTL GYVAPEYLLD    240
GKLTDKSDVY AFGVVLL                                                   257

SEQ ID NO: 33            moltype = DNA   length = 621
FEATURE                  Location/Qualifiers
source                   1..621
                         mol_type = genomic DNA
                         organism = Coffea canephora
SEQUENCE: 33
gcattgacat ggcatcttag gatgaaaatt gcccttgatg tagctagagg attagaattt     60
ttgcatgagc actgccaccc agcagtgatc catagaatgc tgaaatcatc taatatcctt    120
ctggattcaa atctcaatgc taagctatct gattttggtc ttgccattct tgatggggct    180
caaaataaga acaacatcaa gctttctgga acctttgggct atgtagctcc agagtacctc    240
ttagatggta aattgactga caagagtgat gtttatgctt ttggagtggt gcttttggag    300
cttctcctga gaagaaagcc tgtggagaag ctggcaccag ctcaatgcca atctatagtc    360
acatgggcta tgcctcagct gacagataga tcaaagcttc caaacatcg ggatcctgtg     420
attagaaatg ctatggatat aaagcactta ttccaggttg ctgcagtcgc tgtgctatgc    480
gtgcagcctg aaccaagcta tcgaccactg ataacagatg tgttcattc ccttgttccc     540
cttgttccta tggagcttgg cgggacgctc agagttgaac gacctgcttc tgtgacctct    600
ctgttgattg attctacctg a                                              621

SEQ ID NO: 34            moltype = AA   length = 206
FEATURE                  Location/Qualifiers
source                   1..206
                         mol_type = protein
                         organism = Coffea canephora
SEQUENCE: 34
ALTWHLRMKI ALDVARGLEF LHEHCHPAVI HRDLKSSNIL LDSNLNAKLS DFGLAILDGA     60
QNKNNIKLSG TLGYVAPEYL LDGKLTDKSD VYAFGVVLLE LLLRRKPVEK LAPAQCQSIV    120
TWAMPQLTDR SKLPNIVDPV IRNAMDIKHL FQVAAVAVLC VQPEPSYRPL ITDVLHSLVP    180
LVPMELGGTL RVERPASVTS LLIDST                                         206

SEQ ID NO: 35            moltype = DNA   length = 411
FEATURE                  Location/Qualifiers
source                   1..411
```

```
                        mol_type = genomic DNA
                        organism = Eucalyptus gunnii
SEQUENCE: 35
actgaggtga cccggaagaa aaacagggta aagctatcgg gcactttggg ttatgtagcc     60
ccagaaatatg tcttggatgg taaattgact gataagagtg atgtctatgc ctttggagtt    120
gtgcttttgg agctcctttt gagaagaagg cctcttgaga tagtagcacc cactcagtgc    180
cagtctattg ttacatgggc catgcctcag ctgaccgacc gaactaagct tccagatatt    240
gtggatcctg taattagaga tgcgatggat gtcaagcact ataccaggc agctgctgtt     300
gctgttttgt gtctgcaacc agaaccgatc taccggccac tgataacgga tgtactccac    360
tctctcattc cacttgtacc cgttgaactt gggggaacgc tgaagaccta g              411

SEQ ID NO: 36           moltype = AA   length = 136
FEATURE                 Location/Qualifiers
source                  1..136
                        mol_type = protein
                        organism = Eucalyptus gunnii
SEQUENCE: 36
TEVTRKKNRV KLSGTLGYVA PEYVLDGKLT DKSDVYAFGV VLLELLLRRR PLEIVAPTQC     60
QSIVTWAMPQ LTDRTKLPDI VDPVIRDAMD VKHLYQAAAV AVLCLQPEPI YRPLITDVLH    120
SLIPLVPVEL GGTLKT                                                    136

SEQ ID NO: 37           moltype = DNA   length = 522
FEATURE                 Location/Qualifiers
source                  1..522
                        mol_type = genomic DNA
                        organism = Festuca arundinacea
SEQUENCE: 37
acgaggcctc gtgccatact tttggattca gatttcaatg ccaagatttc ggatttcggt     60
cttgcagtgt caagtggaaa tcgcaccaaa ggtaatctga agctttccgg aactttgggc    120
tatgttgctc ctgagtactt attagacggg aagttgacaa agaagagtga tgtatatgcg    180
ttcggagtag tacttcttga gcttttgtta ggaaggaggc caattgagaa gatggcccca    240
tctcaatgcc aatcaattgt tacatgggc atgcctcagc taattgacag atcaaagctc     300
ccaaccataa ttgaccccgt gatcaggaac acgatggacc tgaagcactt gtaccaagtt    360
gctgcagtgg ctgtgctctg tgtgcagcca gaaccaagtt ataggccact aatcacagat    420
gtgctccact ctctgattcc cctggtgccc atggagctcg gagggtcact gagggctacc    480
ttggaatcgc ctcgcgtatc acaacatcgt tctccctgct ga                       522

SEQ ID NO: 38           moltype = AA   length = 173
FEATURE                 Location/Qualifiers
source                  1..173
                        mol_type = protein
                        organism = Festuca arundinacea
SEQUENCE: 38
TRPRAILLDS DFNAKISDFG LAVSSGNRTK GNLKLSGTLG YVAPEYLLDG KLTEKSDVYA     60
FGVVLLELLL GRRPIEKMAP SQCQSIVTWA MPQLIDRSKL PTIIDPVIRN TMDLKHLYQV    120
AAVAVLCVQP EPSYRPLITD VLHSLIPLVP MELGGSLRAT LESPRVSQHR SPC            173

SEQ ID NO: 39           moltype = DNA   length = 740
FEATURE                 Location/Qualifiers
source                  1..740
                        mol_type = genomic DNA
                        organism = Ginkgo biloba
SEQUENCE: 39
cctttattga atagattgaa ctccttccgt ggttctagga gaaagggatg tgcatatata     60
attgaatatt ctctgctgca agcagccaca aataattta gtacaagtga catccttgga    120
gaggggtggtt ttgggtgtgt atacagagct aggttagatg atgatttctt tgctgctgtg    180
aagaagttag atgagggcag caagcaggct gagtatgaat tcagaatga agttgaacta     240
atgagcaaaa tcagacatcc aaatcttgtt tctttgctgg ggttctgcat tcatgggaag    300
actcggttgc tagtctacga gctcatgcaa aatggttctt tggaagacca attacatggg    360
ccatctcatg gatccgcact tacatggtac ctgcgcatga aaatagccct tgattcagca    420
agggtctag aacacttgca cgagcactgc aatcctgctg tgattcatcg tgatttcaaa     480
tcatcaaata tccttctgga tgcaagcttc aatgccaagc tttcagattt ggtcttgca    540
gtaacagctg caggaggtat tggtaatgct aatgtcgagc tactgggcac tttgggatat    600
gtagctccag aatacctgct tgatggcaag ttgacggaga aaagtgatgt ctatggatt     660
ggagttgttc ttttggagct aattatggga agaaaagccag ttgataaatc tgtggcaact    720
gaaagtcaat cgctagtttc                                                740

SEQ ID NO: 40           moltype = AA   length = 247
FEATURE                 Location/Qualifiers
source                  1..247
                        mol_type = protein
                        organism = Ginkgo biloba
SEQUENCE: 40
PLLNRLNSFR GSRRKGCAYI IEYSLLQAAT NNFSTSDILG EGGFGCVYRA RLDDDFFAAV     60
KKLDEGSKQA EYEFQNEVEL MSKIRHPNLV SLLGFCIHGK TRLLVYELMQ NGSLEDQLHG    120
PSHGSALTWY LRMKIALDSA RGLEHLHEHC NPAVIHRDFK SSNILLDASF NAKLSDFGLA    180
VTAAGGIGNA NVELLGTLGY VAPEYLLDGK LTEKSDVYGF GVVLLELIMG RKPVDKSVAT    240
ESQSLVS                                                              247
```

-continued

```
SEQ ID NO: 41            moltype = DNA   length = 1254
FEATURE                  Location/Qualifiers
source                   1..1254
                         mol_type = genomic DNA
                         organism = Glycine max
SEQUENCE: 41
atgaaaatga agcttctcct catgcttctt cttcttgttc ttcttcttca ccaacccatt    60
tgggctgcag accctcctgc ttcttctcct gctttatctc caggggagga gcagcatcac   120
cggaataata aagtggtaat agctatcgtc gtagccacca ctgcacttgc tgcactcatt   180
ttcagtttct tatgcttctg ggttatcat cataccaagt atccaacaaa atccaaattc    240
aaatccaaaa attttcgaag tccagatgca gagaagggga tcaccttagc accgtttgtg   300
agtaaattca gttccatcaa gattgttggc atggacgggt atgttccaat aattgactat   360
aagcaaatag aaaaaacgac caataatttt caagaaagta acatcttggg tgagggcggt   420
tttggacgtg tttacaaggc ttgtttggat cataacttgg atgttgcagt caaaaaacta   480
cattgtgaga ctcaacatgc tgagagagaa tttgagaacg aggtgaatat gttaagcaaa   540
attcagcatc cgaatataat atctttactg gggttgtagca tggatggtta cacgaggctc   600
gttgtctatg agctgatgca taatggatca ttggaagctc agttacatgg accttctcat   660
ggctcggcat tgacttggca catgaggatg aagattgcgc ttgacacagc aagaggatta   720
gaatatctgc acgagcactg tcaccctgca gtgatccata gggatatgaa atcttctaat   780
attctcttag atgcaaactt caatgccaag ctgtctgatt ttggtcttgc cttaactgat   840
gggtcccaaa gcaagaagaa cattaaacta tcgggtacct gggatacgt agcaccggag    900
tatctctag atggtaaatt aagtgataaa agtgatgtct atgcttttgg ggttgtgcta    960
ttggagctcc tactaggaag gaagccagta gaaaaactgg taccagctca atgccaatct  1020
attgtcacat gggccatgcc acacctcacg gacagatcca agcttccaag cattgtggat  1080
ccagtgatta gaataacaat ggatcccaag cacttgtacc aggttgctgc tgtagctgtg  1140
ctgtgcgtgc aaccagaacc tagttaccgt ccactgatca ttgatgttct tcactcactc  1200
atccctcttg ttcccattga gcttggagga acactaagag tttcacaagt aatt         1254

SEQ ID NO: 42            moltype = AA   length = 418
FEATURE                  Location/Qualifiers
source                   1..418
                         mol_type = protein
                         organism = Glycine max
SEQUENCE: 42
MKMKLLLMLL LLVLLLHQPI WAADPPASSP ALSPGEEQHH RNNKVVIAIV VATTALAALI    60
FSFLCFWVYH HTKYPTKSKF KSKNFRSPDA EKGITLAPFV SKFSSIKIVG MDGYVPIIDY   120
KQIEKTTNNF QESNILGEGG FGRVYKACLD HNLDVAVKKL HCETQHAERE FENEVNMLSK   180
IQHPNIISLL GCSMDGYTRL VVYELMHNGS LEAQLHGPSH GSALTWHMRM KIALDTARGL   240
EYLHEHCHPA VIHRDMKSSN ILLDANFNAK LSDFGLALTD GSQSKKNIKL SGTLGYVAPE   300
YLLDGKLSDK SDVYAFGVVL LELLLGRKPV EKLVPAQCQS IVTWAMPHLT DRSKLPSIVD   360
PVIKNTMDPK HLYQVAAVAV LCVQPEPSYR PLIIDVLHSL IPLVPIELGG TLRVSQVI     418

SEQ ID NO: 43            moltype = DNA   length = 702
FEATURE                  Location/Qualifiers
source                   1..702
                         mol_type = genomic DNA
                         organism = Helianthus argophyllus
SEQUENCE: 43
actcaagcat caaatattg taaatctttt gggtattgtg ttcatgatga cacaaggttt     60
ttggtctatg aaatgatgca tcaaggctct ttggactcac aattgcatgg accaactcat   120
ggaaccgcat taacctggca tcgaagaatg aaagtcgcac ttgatattgc tcgaggatta   180
gagtatcttc atgaacgatg caaccccgcc gtgattcata gagatcttaa gtcatcgaac   240
attttgctag attccaattt caatgctaaa atttcgaatt ttgcacttgc taccactgag   300
ctccatgcga agaacaaagt taagctttcg gctacttctg gttatttggc tccggaatac   360
ctatcagaag gtaaacttac cgataaaagc gacgtatatg cattcggagt agtacttctt   420
gggcttttaa tcggtagaaa accagtggag aaaaatgtca catctttatt tcaatctatt   480
gtcacatggg caatgcctca gttaacagac cggtcaaagc ttccaaacat cgttgaccct   540
gtgattagaa atacaatgga cctgaagcac ttatatcaag ttgctgctgt agccgtactt   600
tgcgtgcaac ccgaaccaag ttacagaccg ttgattacag acgtactaca ctcattcatt   660
ccactcgtac ccgttgatct tggagggtca ttaagagctt aa                      702

SEQ ID NO: 44            moltype = AA   length = 233
FEATURE                  Location/Qualifiers
source                   1..233
                         mol_type = protein
                         organism = Helianthus argophyllus
SEQUENCE: 44
TQASKYCKSF GYCVHDDTRF LVYEMMHQGS LDSQLHGPTH GTALTWHRRM KVALDIARGL    60
EYLHERCNPP VIHRDLKSSN ILLDSNFNAK ISNFALATTE LHAKNKVKLS ATSGYLAPEY   120
LSEGKLTDKS DVYAFGVVLL GLLIGRKPVE KMSPSLFQSI VTWAMPQLTD RSKLPNIVDP   180
VIRDTMDLKH LYQVAAVAVL CVQPEPSYRP LITDVLHSFI PLVPVDLGGS LRA           233

SEQ ID NO: 45            moltype = DNA   length = 752
FEATURE                  Location/Qualifiers
source                   1..752
                         mol_type = genomic DNA
                         organism = Helianthus ciliaris
SEQUENCE: 45
cgatcatttc gttgcggctg taaaaaactc catggtccag aaccagatgc ccaaaaaggg    60
```

```
tttgagaatg aagtagattg gttaggtaaa ctcaagcatc aaaatattgt aaatttttg   120
ggttattgtg ttcatgatga cacaaggttt ttggtctatg aaatgatgca tcaaggctct  180
ttggactcac aattgcatgg accaactcat ggaaccgcat taacctgca tcgaagaatg   240
aaagtcgcac ttgatattgc tcgaggatta gagtatcttc atgaacgatg caacccgcct  300
gtgattcata gagatctcaa gtcatcgaac attttgctag attccaattt caatgctaaa  360
atttcgaatt ttgcacttgc taccactgag ctccatgcga agaacaaagt taagctttcg  420
ggtacttctg gttatttggc tccggaatac ctatccgaag gtaaacttac cgataaaagt  480
gatgtatatg cattccggagt agtacttctt gagcttttaa tcggtagaaa accagtggag  540
aaaatgtcac catctttatt tcaatctatt gtcacatggg caatgcctca gctaacagac  600
cggtcaaagc ttccaaacat tgttgaccct gtgattagag atacaatgga cctgaagcac  660
ttgtatcaag ttgctgctgt agccgtactt tgcgtgcaac ccgaaccaag ttacagaccg  720
ttgattacag acgtactaca ctcattcatt cc                                752

SEQ ID NO: 46          moltype = AA   length = 251
FEATURE                Location/Qualifiers
source                 1..251
                       mol_type = protein
                       organism = Helianthus ciliaris
SEQUENCE: 46
RSFRCGCKKL HGPEPDAQKG FENEVDWLGK LKHQNIVNFL GYCVHDDTRF LVYEMMHQGS   60
LDSQLHGPTH GTALTWHRRM KVALDIARGL EYLHERCNPP VIHRDLKSSN ILLDSNFNAK  120
ISNFALATTE LHAKNKVKLS GTSGYLAPEY LSEGKLTDKS DVYAFGVVLL ELLIGRKPVE  180
KMSPSLFQSI VTWAMPQLTD RSKLPNIVDP VIRDTMDLKH LYQVAAVAVL CVQPEPSYRP  240
LITDVLHSFI P                                                      251

SEQ ID NO: 47          moltype = DNA   length = 630
FEATURE                Location/Qualifiers
source                 1..630
                       mol_type = genomic DNA
                       organism = Helianthus exilis
SEQUENCE: 47
atgatgcatc aagactcttt ggactcacaa ttgcatggac caactcatgg aaccgcatta   60
acctggcatc gaagaatgaa agtcgcactt gatattgctc gaggattaga gtatcttcat  120
gaacgatgca acccgcctgt gattcataga gatctcaagt catcgaacat tttgctagat  180
tccaatttca atgctaaaat ttcgaatttt gcacttgcta ccactgagct ccatgcgaag  240
aacaaagtta agctttcggg tacttctggt tatttggctc cggaatacct atccgaaggt  300
aaacttaccg ataaaagtga tgtatatgca ttcggagtag tacttcttga gcttttaatc  360
ggtagaaaac cagtggagaa aatgtcacca tctttatttc aatctattgt cacatgggca  420
atgcctcagc taacagaccg gtcaaagctt ccaaacattg ttgaccctgt gattagagat  480
acaatggacc tgaagcactt gtatcaagtt gctgctgtag ccgtactttg cgtgcaaccc  540
gaaccaagtt acagaccgtt gattacagac gtactacact cattcattcc actcgtaccc  600
gttgatcttg gagggtcatt aagagcttaa                                   630

SEQ ID NO: 48          moltype = AA   length = 209
FEATURE                Location/Qualifiers
source                 1..209
                       mol_type = protein
                       organism = Helianthus exilis
SEQUENCE: 48
MMHQDSLDSQ LHGPTHGTAL TWHRRMKVAL DIARGLEYLH ERCNPPVIHR DLKSSNILLD   60
SNFNAKISNF ALATTELHAK NKVKLSGTSG YLAPEYLSEG KLTDKSDVYA FGVVLLELLI  120
GRKPVEKMSP SLFQSIVTWA MPQLTDRSKL PNIVDPVIRD TMDLKHLYQV AAVAVLCVQP  180
EPSYRPLITD VLHSFIPLVP VDLGGSLRA                                   209

SEQ ID NO: 49          moltype = DNA   length = 780
FEATURE                Location/Qualifiers
source                 1..780
                       mol_type = genomic DNA
                       organism = Hordeum vulgare
SEQUENCE: 49
aatttgagag gtgagctgga tttgcttcag aggattcagc attcgaatat agtgtccctt   60
gtgggcttct gcattcatga ggagaaccgc ttcattgttt atgagctgat ggtgaatgga  120
tcacttgaaa cacagcttca tgggccatca catggatcag ctctgagttg cacattcgg   180
atgaagattg ctcttgatac agcaagggga ttggagtatc ttcacgagca tgcaatccca  240
ccaatcatcc atagggatct gaagtcgtct aacatacttt tgaattcaga ctttaatgca  300
aagatttcag attttggcct tgcagtgaca agtggaaatc gcagcaaagg gaatctgaag  360
cttttccggta ctttgggtta tgttgcccct gagtacttac tagatgggaa gttgactgag  420
aagagcgatg tatatgcatt tggagtagta cttcttgagc ttcttttggg aaggaggcca  480
gttgagaaga tggcaccatc tcagtgtcaa tcaattgtta catgggccat gccccagcta  540
attgacagat ccaagctccc taccataatc gaccccgtga tcaggacac gatggatcgg  600
aagcacttgt accaagttgc tgcagtggct gtgctctgcg tgcagccaga accaagctac  660
aggccactga tcagagatgt cctccactct ctgattcccc tggtgccat ggaccttgga   720
gggacgctga ggatcaaccc ggaatcgcct tgcacgacac gaaatcaatc tccctgctga  780

SEQ ID NO: 50          moltype = AA   length = 259
FEATURE                Location/Qualifiers
source                 1..259
                       mol_type = protein
                       organism = Hordeum vulgare
```

```
SEQUENCE: 50
NLRGELDLLQ  RIQHSNIVSL  VGFCIHEENR  FIVYELMVNG  SLETQLHGPS  HGSALSWHIR   60
MKIALDTARG  LEYLHEHCNP  PIIHRDLKSS  NILLNSDFNA  KISDFGLAVT  SGNRSKGNLK  120
LSGTLGYVAP  EYLLDGKLTE  KSDVYAFGVV  LLELLLGRRP  VEKMAPSQCQ  SIVTWAMPQL  180
IDRSKLPTII  DPVIRDTMDR  KHLYQVAAVA  VLCVQPEPSY  RPLITDVLHS  LIPLVPMDLG  240
GTLRINPESP  CTTRNQSPC                                                  259

SEQ ID NO: 51          moltype = DNA   length = 816
FEATURE                Location/Qualifiers
source                 1..816
                       mol_type = genomic DNA
                       organism = Ipomoea batatas
SEQUENCE: 51
cggggggctct tatcactcat tgctgctgct actgcactgg gtacaagctt attgctcatg   60
ggttgcttct ggatttatca tagaaagaaa atccacaaat ctcatgcata tattcatagc  120
ccagatgtag ttaaaggtct tgcattatcc tcatatatta gcaaatacaa ctccttcaag  180
tcgaattgtg tgaaacgaca tgtctcgttg gggagtaca atacactcga gtcggccaca   240
aatagttttc aagaaagcga gatctgggt ggaggggggt tcgggcttgt gtacaaggga  300
aaactagaag acaacttgta tgtagctgtg aagaggctgg aagttggaag acaaaacgca  360
attaaagaat tcgaggctga aatagaggta ttgggcacga ttcagcaccc gaatataatt  420
tcgttgttgg gatatagcat tcatgctgac acgaggctgc tagtttatga actgatgcag  480
aatggatctc tggagtatca actacatgga ccttcccatg gatcagcatt agcgtggcat  540
aatagattga aaatcgcact tgatacagca aggggattag aatatttaca tgaacattgc  600
aaaccaccag ttatccatag agatctgaaa tcctccaata ttcttctaga tgccaacttc  660
aatgccaaga tctcagattt tggtcttgct gtgcgcgatg gggctcaaaa caaaaataac  720
attaagctct cgggaaccgt tggctatgta gctccagaat acctattaga tggaatacta  780
acagataaaa gtgatgttta tggcttccga gttgta                             816

SEQ ID NO: 52          moltype = AA   length = 272
FEATURE                Location/Qualifiers
source                 1..272
                       mol_type = protein
                       organism = Ipomoea batatas
SEQUENCE: 52
RGLLSLIAAA  TALGTSLLLM  GCFWIYHRKK  IHKSHDIIHS  PDVVKGLALS  SYISKYNSFK   60
SNCVKRHVSL  WEYNTLESAT  NSFQESEILG  GGGFGLVYKG  KLEDNLYVAV  KRLEVGRQNA  120
IKEFEAEIEV  LGTIQHPNII  SLLGYSIHAD  TRLLVYELMQ  NGSLEYQLHG  PSHGSALAWH  180
NRLKIALDTA  RGLEYLHEHC  KPPVIHRDLK  SSNILLDANF  NAKISDFGLA  VRDGAQNKNN  240
IKLSGTVGYV  APEYLLDGIL  TDKSDVYGFR  VV                               272

SEQ ID NO: 53          moltype = DNA   length = 867
FEATURE                Location/Qualifiers
source                 1..867
                       mol_type = genomic DNA
                       organism = Lactuca sativa
SEQUENCE: 53
ggggatatac gtgtagaatc agcaacaaat aacttcggtg aaagcgagat attaggcgta   60
ggtggatttg gatgcgtgta taaagctcga ctcgatgata atttgcatgt agctgttaaa  120
agattagatg gtattagtca agacgccatt aaagaattcc agacggaggt ggatctattg  180
agtaaaattc atcatccgaa tatcatcacc ttattggat attgtgttaa tgatgaaacc  240
aagcttcttg tttatgaact gatgcataat ggatctttaa aaactcaatt acatggtcct  300
tccagtggat ccaatttaac atggcattgc aggatgaaga ttgctctaga tacagcaaga  360
ggattagaat atttgcatga gaactgcaaa ccatcggtga ttcatagaga tctgaaatca  420
tctaatatcc ttctggattc cagcttcaat gctaagcttt cagattttgg tcttgctata  480
atggatgggg cccagaacaa aaacaacatt aagctttggg ggacattggg ttatgtagct  540
cccgagtatc ttttagatgg aaaattgacg gataaagtg acgtgtatgc gtttggagtt  600
gtgcttttag agcttttact tggaaggcga cctgtagaaa aattagcaga gtcgcaatgc  660
caatctattg tcacttgggc tatgccacaa ttaacagaca gatcaaagct tccgaatatt  720
gtagatcccg tgatcagata cacaatggat ctcaagcacc tgtaccaagt tgctgcggtc  780
gctgtgttat gtgtacaacc cggaccaagc taccggccat ttataaaccg acgtcttgca  840
ttctctgatc cctcttgttc cccgtga                                       867

SEQ ID NO: 54          moltype = AA   length = 288
FEATURE                Location/Qualifiers
source                 1..288
                       mol_type = protein
                       organism = Lactuca sativa
SEQUENCE: 54
GDIRVESATN  NFGESEILGV  GGFGCVYKAR  LDDNLHVAVK  RLDGISQDAI  KEFQTEVDLL   60
SKIHHPNIIT  LLGYCVNDET  KLLVYELMHN  GSLETQLHGP  SSGSNLTWHC  RMKIALDTAR  120
GLEYLHENCK  PSVIHRDLKS  SNILLDSSFN  AKLSDFGLAI  MDGAQNKNNI  KLSGTLGYVA  180
PEYLLDGKLT  DKSDVYAFGV  VLLELLLGRR  PVEKLAESQC  QSIVTWAMPQ  LTDRSKLPNI  240
VDPVIRYTMD  LKHLYQVAAV  AVLCVQPGPS  YRPFINRRLA  FSDPSCSP                288

SEQ ID NO: 55          moltype = DNA   length = 804
FEATURE                Location/Qualifiers
source                 1..804
                       mol_type = genomic DNA
                       organism = Medicago truncatula
```

```
SEQUENCE: 55
aagttgaact gtgaatgtca atatgctgag agagaatttg agaatgaggt ggatttgtta   60
agtaaaattc aacatccaaa tgtaatttct ctactgggct gtagcagtaa tgaggattca  120
aggtttattg tctatgagtt gatgcaaaat ggatcattgg aaactcaatt acatggacca  180
tctcatggct cagcattgac ttggcatatg aggatgaaga ttgctcttga cacagctaga  240
ggtttaaaat atctgcatga gcactgctac cctgcagtga tccatagaga tctgaaatct  300
tctaatattc ttttagatgc aaacttcaat gccaagcttt ctgattttgg tcttgcaata  360
actgatgggt cccaaaacaa gaataacatc aagctttcag gcacattggg gtatgttgcc  420
ccggagtatc ttttagatgg taaattgaca gataaaagtg atgtgtatgc ttttggagtt  480
gtgcttcttg agcttctatt aggaagaaag cctgtgtgaa aacttacacc atctcaatgc  540
cagtctattg tcacatgggc catgccacag ctcacagaca gatccaagct tccaaacatt  600
gtggataatg tgattaagaa tacaatggat cctaagcact ataccaggt tgctgctgtg  660
gctgtattat gtgtgcaacc agagccgtgc taccgccctt tgattgcaga tgttctacac  720
tccctcatcc ctcttgtacc tgttgagctt ggaggaacac tcagagttgc acaagtgacg  780
cagcaaccta agaattctag ttaa                                         804

SEQ ID NO: 56            moltype = AA   length = 267
FEATURE                  Location/Qualifiers
source                   1..267
                         mol_type = protein
                         organism = Medicago truncatula
SEQUENCE: 56
KLNCECQYAE REFENEVDLL SKIQHPNVIS LLGCSSNEDS RFIVYELMQN GSLETQLHGP   60
SHGSALTWHM RMKIALDTAR GLKYLHEHCY PAVIHRDLKS SNILLDANFN AKLSDFGLAI  120
TDGSQNKNNI KLSGTLGYVA PEYLLDGKLT DKSDVYAFGV VLLELLLGRK PVEKLTPSQC  180
QSIVTWAMPQ LTDRSKLPNI VDNVIKNTMD PKHLYQVAAV AVLCVQPEPC YRPLIADVLH  240
SLIPLVPVEL GGTLRVAQVT QQPKNSS                                      267

SEQ ID NO: 57            moltype = DNA   length = 636
FEATURE                  Location/Qualifiers
source                   1..636
                         mol_type = genomic DNA
                         organism = Nicotiana tabacum
SEQUENCE: 57
cagttgcatg gacctcctcg tggatcagct ttgaattggc atcttcgcat ggaaattgca   60
ttggatgtgg ctaggggact agaataccte catgagcgct gtaaccccce tgtaatccat  120
agagatctca aatcgtctaa tgttctattg gattcctact tcaatgcaaa gctttctgac  180
ttttggccta gctatagctg gatggaactt aaacaagagc accgtaaagt ctttcgggaa  240
ctctgggata tgtggctcca gagttaccte ttagatggaa aattaactga taagagtgat  300
gtctatgctt tcggcattat acttctggag cttctaatgg ggagaagacc attggagaaa  360
ctagcaggag ctcagtgcca atctatcgtc acatgggcaa tgccacagct tactgacagg  420
tcaaagctcc caaatattgt tgatcctgtc atcagaaacg gaatgggcct caagcacttg  480
tatcaagttg ctgctgtagc cgtgctatgt gtacaaccag aaccaagtta ccgaccactg  540
ataacagatg tcctgcactc cttcattccc cttgtaccaa ttgagcttgg tgggtccttg  600
agagttgtgg attctgcatt atctgttaac gcataa                            636

SEQ ID NO: 58            moltype = AA   length = 211
FEATURE                  Location/Qualifiers
source                   1..211
                         mol_type = protein
                         organism = Nicotiana tabacum
SEQUENCE: 58
QLHGPPRGSA LNWHLRMEIA LDVARGLEYL HERCNPPVIH RDLKSSNVLL DSYFNAKLSD   60
FWPSYSWMEL KQEHRKVFRE LWDMWLQSYL LDGKLTDKSD VYAFGIILLE LLMGRRPLEK  120
LAGAQCQSIV TWAMPQLTDR SKLPNIVDPV IRNGMGLKHL YQVAAVAVLC VQPEPSYRPL  180
ITDVLHSFIP LVPIELGGSL RVVDSALSVN A                                 211

SEQ ID NO: 59            moltype = DNA   length = 1437
FEATURE                  Location/Qualifiers
source                   1..1437
                         mol_type = genomic DNA
                         organism = Oryza sativa
SEQUENCE: 59
atggagatgg cgctaactcc attgccgctc ctgtgttcgt ccgtcttgtt cttggtgcta   60
tcttcgtgct cgttggccaa tgggagggat acgccttctt cttcttcttc ttcttcttct  120
tcttcttctt cttcttcttc ttcttcttct tcttcttctt ctccggcgac gtctactgtg  180
gccaccggca tttccgccgc cgccgccgcc ccgccaatg gacggccgc cttgtcttcg  240
gcagttccgg cgcctccgcc tgtttgtgatc gtagtgcacc accatttcca ccgcgagctg  300
gtcatccgcg ccgtccgcgc ctgcatcgcc accgtcacga tcttcctttc cacgctctac  360
gcttggacac tatgcggcg atctcgccgg agcaccggcg gcaaggtcac caggagctca  420
gacgcagcga aggggatcaa gctggtgccg atcttgagca ggttcaactc ggtgaagatg  480
agcaggaaga ggctggttgg gatgttcgag tacccgtcgc tggaggcagc gacagagaag  540
ttcagcgaga gcaacatgct cggtgtcggc gggtttggcc gcgtctacaa gcggcgcgttc  600
gacgccggag ttaccggcgg ggtgaagcgg ctcgacgcg gcgggcccga ctgcgagaag  660
gaattcgaga tgagctgga tttgcttggc aggatcaggc accccaacat tgtgtccctc  720
ttgggcttct gtatccatga ggggaatcac tacattgttt atgagctgat ggagaaggga  780
tcactggaaa cacagcttca tgggtcttca catggatcaa ctctgagctg gcacatccgg  840
atgaagatcg cccttgacac ggccagggga ttagagtacc tcatgagca ctgcagtcca  900
ccagtgatcc atagggatct gaaatcgtct aacatacttt tggattcaga cttcaatgct  960
```

```
aagattgcag attttggtct tgctgtgtct agtgggagtg tcaacaaagg gagtgtgaag   1020
ctctccggga ccttgggtta tgtagctcct gagtacttgt tggatgggaa gttgactgaa   1080
aagagcgatg tatacgcgtt cggagtagtg cttctagagc tccttatggg gaggaagcct   1140
gttgagaaga tgtcaccatc tcagtgccaa tcaattgtga catgggcaat gccacagttg   1200
accgacagat cgaagctccc cagcatagtt gacccagtca tcaaggacac catggatcca   1260
aaacacctgt accaagttgc agcagtggct gttctatgcg tgcaggctga accaagctac   1320
aggccactga tcacagatgt gctccactct cttgttcctc tagtgccgac ggagctcgga   1380
ggaacactaa gagctggaga gccaccttcc ccgaacctga ggaattctcc atgctga      1437

SEQ ID NO: 60           moltype = AA   length = 478
FEATURE                 Location/Qualifiers
source                  1..478
                        mol_type = protein
                        organism = Oryza sativa
SEQUENCE: 60
MEMALTPLPL LCSSVLFLVL SSCSLANGRD TPSSSSSSSS SSSSSSSSSS SSSSPATSTV    60
ATGISAAAAA AANGTAALSS AVPAPPPVVI VVHHHFHREL VIAAVLACIA TVTIFLSTLY   120
AWTLWRRSRR STGGKVTRSS DAAKGIKLVP ILSRFNSVKM SRKRLVGMFE YPSLEAATEK   180
FSESNMLGVG GFGRVYKAAF DAGVTAAVKR LDGGGPDCEK EFENELDLLG RIRHPNIVSL   240
LGFCIHEGNH YIVYELMEKG SLETQLHGSS HGSTLSWHIR MKIALDTARG LEYLHEHCSP   300
PVIHRDLKSS NILLDSDFNA KIADFGLAVS SGSVNKGSVK LSGTLGYVAP EYLLDGKLTE   360
KSDVYAFGVV LLELLMGRKP VEKMSPSQCQ SIVTWAMPQL TDRSKLPSIV DPVIKDTMDP   420
KHLYQVAAVA VLCVQAEPSY RPLITDVLHS LVPLVPTELG GTLRAGEPPS PNLRNSPC     478

SEQ ID NO: 61           moltype = DNA   length = 891
FEATURE                 Location/Qualifiers
source                  1..891
                        mol_type = genomic DNA
                        organism = Physcomitrella sp.
SEQUENCE: 61
tactctcttt tacaaactgc tacgaacaac ttcagctcct ccaatttgct gggcgaggga    60
agtttcgggc atgtgtataa agcgagactc gattatgatg tctatgccgc tgtaaagaga   120
cttaccagcg taggaaaaca gcccaaaaa gaactccagg gagaggtgga tctgatgtgc    180
aagataagac atcccaactt ggtggctctc ctgggctatt caaatgacgg cccagagccc   240
ttggttgtgt acgagctcat gcagaatggt tcacttcatg atcagctcca tggcccctca   300
tgcgggagtg cactcacctg gtacctacga ctaaagattg ctcttgaagc tgccagcaga   360
ggactggagc acctgcatga agctgcaag cctgcaataa tccacagaga cttcaaggca    420
tccaacatcc tcttggacgc cagcttcaat gcgaaggtgt ccgactttgg tatagcggta   480
gctctggagg aaggtggcgt ggtgaaagac gacgtacaag tgcaaggcac cttcgggtac   540
attgctcctg agtaccgtag ggacgggaca ttgacagaga gagtgatgt ttacggattt     600
ggagtagtat tgcttgagct gctgacaggc agactgccca ttgatacgtc cttaccactc   660
ggatcgcaat ctctagtgac atgggtaaca cccatactaa ctaaccgagc aaagctgatg   720
gaagttatcg acccccaccct tcaagatacg ctgaacgtga agcaacttca ccaggtggcc   780
gcagtggcag tccttttcgt ccaagcgaaa cccagctacc gccctctcat cgccgacgtg   840
gttcagtcac tggctccgct ggtgcctcaa gagctcggcg gcgcattgcg a             891

SEQ ID NO: 62           moltype = AA   length = 297
FEATURE                 Location/Qualifiers
source                  1..297
                        mol_type = protein
                        organism = Physcomitrella sp.
SEQUENCE: 62
YSLLQTATNN FSSSNLLGEG SFGHVYKARL DYDVYAAVKR LTSVGKQPQK ELQGEVDLMC    60
KIRHPNLVAL LGYSNDGPEP LVVYELMQNG SLHDQLHGPS CGSALTWYLR LKIALEAASR   120
GLEHLHESCK PAIIHRDFKA SNILLDASFN AKVSDFGIAV ALEEGGVVKD DVQVQGTFGY   180
IAPEYLMDGT LTEKSDVYGF GVVLLELLTG RLPIDTSLPL GSQSLVTWVT PILTNRAKLM   240
EVIDPTLQDT LNVKQLHQVA AVAVLCVQAE PSYRPLIADV VQSLAPLVPQ ELGGALR      297

SEQ ID NO: 63           moltype = DNA   length = 1065
FEATURE                 Location/Qualifiers
source                  1..1065
                        mol_type = genomic DNA
                        organism = Picea sp.
SEQUENCE: 63
acctcagatg cctataggg tattccactc atgcctctcc tgaatcgttt gaactcccgt     60
atttccaaga agaagggatg tgcaactgca attgaatatt ctaagctgca agcagctaca   120
aataacttca gcagcaataa cattcttgga gagggtggat ttgcgtgtgt atacaaggcc   180
atgtttgatg atgattcctt tgctgctgtg aagaagctag atgagggtag cagacaggct   240
gagcatgaat ttcagaatga agtggagctg atgagcaatc tccgacatcc aaaccttgtt   300
tctttgcttg ggttctgctc tcatgaaaat acacgttct tagtatatga tctgatgcag   360
aatggctctt ggaagaccaa attacatggg ccatctcacg gatctgcact acatggttt    420
ttgcgcataa agatagcact tgattcagca aggggtctag aacacttgca tgagcactgc   480
aaccctgcag tgattcatcg agatttcaaa tcatcaaata ttcttcttga tgcaagcttc   540
aacgccaagc tttcagattt tggtcttgca gtaacaaggg caggatgtac tgcaataca   600
aatattgatc tagtagggac attgggatat gtagctccag aatacctact tgatggtaaa   660
ttgacagaga aaagtgatgt ctatgcatat ggagttgttt tgttggagct acttttggga   720
agaaaagccaa ttgataaatc tctaccagt gaatgccaat ctctcatttc ttgggcaatg   780
ccacagctaa cagatagaga aaagctccca actatatag accccatgat caaaggcaca   840
atgaacttga aacacctata tcaagtagca gctgttgcaa tgctatgtgt gcagccagaa   900
```

```
cccagttaca ggccattaat agctgacgtt gtgcactctc tcattcctct cgtaccaata    960
gaactcgggg gaactttaaa gctctctaat gcacgaccca ctgagatgaa gttatttact   1020
tcttcccaat gcagtgttga gattgcttcc aacccaaaat tgtga                  1065

SEQ ID NO: 64           moltype = AA   length = 354
FEATURE                 Location/Qualifiers
source                  1..354
                        mol_type = protein
                        organism = Picea sp.
SEQUENCE: 64
TSDAYRGIPL MPLLNRLNSR ISKKKGCATA IEYSKLQAAT NNFSSNNILG EGGFACVYKA    60
MFDDDSFAAV KKLDEGSRQA EHEFQNEVEL MSKIRHPNLV SLLGFCSHEN TRFLVYDLMQ   120
NGSLEDQLHG PSHGSALTWF LRIKIALDSA RGLEHLHEHC NPAVIHRDFK SSNILLDASF   180
NAKLSDFGLA VTSAGCAGNT NIDLVGTLGY VAPEYLLDGK LTEKSDVYAY GVVLLELLFG   240
RKPIDKSLPS ECQSLISWAM PQLTDREKLP TIVDPMIKGT MNLKHLYQVA AVAMLCVQPE   300
PSYRPLIADV VHSLIPLVPI ELGGTLKLSN ARPTEMKLFT SSQCSVEIAS NPKL         354

SEQ ID NO: 65           moltype = DNA   length = 596
FEATURE                 Location/Qualifiers
source                  1..596
                        mol_type = genomic DNA
                        organism = Pinus sp.
SEQUENCE: 65
aattcggcac gaggagaaca cttgcacgag cactgcaacc ctgcagtgat tcaccgagat    60
ttcaaatcat caaatattct tcttgatgca agcttcaacg ccaagctttc agattttggt   120
cttgcagtaa aaagtgcagg atgtgctggt aacacaaata ttgatctagt agggacattg   180
ggatatgtag ctccagaata catgcttgat ggtaaattga cagagaaaag tgatgtctat   240
gcatatggag ttgttttgtt agagctactt tttggaagaa agccaattga taatctcta   300
ccaagtgaat gccaatctct catttcttgg gcaatgccac agctaacaga tagagaaaag   360
ctcccgacta taatagatcc catgatcaaa ggcgcaatga acttgaaaca cctatatca   420
gtggcagctg ttgcagtgct atgtgtgcag ccagaaccca gttacaggcc attaatagct   480
gacgttgtgc actctctcat tcctctcgta ccagtagaac ttgggggaac attaaagtca   540
tcacccactg agatgaagtc atttgcttct cccaatgca gtgcccacgt tgcttc       596

SEQ ID NO: 66           moltype = AA   length = 199
FEATURE                 Location/Qualifiers
source                  1..199
                        mol_type = protein
                        organism = Pinus sp.
SEQUENCE: 66
NSARGEHLHE HCNPAVIHRD FKSSNILLDA SFNAKLSDFG LAVKSAGCAG NTNIDLVGTL    60
GYVAPEYMLD GKLTEKSDVY AYGVVLLELL FGRKPIDKSL PSECQSLISW AMPQLTDREK   120
LPTIIDPMIK GAMNLKHLYQ VAAVAVLCVQ PEPSYRPLIA DVVHSLIPLV PVELGGTLKS   180
SPTEMKSFAS SQCSAHVAS                                               199

SEQ ID NO: 67           moltype = DNA   length = 1377
FEATURE                 Location/Qualifiers
source                  1..1377
                        mol_type = genomic DNA
                        organism = Populus sp.
SEQUENCE: 67
atgttcttgt ttcctaaaac agttcctatt tggtttttc atctgtgtct agtagcagtt     60
catgccatac aagaagaccc acctgtccct tcaccatctc cctctctcat ttctcctatt   120
tcaacttcaa tggctgcctt ctctccaggg gttgaatcgg aaatgggaat caagaccac   180
cccagcatg atgacctcca caggaaaata atcttgtttg tcactgttgc ttgttgcata   240
cttgttatca tccttctttc tttgtgttct tgtttcattt actataagaa gtcctcacaa   300
aagaaaaaag ctactcggtg ttcagatgtg gagaaaggc tttcattggc accatttttg   360
ggcaaattca gttccttgaa aatggttagt aataggggat ctgtttcatt aattgagtat   420
aagatactag agaaaggaac aaacaatttt ggcgatgata aattgttggg aaagggagga   480
tttggacgtg tatataaggc tgtaatggaa gatgactcaa gtgctgcagt caagaaacta   540
gactgcgcaa ctgatgatgc gcagagagaa tttgagaatg aggtggattt gttaagcaaa   600
tttcaccatc caaatataat ttctattgtg gttttagtg ttcatgagga atggggttc    660
attatttatg agttaatgcc aaatgggtgc cttgaagatc tactgcatgg accttctcgt   720
ggatcttcac taaattggca tttaaggttg aaaattgctc ttgatacagc aagaggatta   780
gaatatctgc atgaattctg caagccagca gtgatccata gagatctgaa atcatcgaat   840
attcttttgg acgccaactt caatgccaag ctgtcagatt ttggtcttgc tgtagctgat   900
agctctcata caagaaaaa gctcaagctt tcaggcactg tgggttatgt agccccagag   960
tatatgttag atggtaatt gacggataag agtgatgtct atgcttttgg agttgtgctt  1020
ctagcttcc tattaggaag aaggcctgta gaaaaactga caccagctca ttgccaatct  1080
atagtaacat gggccatgcc tcagctcact aacagagctg tgcttccaac ccttgtggat  1140
cctgtgatca gagattcagt agatgagaag tacttgttcc aggttgcagc agtagccgtg  1200
ttgtgtatc aaccagagcc aagttaccgc cctctcataa cagatgttgt gcactctctc  1260
gtcccattag ttcctcttga gcttggaggg acactaaaga ttccacagcc tacaactccc  1320
agaggtcaac gacaaggccc atcaaagaaa ctgttttggg atggtgctgc ctctgct     1377

SEQ ID NO: 68           moltype = AA   length = 459
FEATURE                 Location/Qualifiers
source                  1..459
                        mol_type = protein
```

```
                            organism = Populus sp.
SEQUENCE: 68
MPLFPKTVPI WFFHLCLVAV HAIQEDPPVP SPSPSLISPI STSMAAFSPG VESEMGIKDH    60
PQHDDLHRKI ILLLTVACCI LVIILLSLCS CFIYYKKSSQ KKKATRCSDV EKGLSLAPFL   120
GKFSSLKMVS NRGSVSLIEY KILEKGTNNF GDDKLLGKGG FGRVYKAVME DDSSAAVKKL   180
DCATDDAQRE FENEVDLLSK FHHPNIISIV GFSVHEEMGF IIYELMPNGC LEDLLHGPSR   240
GSSLNWHLRL KIALDTARGL EYLHEFCKPA VIHRDLKSSN ILLDANFNAK LSDFGLAVAD   300
SSHNKKKLKL SGTVGYVAPE YMLDGELTDK SDVYAFGVVL LELLLGRRPV EKLTPAHCQS   360
IVTWAMPQLT NRAVLPTLVD PVIRDSVDEK YLFQVAAVAV LCIQPEPSYR PLITDVVHSL   420
VPLVPLELGG TLRVPQPTTP RGQRQGPSKK LFLDGAASA                          459

SEQ ID NO: 69           moltype = DNA  length = 693
FEATURE                 Location/Qualifiers
source                  1..693
                        mol_type = genomic DNA
                        organism = Saccharum officinarum
SEQUENCE: 69
gctgctgcgg tgaagagatt ggatggtggg gctggggcac atgattgcga gaaggaattc    60
gagaatgagt tagatttgct tggaaagatt cggcatccga acattgtgtc ccttgtgggc   120
ttctgtattc atgaggagaa ccgtttcatt gtttatgagc tgatagagaa tgggtcgttg   180
gattcacaac ttcatgggcc atcacatggt tcagctctga gctggcatat tcggatgaag   240
attgctcttg acacgtcaag gggattagag tacctgcatg agcactgcaa cccaccagtt   300
atccataggg atctgaagtc atctaacata cttttagatt cagacttcag tgctaagatt   360
tcagattttg gccttgcggt gattagtggg aatcacagca aagggaattt aaagcttcct   420
gggactatgg gctatgtggc ccctgagtac ttattggatg ggaagttgac tgagaagagc   480
gatgtatatg cgtttggggt ggtacttcta gaacttctac tgggaaggaa acctgcttag   540
aagatggcac aatctcaatg ccaatcaatt gttacatggg ccatgcctca gctaactgat   600
agatccaaac tccctaacat aattgatccc atgatcaaga acacaatgga tctgaaacac   660
ttgtaccaag ttgctgcaat ggctgtgctc tga                                693

SEQ ID NO: 70           moltype = AA   length = 230
FEATURE                 Location/Qualifiers
source                  1..230
                        mol_type = protein
                        organism = Saccharum officinarum
SEQUENCE: 70
AAAVKRLDGG AGAHDCEKEF ENELDLLGKI RHPNIVSLVG FCIHEENRFI VYELIENGSL    60
DSQLHGPSHG SALSWHIRMK IALDTARGLE YLHEHCNPPV IHRDLKSSNI LLDSDFSAKI   120
SDFGLAVISG NHSKGNLKLS GTMGYVAPEY LLDGKLTEKS DVYAFGVVLL ELLLGRKPVE   180
KMAQSQCQSI VTWAMPQLTD RSKLPNIIDP MIKNTMDLKH LYQVAAMAVL              230

SEQ ID NO: 71           moltype = DNA  length = 414
FEATURE                 Location/Qualifiers
source                  1..414
                        mol_type = genomic DNA
                        organism = Triphysaria versicolor
SEQUENCE: 71
accctcggtt atgtagctcc tgagtatctg ttagatggta agttaacaga gaaaagcgat    60
gtgtatgggt ttggagtagt gttactcgag cttctgcttg ggaagaagcc tatggagaaa   120
gtggcaacaa cagcaactca gtgccagatg atagtcacat ggaccatgcc tcagctcact   180
gacagaacga aacttccgaa tatcgtggat ccggtgatca gaaactccat ggatttaaag   240
cacttgtacc aggttgctgc tgtggcagta ttgtgtgtgc agccagaacc gagttatcgg   300
ccattgataa ctgatatttt gcattctctt gtgccccttg tcctgttga cttggtgggg   360
acgctcagga actcgataac aatggctaca acaacaatt ctcctgaaag ctaa          414

SEQ ID NO: 72           moltype = AA   length = 137
FEATURE                 Location/Qualifiers
source                  1..137
                        mol_type = protein
                        organism = Triphysaria versicolor
SEQUENCE: 72
TLGYVAPEYL LDGKLTEKSD VYGFGVVLLE LLLGKKPMEK VATTATQCQM IVTWTMPQLT    60
DRTKLPNIVD PVIRNSMDLK HLYQVAAVAV LCVQPEPSYR PLITDILHSL VPLVPVELGG   120
TLRNSITMAT TTISPES                                                  137

SEQ ID NO: 73           moltype = DNA  length = 1140
FEATURE                 Location/Qualifiers
variation               1000
                        note = n is a, c, g, or t
variation               1080
                        note = n is a, c, g, or t
variation               1088
                        note = n is a, c, g, or t
source                  1..1140
                        mol_type = genomic DNA
                        organism = Triticum aestivum
SEQUENCE: 73
cggcacgagg ggctggtggc catgatcgag tacccgtcgc tggaggcggc gacgggcaag    60
ttcagcgaga gcaacgtgct cggcgtcggc gggttcggct cgtctacaa ggcggcgttc   120
```

```
gacggcggcg ccaccgccgc cgtgaagagg ctcgaaggcg gcgagccgga ctgcgagaag    180
gagttcgaga atgagctgga cttgcttggc aggatcaggc acccaaacat agtgtccctc    240
ctgggcttct gcgtccatgg tggcaatcac tacattgttt atgagctcat ggagaaggga    300
tcattggaga cacaactgca tgggccttca catggatcgg ctatgagctg gcacgtccgg    360
atgaagatcg cgctcgacac ggcgaaggga ttagagtatc ttcatgagca ctgcaatcca    420
ccagtcatcc ataggatct gaaatcgtct aatatactct tggattcaga cttcaatgct     480
aagattgcag attttggcct tgcagtgaca agtgggaatc ttgacaaagg gaacctgaag    540
atctctggga ccttgggata tgtagctccc gagtacttat tagatgggaa gttgaccgag    600
aagagcgacg tctacgcgtt tggagtagtg cttctagagc tcctgatggg gaggaagcct    660
gttgagaaga tgtcaccatc tcagtgccaa tcaattgtgt catgggccat gcctcagcta    720
accgacagat cgaagctacc caacatcatc gacccggtga tcaaggacac aatggaccca    780
aagcatttat accaagttgc ggcggtggcc gttctatgcg tgcagccgga accgagttac    840
agaccgctga taacagacgt tctccactcc cttgttcctc tggtacccgc ggatctcggg    900
gggaacgctc agagttacag agccgcattc tccacaccaa atgtaccatc cctcttgaga    960
agtgatccta caagtttcgt cgaagcgggg aaagcgaatn tatacggtcc agcggtagat   1020
ggctgttatt ttggtactta tatctcaccc tgtcctgctg cttatcttag gatgagtgan   1080
gagctccnac ctgctgcttt tgctggttgg gcagagagaa tacagttctg gttaggattg   1140

SEQ ID NO: 74          moltype = AA  length = 380
FEATURE                Location/Qualifiers
VARIANT                334
                       note = Xaa can be any naturally occurring amino acid
VARIANT                360
                       note = Xaa can be any naturally occurring amino acid
VARIANT                363
                       note = Xaa can be any naturally occurring amino acid
source                 1..380
                       mol_type = protein
                       organism = Triticum aestivum
SEQUENCE: 74
RHEGLVAMIE YPSLEAATGK FSESNVLGVG GFGCVYKAAF DGGATAAVKR LEGGEPDCEK     60
EFENELDLLG RIRHPNIVSL LGFCVHGGNH YIVYELMEKG SLETQLHGPS HGSAMSWHVR    120
MKIALDTARG LEYLHEHCNP PVIHRDLKSS NILLDSDFNA KIADFGLAVT SGNLDKGNLK    180
ISGTLGYVAP EYLLDGKLTE KSDVYAFGVV LLELLMGRKP VEKMSPSQCQ SIVSWAMPQL    240
TDRSKLPNII DPVIKDTMDP KHLYQVAAVA VLCVQPEPSY RPLITDVLHS LVPLVPADLG    300
GNAQSYRAAF STPNVPSLLR SDPTSFVEAG KANXYGPAVD GCYFGTYISP CPAAYLRMSX    360
ELXPAAFAGW AERIQFWLGL                                                380

SEQ ID NO: 75          moltype = DNA  length = 978
FEATURE                Location/Qualifiers
source                 1..978
                       mol_type = genomic DNA
                       organism = Vitis vinifera
SEQUENCE: 75
atgaaagtga ttgggagaaa gggttatgtc tcttttattg attataaggt actagaaact     60
gcaacaaaca atttcagga aagtaatatc ctgggtgagg gcgggtttgg ttgcgtctac    120
aaggcgcggt tggatgataa ctcccatgtg gctgtgaaga agatagatgg tagaggccag    180
gatgctgaga gagaatttga gaatgaggtg gatttgttga ctaaaattca gcacccaaat    240
ataatttctc tcctgggtta cagcagtcat gaggagtcaa agtttcttgt ctatgagctg    300
atgcagaatg gatctctgga aactgaattg cacggacctt ccatggatc atctctaact     360
tggcatatcc gaatgaaaat cgctctggat gcagcaagag gattagagta tctacatgag    420
cactgcaacc caccagtcat ccatagagat cttaaatcat ctaatattct tctggattca    480
aacttcaatg ccaagctttc ggatttggt ctagctgtaa ttgatgggcc tcaaaacaag     540
aacaacttga agctttcagg caccctgggt tatctagctc ctgagtatct tttagatggt    600
aaactgactg ataagagtga tgtgtatgca tttggagtgg tgcttctaga gctactactg    660
ggaagaaagc ctgtgaaaa actggcacca gctcaatgcc agtccattgt cacatgggcc     720
atgccacagc tgactgacag atcaaagctc ccaggcatcg ttgaccctgt ggtcagagac    780
acgatggatc taaagcattt ataccaagtt gctgctgtag ctgtgctatg tgtgcaacca    840
gaaccaagtt accggccatt gataacagat gttctgcact cctcatccc actcgttcca     900
gttgagttgg gagggatgct aaaagttacc cagcaagcgc cgcctatcaa caccactgca    960
ccttctgctg gaggttga                                                  978

SEQ ID NO: 76          moltype = AA  length = 325
FEATURE                Location/Qualifiers
source                 1..325
                       mol_type = protein
                       organism = Vitis vinifera
SEQUENCE: 76
MKVIGRKGYV SFIDYKVLET ATNNFQESNI LGEGGFGCVY KARLDDNSHV AVKKIDGRGQ     60
DAEREFENEV DLLTKIQHPN IISLLGYSSH EESKFLVYEL MQNGSLETEL HGPSHGSSLT    120
WHIRMKIALD AARGLEYLHE HCNPPVIHRD LKSSNILLDS NFNAKLSDFG LAVIDGPQNK    180
NNLKLSGTLG YLAPEYLLDG KLTDKSDVYA FGVVLLELLL GRKPVEKLAP AQCQSIVTWA    240
MPQLTDRSKL PGIVDPVVRD TMDLKHLYQV AAVAVLCVQP EPSYRPLITD VLHSLIPLVP    300
VELGGMLKVT QQAPPINTTA PSAGG                                          325

SEQ ID NO: 77          moltype = DNA  length = 1377
FEATURE                Location/Qualifiers
source                 1..1377
                       mol_type = genomic DNA
```

```
                        organism = Zea mays
SEQUENCE: 77
atgccgccgc catcgccgct cctccgttcc tccgccttcg tcgtcttgct gctcctggtg      60
tgtcgcccgt tgttggtcgc caatggggag gccacgccgc cttctccggg atggccaccg     120
gcggctcagc ccgcgctgca gcctgcaccc accgccagcg gcggcgtggc ctccgtgctt     180
ccttcggccg tggcgcctcc tcccttaggt gtggttgtgg cggagaggca ccaccacctc     240
agcagggagc tcgtcgctgc cattatcctc tcatccgtcg ccagcgtcgt gatccccatt     300
gccgcgctgt atgccttctt gctgtggcga cgatcacggc gagccctggt ggattccaag     360
gacacccaga gcatagatac cgcaaggatt gcttttgcgc cgatgttgca cagctttggc     420
tcgtacaaga ctaccaagaa gagtgccgcg gcgatgatga attacacatc tttggaggca     480
gcgacagaaa acttcagtga gagcaatgtc cttggatttg tgggtttggg tctgtgtac      540
aaagccaatt tgatgggag gtttgctgct cggtgaaga gactgatgg tggggcacat        600
gattgcaaga aggaattcga gaatgagcta gacttgcttg gaagaattcg acatccgaac     660
atcgttcccc ttgtgggctt ctgcattcat gaggagaacc gttcgttgt ttatgagctg      720
atggagagtg gtcgttgga ttcgcaactt catgggccat acatggttc agctctgagc       780
tggcatattc ggatgaagat tgctctcgac acagcaaggg gattagagta cctgcatgag     840
cactgcaacc caccggttat ccatagggat cttaagtcat ctaacatact tttagattca     900
gacttcagcg ctaagatttc agactttggc ctggcagtga ctagtgggaa tcacagcaaa     960
gggaatttaa agctttctgg gactatgggc tatgtggctc ctgagtactt attagatggg    1020
aagctgactg agaagagcga tgtatacgcg tttggggtag tacttctaga actcctgctg    1080
ggaaggaaac ctgtcgagaa gatggcacaa tctcagtgcc gatcaatcgt tacatgggcc    1140
atgcctcagc taactgatag atccaagctc cgaacataa ttgatcccat gatcaagaac     1200
acaatggatc tgaaacactt gtaccaagtt gctgcagtgg ccgtgctctg cgtgcagcca    1260
gagccgagtt acaggccact gatcaccgac gtgcttcact cactggtacc tctagtgccc    1320
acggagcttg aggaacgct gaggatcggc ccggaatcgc cctacctacg ctactaa        1377

SEQ ID NO: 78              moltype = AA   length = 458
FEATURE                    Location/Qualifiers
source                     1..458
                           mol_type = protein
                           organism = Zea mays
SEQUENCE: 78
MPPPSPLLRS SAFVVLLLLV CRPLLVANGR ATPPSPGWPP AAQPALQPAP TASGGVASVL      60
PSAVAPPPLG VVVAERHHHL SRELVAAIIL SSVASVVIPI AALYAFLLWR RSRRALVDSK     120
DTQSIDTARI AFAPMLNSFG SYKTTKKSAA AMMDYTSLEA ATENFSESNV LGFGGFGSVY     180
KANFDGRFAA AVKRLDGGAH DCKKEFENEL DLLGKIRHPN IVSLVGFCIH EENRFVVYEL     240
MESGSLDSQL HGPSHGSALS WHIRMKIALD TARGLEYLHE HCNPPVIHRD LKSSNILLDS     300
DFSAKISDFG LAVTSGNHSK GNLKLSGTMG YVAPEYLLDG KLTEKSDVYA FGVVLLELLL     360
GRKPVEKMAQ SQCRSIVTWA MPQLTDRSKL PNIIDPMIKN TMDLKHLYQV AAVAVLCVQP     420
EPSYRPLITD VLHSLVPLVP TELGGTLRIG PESPYLRY                             458

SEQ ID NO: 79              moltype = DNA   length = 1188
FEATURE                    Location/Qualifiers
source                     1..1188
                           mol_type = genomic DNA
                           organism = Zea mays
SEQUENCE: 79
atgttgctcg cgtgtcctgc agtgatcatc gtggagcgcc accgtcattt ccaccgtgag      60
ctagtcatcg cctccatcct cgcctcaatc gccatggtcg cgattatcct ctccacgctg     120
tacgcgtgga tcccgcgcag gcggtcccgc cggctgcccc gcggcatgag cgcagacacc     180
gcgagggga tcatgctggc gccgatcctg agcaagttca actcgctcaa gacgagcagg     240
aaggggctcg tggcgatgat cgagtacccg tcgctggagg cagcgacagg gggttcagt      300
gagagcaacg tgctcggcgt aggcggcttc ggttgcgtct acaaggcagt cttcgatggc     360
ggcgttaccg cggcggtcaa gaggctggag ggaggtggcc ctgagtgcga aggaattcc      420
gagaatgagc tggatctgct tggcaggatt cggcacccca acatcgtgtc cctgctgggc     480
ttttgtgttc acgaggggaa tcactacatt gtttatgagc tcatggagaa gggatccctg     540
gacacacagc tgcatgggc ctcacatgga tcagcgctga cctggcatat ccggatgaag     600
atcgcactcg acatggccag gggattagaa tacctccatg agcactgcag tccaccagtg     660
atccatagg atctgaagtc atctaacata cttttagatt ctgacttcaa tgctaagatt      720
tcagattttg gtcttgcagt gaccagtggg aacattgaca agggaagcat gaagctttca     780
gggaccttgg gttatgtggc ccctgagtac ctattagatg ggaagctgac tgaaaagagt     840
gacgtatatg catttggagt ggtgcttctt gagctactaa tgggaaggaa gcctgtcgag     900
aagatgagtc aaactcagtg ccaatcaatt gtgacgtggg ccatgccgca gctgactgac     960
agaacaaaac ttcccaacat agttgaccca gtgatcaagg acaccatgga tccaaagcat    1020
ttgtaccaag tggcagcagt ggcagttcta tgtgtgcaac cagaaccaag ttacagaccg    1080
ctgattactg atgttctcca ctctcttgtc cctctagtcc ctgtgagct cggagggaca     1140
ctgagggttg tagagccacc ttccccaaac ctaaacatt ctccttgt                  1188

SEQ ID NO: 80              moltype = AA   length = 396
FEATURE                    Location/Qualifiers
source                     1..396
                           mol_type = protein
                           organism = Zea mays
SEQUENCE: 80
MLLACPAVII VERHRHFHRE LVIASILASI AMVAIILSTL YAWIPRRRSR RLPRGMSADT      60
ARGIMLAPIL SKFNSLKTSR KGLVAMIEYP SLEATGGFS ESNVLGVGGF GCVYKAVFDG     120
GVTAAVKRLE GGGPECEKEF ENELDLLGRI RHPNIVSLLG FCVHEGNHYI VYELMEKGSL    180
DTQLHGASHG SALTWHIRMK IALDMARGLE YLHECSPPV IHRDLKSSNI LLDSDFNAKI    240
SDFGLAVTSG NIDKGSMKLS GTLGYVAPEY LLDGKLTEKS DVYAFGVVLL ELLMGRKPVE    300
```

```
KMSQTQCQSI VTWAMPQLTD RTKLPNIVDP VIRDTMDPKH LYQVAAVAVL CVQPEPSYRP    360
LITDVLHSLV PLVPVELGGT LRVVEPPSPN LKHSPC                              396

SEQ ID NO: 81              moltype = DNA   length = 1086
FEATURE                    Location/Qualifiers
source                     1..1086
                           mol_type = genomic DNA
                           organism = Gossypium sp.
SEQUENCE: 81
atgaagaaga agcttgtgct gcatctgctt cttttccttg tttgtgctct tgaaaacatt      60
gttttggccg tacaaggccc tgcttcatca cccatttcta ctcccatctc tgcttcaatg    120
gctgccttct ctccagctgg gattcaactt ggaggtgagg agcacaagaa atggatcca     180
accaagaaaa tgttattagc tctcattctt gcttgctctt cattgggtgc aattatctct    240
tccttgttct gtttatggat ttattacagg aagaattcaa gcaaatcctc taaaaatggc    300
gctaagagct cagatggtga aaagggaat  ggtttggcac catatttggg taaattcaag    360
tctatgagga cggtttccaa agagggtat  gcttcgttta tggactataa gatacttgaa    420
aaagctacaa acaagttcca tcatggtaac attctgggtg agggtggatt tggatgtgtt    480
tacaaggctc aattcaatga tgttcttat  gctgctgtta agaagttgga ctgtgcaagc    540
caagatgctg aaaagaata  tgagaatgag gtgggtttgc tatgtagatt taagcattcc    600
aatataattt cactgttggg ttatagcagt gataacgata caaggtttat tgtttatgag    660
ttgatggaaa atggttcttt ggaaactcaa ttacatggac cttctcatgg ttcatcatta    720
acttggcata ggaggatgaa aattgctttg gatacagcaa ggattagaa  atatctacat    780
gagcattgca atcccaccagt catccataga gatctgaaat catctaatat acttttggat    840
ttggacttca atgcaaagct ttcagatttt ggtcttgcag taactgatgc ggcaacaaac    900
aagaataact tgaagctttc gggtacttta ggttatctag ctccagaata cctttttagat    960
ggtaaattaa cagataagag tgatgtttat gcattcggtg ttgtgctgct cgaacttcta   1020
ttgggacgaa aggctgttga aaaattatca caactcagtg ccaatcttag gtccatttgg   1080
gcatag                                                               1086

SEQ ID NO: 82              moltype = AA   length = 361
FEATURE                    Location/Qualifiers
source                     1..361
                           mol_type = protein
                           organism = Gossypium sp.
SEQUENCE: 82
MKKKLVLHLL LFLVCALENI VLAVQGPASS PISTPISASM AAFSPAGIQL GGEEHKKMDP     60
TKKMLLALIL ACSSLGAIIS SLFCLWIYYR KNSSKSSKNG AKSSDGEKGN GLAPYLGKFK    120
SMRTVSKEGY ASFMDYKILE KATNKFHHGN ILGEGGFGCV YKAQFNDGSY AAVKKLDCAS    180
QDAEKEYENE VGLLCRFKHS NIISLLGYSS DNDTRFIVYE LMENGSLETQ LHGPSHGSSL    240
TWHRRMKIAL DTARGLEYLH EHCNPPVIHR DLKSSNILLD LDFNAKLSDF GLAVTDAATN    300
KNNLKLSGTL GYLAPEYLLD GKLTDKSDVY AFGVVLLELL LGRKAVEKLS QLSANLRSIW    360
A                                                                    361

SEQ ID NO: 83              moltype = DNA   length = 1089
FEATURE                    Location/Qualifiers
variation                  1024
                           note = n is a, c, g, or t
source                     1..1089
                           mol_type = genomic DNA
                           organism = Solanum lycopersicum
SEQUENCE: 83
ggagtgggaa ttgagaagca gccacccacc cacccaccct atggataaaa atagaaggct      60
gttgatagca ctcattgtag cttctactgc attaggacta atctttatct tcatcatttt    120
attctgatt  tttcacaaaa gatttcacac ctcagatgtt gtgaagggaa tgagtaggaa    180
aacattggtt tctttaatgg actacaacat acttgaatca gccaccaaca aatttaaaga    240
aactgagatt ttaggtgagg gggttttga  atgtgtgtac aaagctaaat tggaagacaa    300
ttttatgta  gctgtcaaga aactaaccca aaattccatt aaagaatttg agactgagtt    360
agagttgttg agtcaaatgc aacatcccaa tattatttca ttgttgggat attgcatcca    420
cagtgaaaca agattgcttg tctatgaact catgcaaaat ggatcactag aaactcaatt    480
acatgggcct tcccgtggat cagcattaac ttggcatcgc aggataaaaa ttgcccttga    540
tgcagcaaga ggaatagaat atttacatga gcagcgccat ccccctgtaa ttcatagaga    600
tctgaaatca tctaatattc ttttagattc caacttcaat gcaaaggtaa aacttttat     660
gtagaaatta tactaggact agttttccct ctattaatct tgtgttgtga ttaatttag     720
ctgtcagatt ttggtcttgc tgtgttgagt ggggctcaaa acaaaaacaa tatcaagctt    780
tctgaaacta taggttatgt agcgcctgaa tacatgttag atggaaaatt aagtgataaa    840
agtgatgttt atggttttgg agtagtactt tggagctgt  tattgggaag gcggcctgta    900
gaaaaggagg cagccactga atgtcagtct atagtgacat gggccatgcc tcagctgaca    960
gatagatcaa agcttccaaa cattgttgat cctgtcatac aaaacacaat ggatttaaag   1020
catntgtatc aggttgctgc aggtgctcta ttatgtgttc agccagagcc aagctatcgt   1080
cccgtataa                                                            1089

SEQ ID NO: 84              moltype = DNA   length = 875
FEATURE                    Location/Qualifiers
source                     1..875
                           mol_type = genomic DNA
                           organism = Aquilegia sp.
SEQUENCE: 84
gagtatcagt tattgaagc  tgcaactgac aatttagtg agagtaatat tttgggagaa      60
ggtggatttg gatgtgttta caaagcatgt tttgataaca acttttctcgc tgctgtcaag    120
```

-continued

```
agaatggatg ttggtgggca agatgcagaa agagaatttg agaaagaagt agatttgttg  180
aatagaattc agcatccgga tataatttcc ctgttgggtt attgtattca tgatgagaca  240
aggttcatca tttatgaact aatgcagaac ggatctttgg aaagacaatt acatggacct  300
tctcatggat cggctttaac ttggcatatc cggatgaaaa ttgcacttga tacagcaaga  360
gcattagaat atctccatga gaattgcaac cctcctgtga tccacagaga tctgaaatca  420
tccaatatac ttttggattc taatttcaag gccaagattt cagattttgg tcttgctgta  480
atttctggga gtcaaaacaa gaacaacatt aagctttcag gcactcttgg ttatgttgct  540
ccagaatatc tgttagatgg taaattgact gacaaaagtg atgtctatgc ttttggggtt  600
atccttctag aactcctaat gggaagaaaa cctgtagaga aaatgacacg aactcagtgt  660
caatctatcg ttacatgggc catgcctcaa ctcactgata gatcaaagct accaaacatt  720
gttgatcctg tgattaaaaa cacaatggat ttgaagcatt tgttccaagt tgctgctgta  780
gctgtactgt gtgtacaacc agaaccaagt taccggccat taatcacaga tgtccttcac  840
tccctcgtac cccttgttcc tgtcgatctt ggagg                              875

SEQ ID NO: 85          moltype = AA  length = 292
FEATURE                Location/Qualifiers
source                 1..292
                       mol_type = protein
                       organism = Aquilegia sp.
SEQUENCE: 85
EYQLLEAATD NFSESNILGE GGFGCVYKAC FDNNFLAAVK RMDVGGQDAE REFEKEVDLL  60
NRIQHPDIIS LLGYCIHDET RFIIYELMQN GSLERQLHGP SHGSALTWHI RMKIALDTAR  120
ALEYLHENCN PPVIHRDLKS SNILLDSNFK AKISDFGLAV ISGSQNKNNI KLSGTLGYVA  180
PEYLLDGKLT DKSDVYAFGV ILLELLMGRK PVEKMTRTQC QSIVTWAMPQ LTDRSKLPNI  240
VDPVIKNTMD LKHLFQVAAV AVLCVQPEPS YRPLITDVLH SLVPLVPVDL GG          292

SEQ ID NO: 86          moltype = DNA  length = 696
FEATURE                Location/Qualifiers
source                 1..696
                       mol_type = genomic DNA
                       organism = Centaurea maculosa
SEQUENCE: 86
tgtgctcatg atgagaccaa actacttgtt tacgaactta tgcacaatgg ttcgttagaa  60
actcaattac acggtccttc ttgtggatcc aatttaacat ggcattgtcg gatgaaaatt  120
gcgctagata tagcgagagg attggaatat ttacatgaac actgcaaacc atctgtgatt  180
catagagatt tgaagtcatc taacatcctt ttggattcaa aattcaatgc caagctttcg  240
gatttcggtc ttgctgtgat gaacggtgcc aataccaaaa acattaagct ttcggggacg  300
ttgggttacg tagctcccga gtatctttta aatgggaaat tgaccgataa aagtgacgtc  360
tacgcattcg gagttgtact tttagagctt ctactcaaaa ggcggcctgt cgaaaaacta  420
gcaccatccg agtgccagtc catcgtcact tgggctatgc cgcaactaac agacagaaca  480
aagcttccga gtgttataga tcccgtgatc agggacacga tggatcttaa acacttgtat  540
caagtggcgg ctgtggctgt gttgtgtgtt caaccggaac cgggataccg gccgttgata  600
accgacgtct tgcattctct ggttcctctc gtgccggttg aactcggagg gactctacga  660
gttgcggaaa caggttgcgg cacagttgac ttatga                             696

SEQ ID NO: 87          moltype = AA  length = 231
FEATURE                Location/Qualifiers
source                 1..231
                       mol_type = protein
                       organism = Centaurea maculosa
SEQUENCE: 87
CAHDETKLLV YELMHNGSLE TQLHGPSCGS NLTWHCRMKI ALDIARGLEY LHEHCKPSVI  60
HRDLKSSNIL LDSKFNAKLS DFGLAVMNGA NTKNIKLSGT LGYVAPEYLL NGKLTDKSDV  120
YAFGVVLLEL LLKRRPVEKL APSECQSIVT WAMPQLTDRT KLPSVIDPVI RDTMDLKHLY  180
QVAAVAVLCV QPEPGYRPLI TDVLHSLVPL VPVELGGTLR VAETGCGTVD L            231

SEQ ID NO: 88          moltype = DNA  length = 842
FEATURE                Location/Qualifiers
source                 1..842
                       mol_type = genomic DNA
                       organism = Cichorium intybus
SEQUENCE: 88
tggatttgga tgcgtttaaa agctcaactc aatgataact tattagttgc ggtcaaacga  60
ctagacaata aaagtcaaaa ttccatcaaa gaattccaga cggaagtgaa tattttgagt  120
aaaattcaac atccaaatat aattagtttg ttgggatatt gcgatcatga tgaaagcaag  180
ctacttgttt acgaattgat gcaaaatggt tctttagaaa ctcagttaca tgggccttct  240
tgtggatcca atttaacatg gtattgccgg atgaaaattg ccctagatat agcaagagga  300
ttggaatatt tacatgaaca ctccaaacca tctgtgattc atagagatct caaatcatct  360
aatatacttc ttgattcaaa tttcaatgca aagctttcgg attttggtct tgcggtgatg  420
gaaggtgcaa atagcaaaaa cattaaactt tcggggacat tgggatacgt agcacccgaa  480
tatcttttag atgggaaatt aaccgataaa agtgacgtgt atgcatttgg agtcgtactt  540
tttgagcttt tactcagaag acgacacgtt gaaaaactag aatcatcaca atcccgccaa  600
tctattgtca cttgggcgat gccactacta atggacagat cgaagcttcc gagtgtgata  660
gatcctgtga ttagggatac aatggatctt aaacatcttt atcaagtggc tgcggtggcg  720
gtgttgtgtg ttcaatcgga accgagttac cgtccgttga taaccgatgt tttacattct  780
cttgttcctc ttgtcccggt tgaacttgga gggacactta gagttgtaga aaagagtgtt  840
gt                                                                  842

SEQ ID NO: 89          moltype = AA  length = 281
```

```
FEATURE                  Location/Qualifiers
source                   1..281
                         mol_type = protein
                         organism = Cichorium intybus
SEQUENCE: 89
WIWMRLKAQL NDNLLVAVKR LDNKSQNSIK EFQTEVNILS KIQHPNIISL LGYCDHDESK    60
LLVYELMQNG SLETQLHGPS CGSNLTWYCR MKIALDIARG LEYLHEHSKP SVIHRDLKSS   120
NILLLDSNFNA KLSDFGLAVM EGANSKNIKL SGTLGYVAPE YLLDGKLTDK SDVYAFGVVL  180
FELLLRRRHV EKLESSQSRQ SIVTWAMPLL MDRSKLPSVI DPVIRDTMDL KHLYQVAAVA   240
VLCVQSEPSY RPLITDVLHS LVPLVPVELG GTLRVVEKSV V                      281

SEQ ID NO: 90            moltype = DNA  length = 495
FEATURE                  Location/Qualifiers
source                   1..495
                         mol_type = genomic DNA
                         organism = Cucumis melo
SEQUENCE: 90
attcttttag atgcaaactt caatgccaag ctttctgatt ttggcttgtc tgtcattgtt    60
ggagcacaaa acaagaatga tataaagctt tccggaacga tgggttatgt tgctcctgaa   120
tatcttttag atggtaaatt gactgataaa agtgatgtct atgcttttgg agttgtgctt   180
ttggagcttc ttttaggaag aaggcctgtt gaaaaactgg caccatctca atgtcaatcc   240
attgtcacat gggctatgcc tcaactcact gatagatcaa agttacccga tcgttgat    300
ccggtgatca gacacacaat ggaccctaaa catttatttc aggttgctgc tgtcgccgtg   360
ctgtgtgtgc aaccgaaacc gagctatcgt ccctaataa cagatctttt gcactctctt   420
attcctcttg ttcctgttga gctaggaggt actcacagat catcaacatc acaagctcct   480
gtggctccag cttag                                                   495

SEQ ID NO: 91            moltype = AA  length = 164
FEATURE                  Location/Qualifiers
source                   1..164
                         mol_type = protein
                         organism = Cucumis melo
SEQUENCE: 91
ILLDANFNAK LSDFGLSVIV GAQNKNDIKL SGTMGYVAPE YLLDGKLTDK SDVYAFGVVL    60
LELLLGRRPV EKLAPSQCQS IVTWAMPQLT DRSKLPDIVD PVIRHTMDPK HLFQVAAVAV   120
LCVQPEPSYR PLITDLLHSL IPLVPVELGG THRSSTSQAP VAPA                    164

SEQ ID NO: 92            moltype = DNA  length = 375
FEATURE                  Location/Qualifiers
source                   1..375
                         mol_type = genomic DNA
                         organism = Eragrostis curvula
SEQUENCE: 92
gatgggaagc tcaccgagaa aagcgacgtg tacgcgtttg gcatagtgct tcttgagctg    60
ctaatgggaa ggaagcctgt tgagaagttg agtcaatctc agtgccaatc aattgtgact   120
tgggccatgc cccaactgac agacagatca aaacttccca acataattga cccagtgatc   180
agggacacaa tggatccaaa gcacttgtat caggttgctg cagttgctgt tctatgcgtg   240
caaccagaac cgagttacag accactgata acgatgtgtc tccactcttt agttcctcta   300
gtgcctgtgg agcttggtgg gacactaagg gttgcagagc caccgtcccc aaaccaaaat   360
cattctcctc gttga                                                   375

SEQ ID NO: 93            moltype = AA  length = 124
FEATURE                  Location/Qualifiers
source                   1..124
                         mol_type = protein
                         organism = Eragrostis curvula
SEQUENCE: 93
DGKLTEKSDV YAFGIVLLEL LMGRKPVEKL SQSQCQSIVT WAMPQLTDRS KLPNIIDPVI    60
RDTMDPKHLY QVAAVAVLCV QPEPSYRPLI TDVLHSLVPL VPVELGGTLR VAEPPSPNQN   120
HSPR                                                                124

SEQ ID NO: 94            moltype = DNA  length = 414
FEATURE                  Location/Qualifiers
source                   1..414
                         mol_type = genomic DNA
                         organism = Gerbera hybrid
SEQUENCE: 94
ggggttcatg gcaagaacaa tataaaactt tcaggaactt taggatatgt cgcgccggaa    60
taccttttag atggtaaact tactgataaa agtgacgttt atgcgtttgg agttgtgctt   120
ctcgagcttt tgataggacg aaaacccgtg gagaaaatgt caccatttca atgccaattt   180
atcgttacat gggcaatgcc tcagctaacg gacagatcga agcttcctaa tcttgtggat   240
cctgtgatta gagatactat ggacttgaag cccttatatc aagttgcggc tgtaactgtg   300
ttatgtgtac aacccgaacc aagttaccgc ccattaataa cggatgtttt gcattcgttc   360
atcccacttg tacctgctga tcttggaggg tcgttaaaag ttgtcgactt ttaa         414

SEQ ID NO: 95            moltype = AA  length = 137
FEATURE                  Location/Qualifiers
source                   1..137
                         mol_type = protein
```

```
                        organism = Gerbera hybrid
SEQUENCE: 95
GVHGKNNIKL SGTLGYVAPE YLLDGKLTDK SDVYAFGVVL LELLIGRKPV EKMSPFQCQF    60
IVTWAMPQLT DRSKLPNLVD PVIRDTMDLK PLYQVAAVTV LCVQPEPSYR PLITDVLHSF  120
IPLVPADLGG SLKVVDF                                                 137

SEQ ID NO: 96           moltype = DNA   length = 498
FEATURE                 Location/Qualifiers
source                  1..498
                        mol_type = genomic DNA
                        organism = Helianthus paradoxus
SEQUENCE: 96
atcgtgttcc attttggttg ttgtctaaag ctttcagatt ttggtcttgc tgtaatggat    60
ggagcccaga acaaaaacaa catcaagctt tcagggacat tgggttatgt agctccagag  120
tatcttttag atggaaaact gaccgacaaa agtgatgtat atgcatttgg agttgtactt  180
ttagagcttc tacttggaag acggcctgta gaaaaactgg ccgcatctca atgccaatct  240
atcgtcactt gggccatgcc acagctaaca gacagatcaa agctcccaaa tattgtcgat  300
cctgtaatca gatatacgat ggatctcaaa cacttgtacc aagttgctgc cgtggcagtg  360
ctgtgtgtgc aaccagagcc aagttaccgg ccattaataa ccgatgtttt gcattctctt  420
atccctcttg ttccggtgga gctcggggga actctaaaag ctccacaaac aaggtcttcg  480
gtaacaaatg acccgtga                                                 498

SEQ ID NO: 97           moltype = AA    length = 165
FEATURE                 Location/Qualifiers
source                  1..165
                        mol_type = protein
                        organism = Helianthus paradoxus
SEQUENCE: 97
IVFHFGCCLK LSDFGLAVMD GAQNKNNIKL SGTLGYVAPE YLLDGKLTDK SDVYAFGVVL    60
LELLLGRRPV EKLAASQCQS IVTWAMPQLT DRSKLPNIVD PVIRYTMDLK HLYQVAAVAV  120
LCVQPEPSYR PLITDVLHSL IPLVPVELGG TLKAPQTRSS VTNDP                  165

SEQ ID NO: 98           moltype = DNA   length = 612
FEATURE                 Location/Qualifiers
source                  1..612
                        mol_type = genomic DNA
                        organism = Ipomoea nil
SEQUENCE: 98
cgtggatcaa ctttaagttg gcctctccga atgaaaattg ctttggatat tgcaagagga    60
ttagaatacc ttcacgagcg ttgcaacccc cctgtgatcc ataggcatct caaatcgtct  120
aatattcttc ttgattccag cttcaacgca aagatttctg attttggcct ttctgtaact  180
ggcggaaacc taagcaagaa cataaccaag atttcgggat cactgggtta tcttgctcca  240
gagtatctct tagacggtaa actaactgat aagagtgatg tgtatggttt tggcattatt  300
cttctagagc ttttgatggg taaaaggcca gtgagaaaag tgggagaaac taagtgccaa  360
tcaatagtta catgggctat gccccagctt acgaccgat caaagcttcc gaatattgtt   420
gaccctacga tcaggaacac aatggatgtt aagcatttat atcaggttgc ggctgtagct  480
gtgttatgtg tgcaaccgga gccaagctat aggccattga taactgatgt actacactcc  540
ttcattccac ttgtaccaaa tgaactcggg gggtcgctta gggtagtgga ttctactccc  600
cattgctcat ag                                                       612

SEQ ID NO: 99           moltype = AA    length = 203
FEATURE                 Location/Qualifiers
source                  1..203
                        mol_type = protein
                        organism = Ipomoea nil
SEQUENCE: 99
RGSTLSWPLR MKIALDIARG LEYLHERCNP PVIHRHLKSS NILLDSSFNA KISDFGLSVT    60
GGNLSKNITK ISGSLGYLAP EYLLDGKLTD KSDVYGFGII LLELLMGKRP VEKVGETKCQ  120
SIVTWAMPQL TDRSKLPNIV DPTIRNTMDV KHLYQVAAVA VLCVQPEPSY RPLITDVLHS  180
FIPLVPNELG GSLRVVDSTP HCS                                          203

SEQ ID NO: 100          moltype = DNA   length = 708
FEATURE                 Location/Qualifiers
source                  1..708
                        mol_type = genomic DNA
                        organism = Nuphar advena
SEQUENCE: 100
ttagataatg gcggaccga ttgtcaacga gaattcgaga atgaggttga tttgatgagt     60
agaattaggc atccaaatgt ggtttcttta ttgggttatt gcattcatgg agaaaccagg  120
cttcttgtct atgaaatgat gcaaaacggg acgttggaat cgctattgca tggaccatca  180
catggatcct cactaacttg gcacattcgt atgaagatcg ccctcgacac agcaagaggc  240
ctcgagtatc tgcatgaaca ctgcgacccc tctgtgatcc accgtgacct gaagccttct  300
aacattcttt tggattccaa ctacaattcc aagctccag actttggtct tgcagtcact  360
gttggaagcc agaatcaaac caacattaag attctaggga cactgggtta ccttgcacca  420
gagtacgttt tgaatggcaa attgacagag aaaagtgatg tgtttgcttt tggagttgtc  480
ctgttggagc ttctcatggg caagaaacca gtgagaagaa tggcatcccc tccatgccaa  540
tccattgtca catgggcgat gcctcatctt actgacagaa ttaagcttcc aaatatcatt  600
gatcctgtta ttagaaacac catggatctg aaacacttgt accaggttgc agctgttgct  660
gttctctgcg tacaaccaga gccccagtta cgtcctctg ataactga                708
```

```
SEQ ID NO: 101          moltype = AA   length = 235
FEATURE                 Location/Qualifiers
source                  1..235
                        mol_type = protein
                        organism = Nuphar advena
SEQUENCE: 101
LDNGGPDCQR EFENEVDLMS RIRHPNVVSL LGYCIHGETR LLVYEMMQNG TLESLLHGPS   60
HGSSLTWHIR MKIALDTARG LEYLHEHCDP SVIHRDLKPS NILLDSNYNS KLSDFGLAVT  120
VGSQNQTNIK ILGTLGYLAP EYVLNGKLTE KSDVFAFGVV LLELLMGKKP VEKMASPPCQ  180
SIVTWAMPHL TDRIKLPNII DPVIRNTMDL KHLYQVAAVA VLCVQPEPQL SSSDN       235

SEQ ID NO: 102          moltype = DNA  length = 30
FEATURE                 Location/Qualifiers
source                  1..30
                        mol_type = other DNA
                        organism = synthetic construct
SEQUENCE: 102
tcggctcggc ccagaacaag atcgcaagac                                    30

SEQ ID NO: 103          moltype = DNA  length = 34
FEATURE                 Location/Qualifiers
source                  1..34
                        mol_type = other DNA
                        organism = synthetic construct
SEQUENCE: 103
ctacattctc tcctcgtatt attcctcgtt gact                               34

SEQ ID NO: 104          moltype = DNA  length = 32
FEATURE                 Location/Qualifiers
source                  1..32
                        mol_type = other DNA
                        organism = synthetic construct
SEQUENCE: 104
actttcagat gagtggatca taaccctata ca                                 32

SEQ ID NO: 105          moltype = DNA  length = 31
FEATURE                 Location/Qualifiers
source                  1..31
                        mol_type = other DNA
                        organism = synthetic construct
SEQUENCE: 105
agatacaatg gatctcaaac acttatacca g                                  31

SEQ ID NO: 106          moltype = DNA  length = 42
FEATURE                 Location/Qualifiers
source                  1..42
                        mol_type = other DNA
                        organism = synthetic construct
SEQUENCE: 106
aaaggatcca tgggaagtgg tgaagaagat agatttgatg ct                      42

SEQ ID NO: 107          moltype = DNA  length = 40
FEATURE                 Location/Qualifiers
source                  1..40
                        mol_type = other DNA
                        organism = synthetic construct
SEQUENCE: 107
tttctgcagt ctgtgaatca tcttgttaac cggagagtcc                         40

SEQ ID NO: 108          moltype = DNA  length = 30
FEATURE                 Location/Qualifiers
source                  1..30
                        mol_type = other DNA
                        organism = synthetic construct
SEQUENCE: 108
tctgagtttt aatcgagcca agtcgtctca                                    30

SEQ ID NO: 109          moltype = DNA  length = 53
FEATURE                 Location/Qualifiers
source                  1..53
                        mol_type = other DNA
                        organism = synthetic construct
SEQUENCE: 109
tatcccggga aaatgagaga gcttcttctt cttcttcttc ttcatttttca gtc         53

SEQ ID NO: 110          moltype = DNA  length = 38
FEATURE                 Location/Qualifiers
source                  1..38
```

```
                        mol_type = other DNA
                        organism = synthetic construct
SEQUENCE: 110
tttggatcct gtgaatcatc ttgttaaccg gagagtcc                              38

SEQ ID NO: 111          moltype = DNA  length = 41
FEATURE                 Location/Qualifiers
source                  1..41
                        mol_type = other DNA
                        organism = synthetic construct
SEQUENCE: 111
atacccgggt ctgtgtcagg aatccaaatg ggaagtggtg a                          41

SEQ ID NO: 112          moltype = DNA  length = 41
FEATURE                 Location/Qualifiers
source                  1..41
                        mol_type = other DNA
                        organism = synthetic construct
SEQUENCE: 112
aaaggatcct ctgtgtcagg aatccaaatg ggaagtggtg a                          41

SEQ ID NO: 113          moltype = DNA  length = 39
FEATURE                 Location/Qualifiers
source                  1..39
                        mol_type = other DNA
                        organism = synthetic construct
SEQUENCE: 113
aaatctagac tgtgaatcat cttgttaacc ggagagtcc                             39

SEQ ID NO: 114          moltype = DNA  length = 35
FEATURE                 Location/Qualifiers
source                  1..35
                        mol_type = other DNA
                        organism = synthetic construct
SEQUENCE: 114
atagagctcg caagaaccaa tctccaaaat ccatc                                 35

SEQ ID NO: 115          moltype = DNA  length = 37
FEATURE                 Location/Qualifiers
source                  1..37
                        mol_type = other DNA
                        organism = synthetic construct
SEQUENCE: 115
atagagctcg agggtcttga tatcgaaaaa ttgcacg                               37

SEQ ID NO: 116          moltype = DNA  length = 37
FEATURE                 Location/Qualifiers
source                  1..37
                        mol_type = other DNA
                        organism = synthetic construct
SEQUENCE: 116
ataggatcct cgcaagaacc aatctccaaa atccatc                               37

SEQ ID NO: 117          moltype = DNA  length = 40
FEATURE                 Location/Qualifiers
source                  1..40
                        mol_type = other DNA
                        organism = synthetic construct
SEQUENCE: 117
atatctagac tcgagggtct tgatatcgaa aaattgcacg                            40

SEQ ID NO: 118          moltype = DNA  length = 52
FEATURE                 Location/Qualifiers
source                  1..52
                        mol_type = other DNA
                        organism = synthetic construct
SEQUENCE: 118
atatctagaa aatgagagag cttcttcttc ttcttcttct tcattttcag tc              52

SEQ ID NO: 119          moltype = DNA  length = 47
FEATURE                 Location/Qualifiers
source                  1..47
                        mol_type = other DNA
                        organism = synthetic construct
SEQUENCE: 119
ataggatcct gttaaaagcg atttataatt tacaccgttt tggtgta                    47

SEQ ID NO: 120          moltype = DNA  length = 41
FEATURE                 Location/Qualifiers
```

|                    |                                      |      |
|--------------------|--------------------------------------|------|
| source             | 1..41                                |      |
|                    | mol_type = other DNA                 |      |
|                    | organism = synthetic construct       |      |
| SEQUENCE: 120      |                                      |      |
| atacccggga aaagttttg atgaaattca atctaaagac t | | 41 |

```
SEQ ID NO: 121          moltype = DNA   length = 1309
FEATURE                 Location/Qualifiers
source                  1..1309
                        mol_type = genomic DNA
                        organism = Arabidopsis thaliana
SEQUENCE: 121
aaaatgagag agcttcttct tcttcttctt cttcattttc agtctctaat tcttttgatg    60
atcttcatca ctgtctctgc ttcttctgct tcaaatcctt ctttagctcc tgtttactct   120
tccatggcta cattctctcc tcgaatccaa atgggaagtg gtgaagaaga tagatttgat   180
gctcataaga aacttctgat tggtctcata atcagttttct cttctcttgg ccttataatc   240
ttgttctgtt ttggcttttg ggtttatcgc aagaaccaat ctccaaaatc catcaacaac   300
tcagattctg agagtgggaa ttcatttctcc ttgttaatga gacgacttgg ctcgattaaa   360
actcagagaa gaacttctat ccaaaagggt tacgtgcaat ttttcgatat caagaccctc   420
gagaaagcga caggcggttt taagaaagt agtgtaatcg acaaggcgg tttcggatgc    480
gtttacaagg gttgtttgga caataacgtt aaagcagcgg tcaagaagat cgagaacgtt   540
agccaagaag caaaacgaga atttcagaat gaagttgcaa tgttgagcaa gatccatcac   600
tcgaacgtta tatcattgtt gggctctgca agcgaaatca actcgagttt catcgtttat   660
gagcttatgg agaaaggatc attagatgaa cagttacatg ggccttctcg tggatcagct   720
ctaacatggc acatgcgtat gaagattgct cttgatacag ctagaggact agagtatctc   780
catgagcatt gtcgtccacc agttatccac agagattga aatcttcgaa tattcttctt   840
gattcttcct tcaacgccaa gatttcagat ttcggttttg ctgtatcgct ggatgaacat   900
ggcaagaaca acattaaact ctctgggaca cttggttatg ttgccccgga atacctcctt   960
gacgaaaac tgacggataa gagtgatgtt tatgcatttg gggtagttct gcttgaactc  1020
ttgttgggta gacgaccagt tgaaaaatta actccagctc aatgccaatc tcttgtaact  1080
tgggcaatgc cacaacttac cgatagatcc aagcttccaa acattgtgga tgccgttata  1140
aaagatacaa tggatctcaa acacttattcac caggtagcag ccatggctgt gttgtgcgtg  1200
cagccagaac caagttaccg gccgttgata accgatgttc ttcactcact tgttccactg  1260
gttccggtag agctaggagg gactctccgg ttaacaagat gattcacag              1309

SEQ ID NO: 122          moltype = DNA   length = 25
FEATURE                 Location/Qualifiers
source                  1..25
                        mol_type = other DNA
                        organism = synthetic construct
SEQUENCE: 122
tcggacaagg cggtttcgga tgcgt                                           25

SEQ ID NO: 123          moltype = DNA   length = 32
FEATURE                 Location/Qualifiers
source                  1..32
                        mol_type = other DNA
                        organism = synthetic construct
SEQUENCE: 123
tagtcctcta gctgtatcaa gagcaatctt ca                                   32

SEQ ID NO: 124          moltype = DNA   length = 32
FEATURE                 Location/Qualifiers
source                  1..32
                        mol_type = other DNA
                        organism = synthetic construct
SEQUENCE: 124
tatcattgtt gggctctgca agtgaaatca ac                                   32

SEQ ID NO: 125          moltype = DNA   length = 32
FEATURE                 Location/Qualifiers
source                  1..32
                        mol_type = other DNA
                        organism = synthetic construct
SEQUENCE: 125
tggagaaagg atccttagat gatcagttac at                                   32

SEQ ID NO: 126          moltype = DNA   length = 31
FEATURE                 Location/Qualifiers
source                  1..31
                        mol_type = other DNA
                        organism = synthetic construct
SEQUENCE: 126
tccatgtaac tgatcatcta aggatccttt c                                    31

SEQ ID NO: 127          moltype = DNA   length = 37
FEATURE                 Location/Qualifiers
source                  1..37
                        mol_type = other DNA
```

```
                              organism = synthetic construct
SEQUENCE: 127
ataaacgacg aaactcgagt tgatttcact tgcagag                              37

SEQ ID NO: 128          moltype = DNA  length = 28
FEATURE                 Location/Qualifiers
source                  1..28
                        mol_type = other DNA
                        organism = synthetic construct
SEQUENCE: 128
aaaatgaaga aactggttca tcttcagt                                        28

SEQ ID NO: 129          moltype = DNA  length = 27
FEATURE                 Location/Qualifiers
source                  1..27
                        mol_type = other DNA
                        organism = synthetic construct
SEQUENCE: 129
tagacttcta ttctcacatt cttacac                                         27

SEQ ID NO: 130          moltype = DNA  length = 27
FEATURE                 Location/Qualifiers
source                  1..27
                        mol_type = other DNA
                        organism = synthetic construct
SEQUENCE: 130
tccaatgatc cattatgcat cagctca                                         27

SEQ ID NO: 131          moltype = DNA  length = 29
FEATURE                 Location/Qualifiers
source                  1..29
                        mol_type = other DNA
                        organism = synthetic construct
SEQUENCE: 131
tcgttctcaa attctctctc agcatgttg                                       29

SEQ ID NO: 132          moltype = DNA  length = 29
FEATURE                 Location/Qualifiers
source                  1..29
                        mol_type = other DNA
                        organism = synthetic construct
SEQUENCE: 132
tccggatatg ccaggtcagc gctgatcca                                       29

SEQ ID NO: 133          moltype = DNA  length = 28
FEATURE                 Location/Qualifiers
source                  1..28
                        mol_type = other DNA
                        organism = synthetic construct
SEQUENCE: 133
tccagggatc ccttctccat gagctcat                                        28

SEQ ID NO: 134          moltype = DNA  length = 41
FEATURE                 Location/Qualifiers
source                  1..41
                        mol_type = other DNA
                        organism = synthetic construct
SEQUENCE: 134
aaagagctct ctgtgtcagg aatccaaatg ggaagtggtg a                         41

SEQ ID NO: 135          moltype = DNA  length = 47
FEATURE                 Location/Qualifiers
source                  1..47
                        mol_type = other DNA
                        organism = synthetic construct
SEQUENCE: 135
atagctagct gttaaaagcg atttataatt tacaccgttt tggtgta                   47

SEQ ID NO: 136          moltype = DNA  length = 43
FEATURE                 Location/Qualifiers
source                  1..43
                        mol_type = other DNA
                        organism = synthetic construct
SEQUENCE: 136
atagctagca gaaaagtttt tgatgaaatt caatctaaag act                       43

SEQ ID NO: 137          moltype = DNA  length = 29
FEATURE                 Location/Qualifiers
source                  1..29
```

```
                        mol_type = other DNA
                        organism = synthetic construct
SEQUENCE: 137
tctgggttta tcatcatacc aagtatcca                                        29

SEQ ID NO: 138          moltype = DNA   length = 31
FEATURE                 Location/Qualifiers
source                  1..31
                        mol_type = other DNA
                        organism = synthetic construct
SEQUENCE: 138
attcagttcc atcaagattg ttggcatgga c                                     31

SEQ ID NO: 139          moltype = DNA   length = 31
FEATURE                 Location/Qualifiers
source                  1..31
                        mol_type = other DNA
                        organism = synthetic construct
SEQUENCE: 139
tggagggagg tggccctgag tgcgagaagg a                                     31

SEQ ID NO: 140          moltype = DNA   length = 27
FEATURE                 Location/Qualifiers
source                  1..27
                        mol_type = other DNA
                        organism = synthetic construct
SEQUENCE: 140
gctggatctg cttggcagga ttcggca                                          27

SEQ ID NO: 141          moltype = DNA   length = 31
FEATURE                 Location/Qualifiers
source                  1..31
                        mol_type = other DNA
                        organism = synthetic construct
SEQUENCE: 141
atatctagat gctaggttat agatccatgc a                                     31

SEQ ID NO: 142          moltype = DNA   length = 33
FEATURE                 Location/Qualifiers
source                  1..33
                        mol_type = other DNA
                        organism = synthetic construct
SEQUENCE: 142
ataggatcca ccagaactat atatacgaag gca                                   33

SEQ ID NO: 143          moltype = DNA   length = 40
FEATURE                 Location/Qualifiers
source                  1..40
                        mol_type = other DNA
                        organism = synthetic construct
SEQUENCE: 143
aggacgactt ggctcgatta aaatcacagg tcgtgatatg                            40

SEQ ID NO: 144          moltype = DNA   length = 35
FEATURE                 Location/Qualifiers
source                  1..35
                        mol_type = other DNA
                        organism = synthetic construct
SEQUENCE: 144
taatcgagcc aagtcgtcct acatatatat tccta                                 35

SEQ ID NO: 145          moltype = DNA   length = 35
FEATURE                 Location/Qualifiers
source                  1..35
                        mol_type = other DNA
                        organism = synthetic construct
SEQUENCE: 145
taatcgagcc aagtcgtcct ctcttttgta ttcca                                 35

SEQ ID NO: 146          moltype = DNA   length = 42
FEATURE                 Location/Qualifiers
source                  1..42
                        mol_type = other DNA
                        organism = synthetic construct
SEQUENCE: 146
aggacgactt ggctcgatta aaatcaaaga gaatcaatga tc                         42

SEQ ID NO: 147          moltype = DNA   length = 21
FEATURE                 Location/Qualifiers
```

```
source                  1..21
                        mol_type = other DNA
                        organism = synthetic construct
SEQUENCE: 147
gacgacttgg ctcgattaaa a                                              21

SEQ ID NO: 148          moltype = DNA  length = 399
FEATURE                 Location/Qualifiers
source                  1..399
                        mol_type = genomic DNA
                        organism = Arabidopsis thaliana
SEQUENCE: 148
tgctaggtta tagatccatg caaatatgga gtagatgtac aaacacacgc tcggacgcat     60
attacacatg ttcatacact taatactcgc tgttttgaat tgatgtttta ggaatatata    120
tgtagagaga gcttccttga gtccattcac aggtcgtgat atgattcaat tagcttccga    180
ctcattcatc caaataccga gtcgccaaaa ttcaaactag actcgttaaa tgaatgaatg    240
atgcggtaga caaattggat cattgattct ctttgattgg actgaaggga gctccctctc    300
tcttttgtat tccaatttc ttgattaatc tttcctgcac aaaaacatgc ttgatccact     360
aagtgacata tatgctgcct tcgtatatat agttctggt                           399

SEQ ID NO: 149          moltype = DNA  length = 399
FEATURE                 Location/Qualifiers
source                  1..399
                        mol_type = other DNA
                        organism = synthetic construct
SEQUENCE: 149
tgctaggtta tagatccatg caaatatgga gtagatgtac aaacacacgc tcggacgcat     60
attacacatg ttcatacact taatactcgc tgttttgaat tgatgtttta ggaatatata    120
tgtaggacga cttggctcga ttaaaatcac aggtcgtgat atgattcaat tagcttccga    180
ctcattcatc caaataccga gtcgccaaaa ttcaaactag actcgttaaa tgaatgaatg    240
atgcggtaga caaattggat cattgattct ctttgatttt aatcgagcca agtcgtcctc    300
tcttttgtat tccaatttc ttgattaatc tttcctgcac aaaaacatgc ttgatccact     360
aagtgacata tatgctgcct tcgtatatat agttctggt                           399

SEQ ID NO: 150          moltype = DNA  length = 1475
FEATURE                 Location/Qualifiers
source                  1..1475
                        mol_type = genomic DNA
                        organism = Arabidopsis thaliana
SEQUENCE: 150
cttagccaat ggatgaggat gacacgataa tgataatcaa agatcaacat ggcacgctca     60
agaccgcctt tagaagtcct ctctaaattc tttcttccga tctcctaaat atgttttgtt    120
ttggtcaaat aaattgatag gtaatactta gtgattatac tatttggttt ttgttttatc    180
attgactatt tcactttat aaatcaaata cttatcaaaa ttgttctttc cgtatgtatt     240
catatttctc aatattgtaa agatttgttt cacctaacat ctgtacccat ctttgatcat    300
tgacaaaata tatattagaa tggccttaga acgtgttagg catcttccta ctattatcat    360
attacctaat ccccaatttt attacatttt ttaatttcta aaagagcttg aatataatgt    420
catttcgaat atctctgttc atctttttt ttttctgtgc gacttctgac ccaaagcctt     480
cgacgatttt ttccaatctg aaaacttttg aataaggaac ttagtcaatg gtcaacacct    540
tgctaattaa caaagttcc attgatacaa taatgagatt tttgtacatt aacgctttca     600
tatgttttt gcgattcaac agataatctt aaaattaagt agtcctattg ataaagtctt     660
gttcaaacgt acaaactcaa tccacacaaa accttcataa aatacgatat aggaaataaa    720
gattgttttt gcgtgagaaa atactatatg aactcaaaag attttaaaac aatttgtatt    780
aatacataaa caattgttgt gatacacccg tgtaaaattt taagattgtt ttttctgaa     840
attcttcaag gaaacttata gcttaaaatc tacacttcaa atactctgtt ttaaaggcat    900
taaaaataac tgcgtttcag aaaaatattg aaatttagc tgatcttttg ctacaaattt     960
aaggaatctt ggcacctgca gaatctaaa catgttcatt aagtaatgca atagttatac    1020
aattatacat tatttgcatc atacttatat tatagtgata ttaacaaacc catgttctca    1080
gcacacttt acgtagaaaa acataaaaac ccaaatagga agaagccact caatagggata   1140
atgggtttat ataattcaca gcaaagaaag ccatcgaact attcgattaa ttatccattc    1200
tttttttttt tagtttgaat gtataagaac aaagagttgt tacgcatcat gacaatgtct    1260
tagaaaacaa aagaaatgaa taaaaaagta aaacgaaaaa taaaaagtga ggatgaagtt    1320
gttgaatgag ttggcgaggc ggcgactttt tcatacattc catttactta attcctaaag    1380
tccttctcac atctctttgt tatataatga caccataacc atttcttctc ttcacaatct    1440
ttacaagaat atctctcttc tacagtaaac aaaaa                              1475

SEQ ID NO: 151          moltype = DNA  length = 31
FEATURE                 Location/Qualifiers
source                  1..31
                        mol_type = other DNA
                        organism = synthetic construct
SEQUENCE: 151
acgtaagctt cttagccaat ggatgaggat g                                   31

SEQ ID NO: 152          moltype = DNA  length = 31
FEATURE                 Location/Qualifiers
source                  1..31
                        mol_type = other DNA
                        organism = synthetic construct
```

-continued

```
SEQUENCE: 152
acgttctaga tttttgttta ctgtagaaga g                                    31

SEQ ID NO: 153          moltype = DNA  length = 338
FEATURE                 Location/Qualifiers
source                  1..338
                        mol_type = genomic DNA
                        organism = Brassica napus
SEQUENCE: 153
tgctgcttca atccttctat tagctcctgt ttataccacc atgactactt tctctccagg     60
aattcaaatg ggaagtggtg aagaacacag attagatgca cataagaaac tcctgattgg    120
tcttataatc agttcctctt ctcttggtat cgtaatcttg atttgctttg cttctggat     180
gtactgtcgc aagaaagctc ccaaacccat caagattccg gatgctgaga gtgggacttc    240
atcattttca atgtttgtga ggcggctaag ctcaatcaaa actcagagaa catctagcaa    300
tcagggttat gtgcagcgtt tcgattccaa gacgctag                            338

SEQ ID NO: 154          moltype = DNA  length = 38
FEATURE                 Location/Qualifiers
source                  1..38
                        mol_type = other DNA
                        organism = synthetic construct
SEQUENCE: 154
tatggatcct gctgcttcaa atccttctat agctcctg                             38

SEQ ID NO: 155          moltype = DNA  length = 37
FEATURE                 Location/Qualifiers
source                  1..37
                        mol_type = other DNA
                        organism = synthetic construct
SEQUENCE: 155
tattctagac tagcgtcttg gaatcgaaac gctgcac                              37

SEQ ID NO: 156          moltype = DNA  length = 38
FEATURE                 Location/Qualifiers
source                  1..38
                        mol_type = other DNA
                        organism = synthetic construct
SEQUENCE: 156
tatgagctct gctgcttcaa atccttctat agctcctg                             38

SEQ ID NO: 157          moltype = DNA  length = 37
FEATURE                 Location/Qualifiers
source                  1..37
                        mol_type = other DNA
                        organism = synthetic construct
SEQUENCE: 157
tatgagctcc tagcgtcttg gaatcgaaac gctgcac                              37

SEQ ID NO: 158          moltype = DNA  length = 24
FEATURE                 Location/Qualifiers
source                  1..24
                        mol_type = other DNA
                        organism = synthetic construct
SEQUENCE: 158
gcagatcgct cctcccgtcg tgat                                            24

SEQ ID NO: 159          moltype = DNA  length = 28
FEATURE                 Location/Qualifiers
source                  1..28
                        mol_type = other DNA
                        organism = synthetic construct
SEQUENCE: 159
cgcctaggag cgacgggtac tcgatcat                                        28

SEQ ID NO: 160          moltype = DNA  length = 28
FEATURE                 Location/Qualifiers
source                  1..28
                        mol_type = other DNA
                        organism = synthetic construct
SEQUENCE: 160
cctagctaag cgacgggtac tcgatcat                                        28

SEQ ID NO: 161          moltype = DNA  length = 272
FEATURE                 Location/Qualifiers
source                  1..272
                        mol_type = genomic DNA
                        organism = Brachypodium distachyon
SEQUENCE: 161
gctcctcccg tcgtgatcac agtggtgagg caccaccatt accaccggga gctggtcatc     60
```

```
tccgctgtcc tcgcctgcgt cgccaccgcc atgatcctcc tctccacact ctacgcctgg    120
acgatgtggc ggcggtctcg ccggacccc cacggcggca agggccgcgg ccggagatca     180
gggatcacac tggtgccaat cctgagcaag ttcaattcag tgaagatgag caggaagggg    240
ggccttgtga cgatgatcga gtacccgtcg ct                                  272

SEQ ID NO: 162         moltype = DNA  length = 31
FEATURE                Location/Qualifiers
source                 1..31
                       mol_type = other DNA
                       organism = synthetic construct
SEQUENCE: 162
cgggatcccg gcataacaaa ctcgtgcatc c                                   31

SEQ ID NO: 163         moltype = DNA  length = 30
FEATURE                Location/Qualifiers
source                 1..30
                       mol_type = other DNA
                       organism = synthetic construct
SEQUENCE: 163
ccatcgatgg cgccaaacac aatagctcaa                                     30

SEQ ID NO: 164         moltype = DNA  length = 1174
FEATURE                Location/Qualifiers
source                 1..1174
                       mol_type = genomic DNA
                       organism = Brachypodium distachyon
SEQUENCE: 164
gtaagtaatt tcaagtttaa gtttcataag cataacaaac tcgtgcatcc aatttgaacc    60
atttactgt cctggcatcc tctaaatatt tccttgatta tcagcttatc ttcatcccat    120
tgaatcagaa aattaccaac ccttgtttta gctttaatca ttgttatttg ttgtctgagg    180
ggctacactg tttctttata ttggtgaagg agttaccagg caaaaattcc cacctcctga    240
tattagcaga gaccccctt tttgtgcctg tatgcatact aacaaataat acagatggaa    300
atatgtatat ttgttatatc atggattgat gctttatgtt tagcaagtcc atgcaatggt    360
agtcaaaaga tgtaaacttt tgaatgatat atttgggct tagattagcc atttttaccc    420
tcacttgaaa atgacaattt tgcccttccg atctactttc tcttgtcacc tcaggcaggc    480
tcttgaaagt tcttatccct gaattccgtg gaagtttatt attctaatgt tatagtttac    540
ttaaagtgtc gcataatcta ctagagccta atggaagtac tgatggactt tgttttgcta    600
caatcactgc ttgcaagaat gactactttg gggcatttct aatatattat tgatatttct    660
atgatgtatt gttgtccatg tacttcagtc cttacagcga ctagtcctat ttctgcattg    720
ataaattgtt cactgtcaga ccatcttgag tggcaagaat gagtataaca tgtcttgttt    780
ttctgtgatt tcaaggtaag cgcacatgcg cacagtgtac accgtcacca catgtgagta    840
cacccctag tacacatgta aaaaagcac agtccagtta ttaaatggac cattggcatt     900
gattgcgtg tttataggag taaagataca tgtaaacact aattcattgg gagatataaa    960
tttatactac cattgaatgt gacataggct ctaaggtttt tagttcagca tttcgaaaga    1020
gctttgtttg gttggcttgg gatggaatca ggtgacaaca ttttgggtt gcagcaaatt    1080
taatattgat tgaggaggca tacaacgaaa tcattgagct attgtgtttg gcgttacatc    1140
tatggaattt cttctaatct gattattgtt tgta                                1174

SEQ ID NO: 165         moltype = DNA  length = 22
FEATURE                Location/Qualifiers
source                 1..22
                       mol_type = other DNA
                       organism = synthetic construct
SEQUENCE: 165
gatccgctcc tcccgtcgtg at                                             22

SEQ ID NO: 166         moltype = DNA  length = 30
FEATURE                Location/Qualifiers
source                 1..30
                       mol_type = other DNA
                       organism = synthetic construct
SEQUENCE: 166
aacgcgatcg cttgcatgcc tgcagtagac                                     30

SEQ ID NO: 167         moltype = DNA  length = 28
FEATURE                Location/Qualifiers
source                 1..28
                       mol_type = other DNA
                       organism = synthetic construct
SEQUENCE: 167
gacttaatta agaattcgag ctcgggta                                       28

SEQ ID NO: 168         moltype = DNA  length = 251
FEATURE                Location/Qualifiers
source                 1..251
                       mol_type = genomic DNA
                       organism = Panicum virgatum
SEQUENCE: 168
tcgtagtgca ccaccatttc caccgcgagc tggtcatcgc cgccgtcctc gcctgcatcg    60
```

```
ccaccgtcac gatcttcctt tccacgctct acgcttggac actatggcgg cgatctcgcc    120
ggagcaccgg cggcaaggtc accaggagct cagacgcagc gaaggggatc aagctggtgc    180
cgatcttgag caggttcaac tcggtgaaga tgagcaggaa gaggctggtt gggatgttcg    240
agtacccgtc g                                                         251

SEQ ID NO: 169          moltype = DNA   length = 27
FEATURE                 Location/Qualifiers
source                  1..27
                        mol_type = other DNA
                        organism = synthetic construct
SEQUENCE: 169
gcagatctcg tagtgcacca ccatttc                                         27

SEQ ID NO: 170          moltype = DNA   length = 27
FEATURE                 Location/Qualifiers
source                  1..27
                        mol_type = other DNA
                        organism = synthetic construct
SEQUENCE: 170
cgcctaggcg acgggtactc gaacatc                                         27

SEQ ID NO: 171          moltype = DNA   length = 27
FEATURE                 Location/Qualifiers
source                  1..27
                        mol_type = other DNA
                        organism = synthetic construct
SEQUENCE: 171
cctagctacg acgggtactc gaacatc                                         27

SEQ ID NO: 172          moltype = DNA   length = 25
FEATURE                 Location/Qualifiers
source                  1..25
                        mol_type = other DNA
                        organism = synthetic construct
SEQUENCE: 172
gatcctcgta gtgcaccacc atttc                                           25

SEQ ID NO: 173          moltype = DNA   length = 21
FEATURE                 Location/Qualifiers
source                  1..21
                        mol_type = other DNA
                        organism = synthetic construct
SEQUENCE: 173
ctcgtagtgc accaccattt c                                               21

SEQ ID NO: 174          moltype = DNA   length = 261
FEATURE                 Location/Qualifiers
source                  1..261
                        mol_type = genomic DNA
                        organism = Sorghum bicolor
SEQUENCE: 174
aatgggaccg cctccgttgc tccggcggtg ccggcgccgc ctcccgtcgt gatcatcgtg     60
gagcggcgcc atcatttcca ccgcgagcta gtcatcgcct ccgttctcgc ctccatcgcc    120
atcgtcgcga ttatcctctc cacgctctat gcgtggatcc tgtggcggcg gtctcgccgg    180
ctgcccagcg gcaagggcgc caggagcgca gacaccgcga ggggaatcat gctggtgccg    240
atcctgagca agttccactc a                                              261

SEQ ID NO: 175          moltype = DNA   length = 26
FEATURE                 Location/Qualifiers
source                  1..26
                        mol_type = other DNA
                        organism = synthetic construct
SEQUENCE: 175
gcagatcaat gggaccgcct ccgttg                                          26

SEQ ID NO: 176          moltype = DNA   length = 28
FEATURE                 Location/Qualifiers
source                  1..28
                        mol_type = other DNA
                        organism = synthetic construct
SEQUENCE: 176
cgcctaggtg agtggaactt gctcagga                                        28

SEQ ID NO: 177          moltype = DNA   length = 28
FEATURE                 Location/Qualifiers
source                  1..28
                        mol_type = other DNA
                        organism = synthetic construct
SEQUENCE: 177
```

```
cctagctatg agtggaactt gctcagga                                              28

SEQ ID NO: 178          moltype = DNA   length = 273
FEATURE                 Location/Qualifiers
source                  1..273
                        mol_type = genomic DNA
                        organism = Sorghum bicolor
SEQUENCE: 178
gtaagtattc ttgcaacaca ttactatttt caataaccac aagttttaaaa gcttgagtcc          60
atttcgcaaa ccagttgttc ataaccaaat tcttaggtaa ttaggtccaa ttgagaaaat          120
ctgatcattg aacactagca ggaaataact cagacatagt ttctgcatac tataatgatg          180
cttaatatat ttgttctctt ttgagattgt attgcataga catttctgtg taaaataatg          240
ttttacatca tgtatatata tcacttttta tag                                        273

SEQ ID NO: 179          moltype = DNA   length = 30
FEATURE                 Location/Qualifiers
source                  1..30
                        mol_type = other DNA
                        organism = synthetic construct
SEQUENCE: 179
cgggatcctt cttgcaacac attactattt                                            30

SEQ ID NO: 180          moltype = DNA   length = 34
FEATURE                 Location/Qualifiers
source                  1..34
                        mol_type = other DNA
                        organism = synthetic construct
SEQUENCE: 180
ccatcgatga aatgtctatg caatacaatc tcaa                                       34

SEQ ID NO: 181          moltype = DNA   length = 24
FEATURE                 Location/Qualifiers
source                  1..24
                        mol_type = other DNA
                        organism = synthetic construct
SEQUENCE: 181
gatccaatgg gaccgcctcc gttg                                                  24

SEQ ID NO: 182          moltype = DNA   length = 21
FEATURE                 Location/Qualifiers
source                  1..21
                        mol_type = other DNA
                        organism = synthetic construct
SEQUENCE: 182
caatgggacc gcctccgttg a                                                     21

SEQ ID NO: 183          moltype = DNA   length = 1000
FEATURE                 Location/Qualifiers
source                  1..1000
                        mol_type = genomic DNA
                        organism = Sorghum bicolor
SEQUENCE: 183
ggccccggcc gcgcgcgtct ccgtgtcctc cgcgactgtg cacgtttcgt cgggagcggc          60
gtgcccacgc ccaccccccg tccaccagcc agcaaccgac ggcactggtg acacgcggct         120
ggtccgctcg gtccgcccg cggctccaga tcacggcaag cgcgcccgcc gcccgctgct          180
gcgctgcgct gcacgtcccg ccctgacgcc acgccacgcc aagcgcgaca cgacacgaca         240
cgacacgacc cgaccccgc caacgaaacg ccgaaacgcg caacgcgtg acgggcgcg           300
atggtcgatg ctctacccgc gcgtccgccc cacgccaatc tcccggcggg tcctcgtgg          360
gacggggaac gcgatgcggc tgcaggctgc gaccgcgacc gcgacgcgcga ccgcgcccac       420
gtgaaggcag gcaggcagcc ccggagcggg cgcggcggtg ggccaacgac gcgttgccgt        480
cgcgaatctt cttctggcca cggccaaggg ccaatcgccc gctccgctcc gctccgcact        540
ccgcctccgc tagggaatat ggaacccgat cccacgcccc tctgggtctg gtcgacgggt        600
cctctcgccg tggcagctgc ttcccggacc ggaggatcgc tgagcgcgga cgccactgcc        660
attgccgtcc gactatagtt gttaattacc ataaaatagt ttgttaacga taaacccgt          720
gtcaggcacc gtcgtctgga cgctgctatg ggataaccat tcgcgtacgt cggttgtatg         780
ggtgggatcc tctgcggcac gccattctgg tgctgctagt ggaatagaca aaaaagggc           840
cgacggtgtt tgctcgtggc aggccacaca gagtgacaac cagagtggtt gccgcaaaaa         900
caaccaatca cacaaaaagt gttgtaccgg tggaggacag ccattaatca gcaggccggc         960
ttcgcggcca aagaaacgg agaagaggaa aaggggggc                                 1000

SEQ ID NO: 184          moltype = DNA   length = 28
FEATURE                 Location/Qualifiers
source                  1..28
                        mol_type = other DNA
                        organism = synthetic construct
SEQUENCE: 184
tcccaagctt gcgcgtctcc gtgtcctc                                              28

SEQ ID NO: 185          moltype = DNA   length = 30
```

| FEATURE | Location/Qualifiers |
|---|---|
| source | 1..30 |
| | mol_type = other DNA |
| | organism = synthetic construct |

SEQUENCE: 185

```
agtaaagctt ccccctttt cctcttctcc                                    30
```

| SEQ ID NO: 186 | moltype = DNA   length = 1000 |
|---|---|
| FEATURE | Location/Qualifiers |
| source | 1..1000 |
| | mol_type = genomic DNA |
| | organism = Sorghum bicolor |

SEQUENCE: 186

```
taatggtcga gtgaggcccg tatagatgta gttaaatagc taaaattttt ggagaaataa   60
gcatttttt ggaagaatat atttaaacat gggcttgtaa aacttggctg taaagatttg   120
gaatttagga tcttggagcc ccaaaactgt ataaacttgc ttagggaccc gtgtcttgtg   180
tgttgcagac caaaaatt agaaagcatc taaacaccta tttgaatgta agtttacag    240
ccaaaagttt taggatgtaa agatttggga tctaaaagta gtcattagga ataacacgt    300
tagagagaga gagtagatct tcttattggt ttctcatgca ctaatcgaac caatcactgg   360
accacttgaa ccaaactta tcacattgaa ctttgtcagt tcagttcgaa cgcaggactg    420
gagctgcct taaggccaat tgctcaagat tcattcaaca attgaaacat ctcccatgat    480
taaatcagta taaggttgct atggtcttgc ttgacaaagt tttttttg agggaatttc    540
aactaaattt ttgagtgaaa ctatcaaata ctgattttaa aaatttttta taaaggaag    600
cgcagagata aaaggccatc tatgctacaa aagtacccaa aaatgtaaatc ctaaagtatg    660
aattgcattt tttttgtttg gacgaaagga aaggagtatt accacaagaa tgatatcatc    720
ttcatattta gatctttttt gggtaaagct tgagattctc taaatataga gaaatcagaa    780
gaaaaaaaa ccgtgttttg gtggttttga tttctagcct ccacaataac tttgacggcg    840
tcgacaagtc taacgacac caagcagcga accaccagcg ccgagccaag cgaagcgac    900
ggccgagacg ttgacacctt cggcgcggca tctctcgaga gttccgctcc ggcgctccac    960
ctccaccgct ggcggtttct tattccgttc cgttccgcct                       1000
```

| SEQ ID NO: 187 | moltype = DNA   length = 26 |
|---|---|
| FEATURE | Location/Qualifiers |
| source | 1..26 |
| | mol_type = other DNA |
| | organism = synthetic construct |

SEQUENCE: 187

```
aactgcaggg tcgagtgagg cccgta                                       26
```

| SEQ ID NO: 188 | moltype = DNA   length = 28 |
|---|---|
| FEATURE | Location/Qualifiers |
| source | 1..28 |
| | mol_type = other DNA |
| | organism = synthetic construct |

SEQUENCE: 188

```
ttctgcaggg aacggaacgg aataagaa                                     28
```

| SEQ ID NO: 189 | moltype = DNA   length = 239 |
|---|---|
| FEATURE | Location/Qualifiers |
| source | 1..239 |
| | mol_type = genomic DNA |
| | organism = Sorghum bicolor |

SEQUENCE: 189

```
gccgtgggtc gtttaagctg ccgctgtacc tgtgtcgtct ggtgccttct ggtgtacctg   60
ggaggttgtc gtctatcaag tatctgtggt tggtgtcatg agtcagtgag tcccaatact   120
gttcgtgtcc tgtgtgcatt atacccaaaa ctgtgtatgg caaatcatga ataagcttga   180
tgttcgaact taaagtctc tgctcaatat ggtattatgg ttgttttgt tcgtctcct    239
```

| SEQ ID NO: 190 | moltype = DNA   length = 27 |
|---|---|
| FEATURE | Location/Qualifiers |
| source | 1..27 |
| | mol_type = other DNA |
| | organism = synthetic construct |

SEQUENCE: 190

```
taggtaccgc cgtgggtcgt ttaagct                                      27
```

| SEQ ID NO: 191 | moltype = DNA   length = 27 |
|---|---|
| FEATURE | Location/Qualifiers |
| source | 1..27 |
| | mol_type = other DNA |
| | organism = synthetic construct |

SEQUENCE: 191

```
aaggtaccag gagacgaaca aaaacaa                                      27
```

| SEQ ID NO: 192 | moltype = DNA   length = 34 |
|---|---|
| FEATURE | Location/Qualifiers |
| source | 1..34 |
| | mol_type = other DNA |
| | organism = synthetic construct |

```
SEQUENCE: 192
aacgcgatcg taatggtcga gtgaggcccg tata                                  34

SEQ ID NO: 193          moltype = DNA  length = 1302
FEATURE                 Location/Qualifiers
source                  1..1302
                        mol_type = genomic DNA
                        organism = Brassica napus
SEQUENCE: 193
atgaagaaac tggttcatct tcagtttctg tttcttgtca agatctttgc tactcaattc    60
ctcactcctt cttcatcatc ttttgctgct tcaaatcctt ctatagctcc tgtttatacc   120
accatgacta ctttctctcc aggaattcaa atgggaagtg gtgaagaaca cagattagat   180
gcacataaga aactcctgat tggtcttata atcagttcct cttctcttgg tatcgtaatc   240
ttgatttgct ttggcttctg gatgtactgt cgcaagaaag ctcccaaacc catcaagatt   300
ccggatgctg agagtgggac ttcatcattt tcaatgtttg tgaggcggct aagctcaatc   360
aaaactcaga gaacatctag caatcagggt tatgtgcagc gtttcgattc aagacgctca   420
gagaaagcga caggcggttt caaagacagt aatgtaatcg gacagggcgg tttcggatgc   480
gtttacaagg cttctttgga cagcaaacac taaagcagcg ttaaaaagat cgaaaacgtt   540
agccaagaag caaaacgaga atttcagaat gaagttgagc tgttgagcaa gatccagcac   600
tccaatatta tatcattgtt gggctctgca agtgaaatca actcgagttt cgtcgtttat   660
gagttgatgg agaaaggatc cttagatgat cagttacatg gaccttcgtg tggatccgct   720
ctaacatggc atatgcgtat gaagattgct ctagatacag ctagaggatt agagtatctc   780
catgaacatt gtcgtccacc agttatccac agggacctga atcgtctaa tatacttctt    840
gattcttcct tcaatgccaa gatttcagat tttggtctgg ctgtatcggt tggagtgcat   900
gggagtaaca acattaaact ctctgggaca cttggttatg ttgccccgga atatctccta   960
gacggaaagt tgacggataa gagtgatgtc tatgcatttg gggtggttct tcttgaactt  1020
ttgttgggta aaggccggt tgagaaattg agtccatctc agtgtcaatc tcttgtgact   1080
tgggcaatgc cacaacttac cgatagatcg aaactcccaa acatcgtgga tccggttata   1140
aaagatacaa tggatcttaa gcacttatac caggtagcag ccatggctgt gttgtgcgtt   1200
cagccagaac cgagttaccg gccgctgata accgatgttc tcactcact tgttccattg   1260
gttccggtcg aactaggagg gactctccgg ttaacccgat ga                     1302

SEQ ID NO: 194          moltype = AA  length = 433
FEATURE                 Location/Qualifiers
source                  1..433
                        mol_type = protein
                        organism = Brassica napus
SEQUENCE: 194
MKKLVHLQFL FLVKIFATQF LTPSSSSFAA SNPSIAPVYT TMTTFSPGIQ MGSGEEHRLD    60
AHKKLLIGLI ISSSSLGIVI LICFGFWMYC RKKAPKPIKI PDAESGTSSF SMFVRRLSSI   120
KTQRTSSNQG YVQRFDSKTL EKATGGFKDS NVIGQGGFGC VYKASLDSNT KAAVKKIENV   180
SQEAKREFQN EVELLSKIQH SNIISLLGSA SEINSSFVVY ELMEKGSLDD QLHGPSCGSA   240
LTWHMRMKIA LDTARGLEYL HEHCRPPVIH RDLKSSNILL DSSFNAKISD FGLAVSVGVH   300
GSNNIKLSGT LGYVAPEYLL DGKLTDKSDV YAFGVVLLEL LLGRRPVEKL SPSQCQSLVT   360
WAMPQLTDRS KLPNIVDPVI KDTMDLKHLY QVAAMAVLCV QPEPSYRPLI TDVLHSLVPL   420
VPVELGGTLR LTR                                                      433

SEQ ID NO: 195          moltype = DNA  length = 31
FEATURE                 Location/Qualifiers
source                  1..31
                        mol_type = other DNA
                        organism = synthetic construct
SEQUENCE: 195
aatccagctc attctggaat tccttctcgc a                                    31

SEQ ID NO: 196          moltype = DNA  length = 32
FEATURE                 Location/Qualifiers
source                  1..32
                        mol_type = other DNA
                        organism = synthetic construct
SEQUENCE: 196
tgaacttgct caggattggc accagtgtga tc                                   32

SEQ ID NO: 197          moltype = AA  length = 461
FEATURE                 Location/Qualifiers
source                  1..461
                        mol_type = protein
                        organism = Brachypodium distachyon
SEQUENCE: 197
MEIPAAPPPP LPVLCSYVVF LLLLSSCSLA RGRIAVSSPG PSPVAAAVTA NETASSSSSP    60
VPPAAPPVVI TVVRHHHYHR ELVISAVLAC VATAMILLST LYAWTMWRRS RRTPHGGKGR   120
GRRSGITLVP ILSKFNSVKM SRKGGLVTMI EYPSLEAATG KFGESNVLGV GGFGCVYKAA   180
FDGGATAAVK RLEGGGPDCE KEFENELDLL GRIRHPNIVS LLGFCVHGGN HYIVYELMEK   240
GSLETQLHGS SHGSALSWHV RMKIALDTAR GLEYLHEHCN PPVIHRDLKP SNILLDSDFN   300
AKIADFGLAV TGGNLNKGNL KLSGTLGYVA PEYLLDGKLT EKSDVYAFGV VLLELLMGRK   360
PVEKMSPSQC QSIVSWAMPQ LTDRSKLPNI IDLVIKDTMD PKHLYQVAAV AVLCVQPEPS   420
YRPLITDVLH SLVPLVPAEL GGTLRVAEPP SPSPDQRHYP C                       461

SEQ ID NO: 198          moltype = DNA  length = 53
```

```
FEATURE            Location/Qualifiers
source             1..53
                   mol_type = other DNA
                   organism = synthetic construct
SEQUENCE: 198
tataccggta aaatgagaga gcttcttctt cttcttcttc ttcattttca gtc            53

SEQ ID NO: 199     moltype = DNA  length = 39
FEATURE            Location/Qualifiers
source             1..39
                   mol_type = other DNA
                   organism = synthetic construct
SEQUENCE: 199
atataccggt cttgttaacc ggagagtccc tcctagctc                            39

SEQ ID NO: 200     moltype = DNA  length = 18
FEATURE            Location/Qualifiers
source             1..18
                   mol_type = other DNA
                   organism = synthetic construct
SEQUENCE: 200
cgctcctccc gtcgtgat                                                   18
```

VECTOR COMPRISING SORGHUM TERMINATOR AND METHOD OF USE

REFERENCE TO RELATED APPLICATIONS

This application is a continuation application of U.S. patent application Ser. No. 16/678,306, filed on Nov. 8, 2019, which is a continuation of U.S. patent application Ser. No. 16/019,077, filed on Jun. 26, 2018, now U.S. Pat. No. 10,508,283, which is a continuation of U.S. patent application Ser. No. 15/266,276, filed on Sep. 15, 2016, now U.S. Pat. No. 10,036,035, which is a continuation of U.S. patent application Ser. No. 12/483,660, filed on Jun. 12, 2009, now U.S. Pat. No. 9,453,238, which claims the benefit of U.S. Ser. No. 61/132,067, filed Jun. 13, 2008, the contents of each of which are incorporated herein by reference in their entirety.

INCORPORATION-BY-REFERENCE OF SEQUENCE LISTING

The contents of the text file named "PREP_017_C05US_SeqList_ST26.xml", which was created on Sep. 26, 2022 and is 253, 276 bytes in size, are hereby incorporated by reference in their entireties.

FIELD OF THE INVENTION

The invention is in the field of plant molecular biology and relates to transgenic plants having novel phenotypes, methods of producing such plants and polynucleotides and polypeptides useful in such methods. More specifically, the invention relates to inhibition of a protein kinase and transgenic plants having inhibited protein kinase activity.

BACKGROUND OF THE INVENTION

Water is essential for plant survival, growth and reproduction. Assimilation of carbon dioxide by photosynthesis is directly linked to water loss through the stomata. Crop productivity which is closely linked to biomass production is dependent on plant water use efficiency (WUE) especially in water limited conditions (Passioura 1994 and Sinclair 1994, in Physiology and Determination of Crop Yield). Water use efficiency over a period of plant's growth can be calculated as the ratio of biomass produced per unit of water transpired (Sinclair 1994). Instantaneous measurements of water use efficiency can also be obtained as the ratio of carbon dioxide assimilation to transpiration using gas exchange measurements (Farquhar and Sharkey 1994, in Physiology and Determination of Crop Yield). Since there is a close correlation between crop productivity and water use efficiency, many attempts have been made to study and understand this relationship and the genetic components involved. To maximize the productivity and yield of a crop, efforts have been made to try to improve the water use efficiency of plants (Condon et al., 2002, Araus et al., 2002, Davies et al., 2002). Higher water use efficiency can be achieved either by increasing the biomass production and carbon dioxide assimilation or by reducing the transpiration water loss. Reduced transpiration, especially under non-limiting water conditions can be associated with reduced growth rate and therefore reduced crop productivity. This poses a dilemma on how to improve crop productivity and yield under water limited conditions but also maintain it under irrigated or non-limited water conditions (Condon et al., 2002).

Improvements to water use efficiency, to date, have used plant breeding methods whereby high water use efficiency varieties were crossed with the more productive but lower water use efficiency varieties in hope of improvements in crop yield under water limited conditions (Condon et al., 2002, Araus et al., 2002). Quantitative trait loci (QTL) approaches to identifying the components of water use efficiency have been the most common methods historically used (Mian et al., 1996, Martin et al., 1989, Thumma et al., 2001, Price et al., 2002), and more recently attempts have been made to engineer improved plants by molecular genetic means.

The first gene associated with water use efficiency was ERECTA. The ERECTA gene was first identified as a gene functioning in inflorescence development and organ morphogenesis (Torii et al., 1996,). It was later found by QTL mapping to be a major contributor to transpiration efficiency, defined as water transpired per carbon dioxide assimilated, an opposite indicator to water use efficiency in *Arabidopsis* (Masle et al., 2005). ERECTA encodes a putative leucin-rich repeat receptor-like kinase (LRR-RLK). The regulatory mechanism of LRR-RLK is yet to be understood although it was suggested due to, at least in part, the effects on stomatal density, epidermal cell expansion, mesophyll cell proliferation and cell-cell contact. The normal transpiration efficiency was restored upon complementation using wild type ERECTA in mutant exacta. However, it is not known whether overexpression of ERECTA in transgenic *Arabidopsis* will result in reduced transpiration efficiency or enhanced water use efficiency. It is the only report showing a plant receptor-like kinase to be involved in transpiration efficiency or water use efficiency.

Another *Arabidopsis* gene implicated in water use efficiency is the HARDY gene, found through the phenotypic screening of an activation tagged mutant collection (Karaba et al., 2007). Overexpression of HARDY in rice resulted in improved water use efficiency by enhancing photosynthetic assimilation and reducing transpiration. The transgenic rice with increased expression of HARDY exhibited increased shoot biomass under optimal water conditions and increased root biomass under water limited conditions. Overexpression of HARDY in *Arabidopsis* resulted in thicker leaves with more mesophyll cells and in rice increased leaf biomass and bundle sheet cells. These modifications contributed to enhanced photosynthetic activity and efficiency (Karaba et al., 2007).

Protein kinases are a large family of enzymes that modify proteins by addition of phosphate groups (phosphorylation). Protein kinases constitute about 2% of all eukaryotic genes, many of which mediate the response of eukaryotic cells to external stimuli. All single subunit protein kinases contain a common catalytic domain near the carboxyl terminus while the amino terminus plays a regulatory role.

Plant receptor-like kinases are serine/threonine protein kinases with a predicted signal peptide at the amino terminus, a single transmembrane region and a cytoplasmic kinase domain. There are more than 610 RLKs potentially encoded in *Arabidopsis* (Shiu and Bleecker 2001). Receptor-like kinases are often part of a signaling cascade. They interpret extracellular signals, through ligand binding, and phosphorylate targets in a signaling cascade which in turn affect downstream cell processes, such as gene expression (Hardie 1999).

Identification of genes that can be manipulated to provide beneficial characteristics is highly desirable. So too are means and methods of utilizing the identified genes to effect the desirable characteristics. The receptor-like kinase identified as At2g25220 in the TAIR database is one serine/threonine kinase, and a member of the large gene family of receptor-like kinases with over 600 members in *Arabidopsis* (Shiu et al., 2001). However, except for annotation of the sequence as a kinase no function or role for the At2g25220 gene has been disclosed. In the present invention a high water use efficiency gene (HWE) has been identified that when its expression or activity is inhibited results in beneficial phenotypes, such as, enhancement of plant biomass accumulation relative to the water used. This occurs under both water limited and non-limited conditions and ensures better growth and therefore greater productivity of the plants.

SUMMARY OF THE INVENTION

This invention is bases upon the discovery of a mutation in the PK220 gene that results in a plant with an altered phenotype such for example, increased water use efficiency, increased drought tolerance, reduced sensitivity to cold temperature and reduced inhibition of seedling growth in low nitrogen conditions compared to plants without the mutation.

More specifically, the invention relates to the identification of a mutant plant that comprises a mutation in the PK220 gene also referred to herein as the HWE gene. The PK220 gene is a receptor-like protein kinase. Inhibition of the expression or activity of the PK220 gene in plants provides beneficial phenotypes such as improved water use efficiency in a plant. The improved water use efficiency phenotype results in plants having improved drought tolerance.

In one aspect the invention provides a method of producing a transgenic plant, by transforming a plant, a plant tissue culture, or a plant cell with a vector containing a nucleic acid construct that inhibits the expression or activity of a PK220 gene to obtain a plant, tissue culture or a plant cell with decreased PK220 expression or activity and growing the plant or regenerating a plant from the plant tissue culture or plant cell. wherein a plant having increased water use efficiency is produced.

Accordingly, the present invention provides a method of producing a plant having an improved property, wherein the method includes inhibiting the expression or activity of an endogenous PK220 gene, wherein a plant is produced having an advantageous phenotype or improved property. In a particular embodiment, the present invention provides a method for producing plants having increased water use efficiency, wherein the method includes include generation of transgenic plants and modification of plants genome using the methods described herein.

Water use efficiency refers to the ratio between the amounts of biomass produced per unit water transpired when measured gravimetrically and the ratio of photosynthetic rate to the rate of transpiration when measured using gas exchange quantification of a leaf or shoot. As used herein, the term "increased water use efficiency" refers to a plant water use efficiency that is 2, 4, 5, 6, 8, 10, 20 or more fold greater as compared to the water use efficiency of a corresponding wild-type plant. For example, a plant having increased water use efficiency as compared to a wild-type plant may have 5%, 10%, 15%, 20%, 25%, 30%, 40%, 50%, 60% 70%, 75% or greater water use efficiency than the corresponding wild-type plant.

The methods of the invention involve inhibiting or reduced the expression or activity of an endogenous gene, such as PK220, wherein a plant is produced having an advantageous phenotype or improved property, such as increased water use efficiency. In one aspect, the invention provides a method of producing a plant having increased water use efficiency relative to a wild-type plant, by introducing into a plant cell a nucleic acid construct that inhibits or reduces the expression or activity of PK220. For example, a plant having increased water use efficiency relative to a wild type plant is produced by a) providing a nucleic acid construct containing a promoter operably linked to a nucleic acid construct that inhibits PK220 activity; b) inserting the nucleic construct into a vector; c) transforming a plant, tissue culture, or a plant cell with the vector to obtain a plant, tissue culture or a plant cell with decreased PK220 activity; d) growing the plant or regenerating a plant from the tissue culture or plant cell, wherein a plant having increased water use efficiency relative to a wild type plant is produced. The construct includes a promoter such as a constitutive promoter, a tissue specific promoter or an inducible promoter. Preferably, the tissue specific promoter is a root promoter. A preferable inducible promoter is a drought inducible promoter.

The term "nucleic acid construct" refers to a full length gene sequence or portion thereof, wherein a portion is preferably at least 19, 20, 21, 22, 23, 24, 25, 30, 40, 50, 60, 70, 75, 80, 90, 100, or 150 nucleotides in length, or the compliment thereof. Alternatively it may be an oligonucleotide, single or double stranded and made up of DNA or RNA or a DNA-RNA duplex. In a particular embodiment, the nucleic acid construct contains the full length PK220 gene sequence, or a portion thereof, wherein the portion of the PK220 sequence is at least 19, 20, 21, 22, 23, 24, 25, 30, 40, 50, 60, 70, 75, 80, 90, 100, or 150 nucleotides in length, or its compliment.

Also provided by the invention is a transgenic plant having an advantageous phenotype or improved property such as increased water use efficiency, produced by the methods described herein.

In another aspect the invention provides a plant having a non-naturally occurring mutation in an PK220 gene, wherein the plant has decreased PK220 expression or activity and the plant has increased water use efficiency relative to a wild-type control. Decreased PK220 expression or activity refers to a 2, 3, 4, 5, 6, 7, 8, 9, 10, 15, 20, 25, 30, 40, 50, 60, or 75-fold reduction or greater, at the DNA, RNA or protein level of an PK220 gene as compared to wild-type PK220, or a 2, 3, 4, 5, 6, 7, 8, 9, 10, 15, 20, 25, 30, 40, 50, 60 or 75 fold reduction of PK220 activity as compared to wild-type PK220 activity. PK220 activity includes but is not limited kinase activity at serine and or threonine amino acid residues of substrate polypeptides, where it participates in phosphorylation reactions.

The invention further provides a transgenic seed produced by the transgenic plant(s) of the invention, wherein the seed produces plant having an advantageous phenotype or improved property such as for example, increased water use efficiency relative to a wild-type plant.

In another embodiment, the invention provides nucleic acids for expression of nucleic acids in a plant cell to produce a transgenic plant having an advantageous phenotype or improved property such as increased water use efficiency.

Exemplary sequences encoding a wild type PK220 gene or portion thereof that find use in aspects of the present invention are described in SEQ ID NO's: 1, 7, 9, 11, 12, 13, 24, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 84, 86, 88, 90, 92, 94, 96, 98, 100, 153, 161 and 193. Exemplary sequences encoding a mutated PK220 gene are described in SEQ ID NO's:3 and 5. Exemplary sequences that are useful for constructs to downregulate PK220 expression or activity are described in SEQ ID NO's: 12, 13, 147, 149, 153, 161, 168 and 174. The invention further provides compositions which contain the nucleic acids of the invention for expression in a plant cell to produce the transgenic plants described herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from and are encompassed by the following detailed description and claims.

DETAILED DESCRIPTION

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

For convenience, before further description of the present invention, certain terms employed in the specification, examples and claims are defined herein. These definitions should be read in light of the remainder of the disclosure and as understood by a person of ordinary skill in the art.

A "promoter sequence", or "promoter", means a nucleic acid sequence capable of inducing transcription of an operably linked gene sequence in a plant cell. Promoters include for example (but not limited to) constitutive promoters, tissue specific promoters such as a root promoter, an inducible promoters such as a drought inducible promoter or an endogenous promoters such as a promoter normally associated with a gene of interest., i.e. a PK220 gene The term "expression cassette" means a vector construct wherein a gene or nucleic acid sequence is transcribed. Additionally, the expressed mRNA may be translated into a polypeptide.

The terms "expression" or "overexpression" are used interchangeably and mean the expression of a gene such that the transgene is expressed. The total level of expression in a cell may be elevated relative to a wild-type cell.

The term "non-naturally occurring mutation" refers to any method that introduces mutations into a plant or plant population. For example, chemical mutagenesis such as ethane methyl sulfonate or methanesulfonic acid ethyl ester, fast neutron mutagenesis, DNA insertional means such as a T-DNA insertion or site directed mutagenesis methods.

The term "drought stress" refers to a condition where plant growth or productivity is inhibited relative to a plant where water is not limiting. The term "water-stress" is used synonymously and interchangeably with the drought water stress.

The term "drought tolerance" refers to the ability of a plant to outperform a wildtype plant under drought stress conditions or water limited conditions or to use less water during grow and development relative to a wildtype plant.

The "term water use efficiency" is an expression of the ratio between the amounts of biomass produced per unit water transpired when measured gravimetrically and the ratio of photosynthetic rate to the rate of transpiration when measured using gas exchange quantification of a leaf or shoot.

The term "dry weight" means plant tissue that has been dried to remove the majority of the cellular water and is used synonymously and interchangeably with the term biomass.

The term "null" is defined as a segregated sibling of a transgenic line that has lost the inserted transgene and is therefore used a control line.

A number of various standard abbreviations have been used throughout the disclosure, such as g, gram; WT, wild-type; DW, dry weight; WUE, water use efficiency; d, day.

The term "hwe116" means a plant having a mutation in a PK220 gene.

The HWE gene is referred to as a PK220 gene sequence and a protein encoded by a PK220 gene is referred to as a PK220 polypeptide or protein. The terms HWE and PK220 are synonymous.

The term "PK220 nucleic acid" refers to at least a portion of a PK220 nucleic acid. Similarly the term "PK220 protein" or "PK220 polypeptide" refers to at least a portion thereof. A portion is of at least 21 nucleotides in length with respect to a nucleic acid and a portion of a protein or polypeptide is at least 7 amino acids. The term "AtPK220" refers to an *Arabidopsis thaliana* PK220 gene, the term "BnPK220" refers to a *Brassica napus* PK220 gene.

The invention is based in part on the discovery of plants having an improved agronomic property, for example, increased water use efficiency, increased drought tolerance, reduced sensitivity to cold temperature and reduced inhibition of seedling growth in low nitrogen conditions relative to a wild type control. The gene responsible for the beneficial phenotype has been determined and shown to be an inhibited PK220 gene.

Methods of producing a plant, including a mutant plant, a transgenic plant or genetically modified plant, having increased water use efficiency are disclosed herein. Specifically the invention identifies a PK220 gene that when expression or activity of the PK220 gene is inhibited, a plant having a beneficial phenotype is obtained.

Determining Homology Between Two or More Sequences

To determine the percent homology between two amino acid sequences or between two nucleic acids, the sequences are aligned for optimal comparison purposes (e.g., gaps can be introduced in either of the sequences being compared for optimal alignment between the sequences). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See, Needleman and Wunsch (1970). Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the coding sequence portion of the DNA sequence shown in SEQ ID NO:1.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region. The term "percentage of positive residues" is calculated by comparing two optimally aligned sequences over that region of comparison, determining the number of positions at which the identical and conservative amino acid substitutions, as defined above, occur in both sequences to yield the number of matched positions, dividing the number of matched positions by the total number of positions in the region of comparison (i.e., the window size), and multiplying the result by 100 to yield the percentage of positive residues.

Inhibition of Endogenous PK220 Expression and Activity

An aspect of the invention pertains to means and methods of inhibiting or reducing PK220 gene expression and activity, optionally, resulting in an inhibition or reduction of PK220 protein expression and activity. The term "PK220 expression or activity" embraces both these levels of inhibition or reduction. Decreased PK220 expression or activity refers to a 2, 3, 4, 5, 6, 7, 8, 9, 10, 15, 20, 25, 30, 40, 50, 60, or 75-fold reduction or greater, at the DNA, RNA or protein level of an PK220 gene as compared to wild-type PK220, or a 2, 3, 4, 5, 6, 7, 8, 9, 10, 15, 20, 25, 30, 40, 50, 60 or 75 fold reduction of PK220 protein activity as compared to wild-type PK220 activity. PK220 protein activity includes but is not limited kinase activity at serine and or threonine amino acid residues of substrate polypeptides, where it participates in phosphorylation reactions. Methods of measuring serine/threonine kinase activity are known to those in the art.

There are numerous methods known to those skilled in the art of achieving such inhibition that effect a variety of steps in a gene expression pathway, for example transcriptional regulation, post transcriptional and translational regulation. Such methods include, but are not limited to, antisense methods, RNAi constructs, including all hairpin constructs and RNAi constructs useful for inhibition by dsRNA-directed DNA methylation or inhibition by mRNA degradation or inhibition of translation, microRNA (miRNA), including artificial miRNA (amiRNA) (Schwab et al., 2006) technologies, mutagenesis and TILLING methods, in vivo site specific mutagenesis techniques and dominant/negative inhibition approaches.

A preferred method of gene inhibition involves RNA inhibition (RNAi) also known as hairpin constructs. A portion of the gene to inhibit is used and cloned in a sense and antisense direction having a spacer separating the sense and antisense portions. The size of the gene portions should be at least 20 nucleotides in length and the spacer may be a little as 13 nucleotides (Kennerdell and Carthew, 2000) in length and may be an intron sequence, a coding or non-coding sequence.

Antisense is a common approach wherein the target gene, or a portion thereof, is expressed in an antisense orientation resulting in inhibition of the endogenous gene expression and activity. The antisense portions need not be a full length gene nor be 100% identical. Provided that the antisense is at least about 70% or more identical to the endogenous target gene and of least 19, 20, 21, 22, 23, 24, 25, 30, 40, 50, 60, 70, 75, 80, 90, 100, or 150 nucleotides in length. Preferably, 50 nucleotides or greater in length the desired inhibition will be obtained.

Sequences encoding a wild type PK220 gene or portion thereof that are useful in preparing constructs for PK220 inhibition include for example, SEQ ID NO's: 1, 7, 9, 11, 12, 13, 24, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 84, 86, 88, 90, 92, 94, 96, 98, 100, 153, 161 and 193. Exemplary sequences that are useful for constructs to down-regulate PK220 expression or activity are described in SEQ ID NO's: 12, 13, 147, 149, 153, 161, 168 and 174.

When using an antisense strategy of down-regulation, inhibition of endogenous gene activity can be selectively targeted to the gene or genes of choice by proper selection of a fragment or portion for antisense expression. Selection of a sequence that is present in the target gene sequence and not present in related genes (non-target gene) or is less than 70% conserved in the non-target sequences results in specificity of gene inhibition.

Alternatively, amiRNA inhibition can be used to inhibit gene expression and activity in a more specific manner than other RNAi methods. In contrast to siRNA that requires a perfect match between the small RNA and the target mRNA, amiRNA allows up to 5 mismatches with no more than 2 consecutive mismatches. The construction of amiRNA needs to meet certain criteria described in Schawab et al. (2006). This provides a method to down-regulate a target gene expression or activity using a gene portion comprising of at least a 21 nucleotide sequence of PK220.

Dominant/negative inhibition is analogous to competitive inhibition of biochemical reactions. Expression of a modified or mutant polypeptide that lacks full functionality competes with the wild type or endogenous polypeptide thereby reducing the total gene/protein activity. For example an expressed protein may bind to a protein complex or enzyme subunit to produce a non-functional complex. Alternatively the expressed protein may bind substrate but not have activity to perform the native function. Expression of sufficient levels of non active protein will reduce or inhibit the overall function.

Expression of PK220 genes that produce a PK220 protein that is deficient in activity can be used for dominant/negative down-regulation of gene activity. This is analogous to competitive inhibition. A PK220 polypeptide is produced that, for example, may associate with or bind to a target molecule but lacks endogenous activity. An example of such an inactive PK220 is the AtPK220 sequence isolated from the hwe116 mutant and disclosed as SEQ ID NO:3. A target molecule may be an interacting protein of a nucleic acid sequence. In this manner the endogenous PK220 protein is effectively diluted and downstream responses will be attenuated.

In vivo site specific mutagenesis is available whereby one can introduce a mutation into a cells genome to create a specific mutation. The method as essentially described in Dong et al. (2006) or US patent application publication number 20060162024 which refer to the methods of oligonucleotide-directed gene repair. Alternatively one may use chimeric RNA/DNA oligonucleotides essentially as described Beetham (1999). Accordingly, a premature stop codon may be generated in the cells' endogenous gene thereby producing a specific null mutant. Alternatively, the mutation may interfere with splicing of the initial transcript thereby creating a non-translatable mRNA or a mRNA that produces an altered polypeptide which does not possess endogenous activity. Preferable mutations that result loss or reduction of PK220 expression or activity include a C to T conversion at nucleotide position 874 when numbered in accordance with SEQ ID NOs: 1 or 3 or a nucleotide mutation that results in an amino acid change from a Leucine (L) codon (CTT) to a Phenylalanine (F) codon (TTT) at amino acid position 292 when numbered in accordance with SEQ ID NOs: 2 or 4.

TILLING is a method of isolating mutations in a known gene from an EMS-mutagenized population. The population is screened by methods essentially as described in (Greene et al., 2003).

Other strategies of gene inhibition will be apparent to the skilled worker including those not discussed here and those developed in the future.

Identification of AtPK220 Homologues

Homologues of *Arabidopsis thaliana* PK220 (AtPK220) were identified using database sequence search tools, such as the Basic Local Alignment Search Tool (BLAST) (Altschul et al., 1990 and Altschul et al., 1997). The tblastn or blastn sequence analysis programs were employed using the BLOSUM-62 scoring matrix (Henikoff and Henikoff, 1992). The output of a BLAST report provides a score that takes into account the alignment of similar or identical residues and any gaps needed in order to align the sequences. The scoring matrix assigns a score for aligning any possible pair of sequences. The P values reflect how many times one expects to see a score occur by chance. Higher scores are preferred and a low threshold P value threshold is preferred. These are the sequence identity criteria. The tblastn sequence analysis program was used to query a polypeptide sequence against six-way translations of sequences in a nucleotide database. Hits with a P value less than −25, preferably less than −70, and more preferably less than −100, were identified as homologous sequences (exemplary selected sequence criteria). The blastn sequence analysis program was used to query a nucleotide sequence against a nucleotide sequence database. In this case too, higher scores were preferred and a preferred threshold P value was less than −13, preferably less than −50, and more preferably less than −100.

A PK220 gene can be isolated via standard PCR amplification techniques. Use of primers to conserved regions of a PK220 gene and PCR amplification produces a fragment or full length copy of the desired gene. Template may be DNA, genomic or a cDNA library, or RNA or mRNA for use with reverse transcriptase PCR (RtPCR) techniques. Conserved regions can be identified using sequence comparison tools such as BLAST or CLUSTALW for example. Suitable primers have been used and described elsewhere in this application.

Alternatively, a fragment of a sequence from a PK220 gene is $^{32}$P-radiolabeled by random priming (Sambrook et al., 1989) and used to screen a plant genomic library (the exemplary test polynucleotides). As an example, total plant DNA from *Arabidopsis thaliana, Nicotiana tabacum, Lycopersicon pimpinellifolium, Prunus avium, Prunus cerasus, Cucumis sativus,* or *Oryza sativa* are isolated according to Stockinger et al. (Stockinger et al., 1996). Approximately 2 to 10 µg of each DNA sample are restriction digested, transferred to nylon membrane (Micron Separations, Westboro, Mass) and hybridized. Hybridization conditions are: 42° C. in 50% formamide, 5×SSC, 20 mM phosphate buffer 1×Denhardt's, 10% dextran sulfate, and 100 µg/ml herring sperm DNA. Four low stringency washes at RT in 2×SSC, 0.05% sodium sarcosyl and 0.02% sodium pyrophosphate are performed prior to high stringency washes at 55° C. in 0.2.times.SSC, 0.05% sodium sarcosyl and 0.01% sodium pyrophosphate. High stringency washes are performed until no counts are detected in the washout according to Walling et al. (Walling et al., 1988). Positive isolates are identified, purified and sequenced. Other methods are available for hybridization, for example the ExpressHyb hybridization solution available from Clonetech.

PK220 Recombinant Expression Vectors and Host Cells

Another aspect of the invention pertains to vectors, preferably expression vectors, containing a nucleic acid encoding a PK220 protein, a PK220 gene or genomic sequence or portions thereof and analogs or homologs thereof. As used herein the term expression vector includes vectors which are designed to provide transcription of the nucleic acid sequence. Transcribed sequences may be designed to inhibit the endogenous expression or activity of an endogenous gene activity correlating to the transcribed sequence. Optionally, the transcribed nucleic acid need not be translated but rather inhibits the endogenous gene expression as in antisense or hairpin down-regulation methodology. Alternatively, the transcribed nucleic acid may be translated into a polypeptide or protein product. The polypeptide may be a non-full length, mutant or modified variant of the endogenous protein. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication). Other vectors are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors or plant transformation vectors, binary or otherwise, which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to include promoters, enhancers and other expression control elements (e.g., polyadenylation signals). Such regulatory sequences are described, for example, in Goeddel (1990). Regulatory sequences include those that direct constitutive expression of a nucleotide sequence in many types of host cell and those that direct expression of the nucleotide sequence only in certain host cells (e.g., tissue-specific regulatory sequences) or inducible promoters (e.g., induced in response to abiotic factors such as environmental conditions, heat, drought, nutrient status or physiological status of the cell or biotic such as pathogen responsive). Examples of suitable promoters include for example constitutive promoters, ABA inducible promoters, tissue specific promoters and abiotic or biotic inducible promoters. It will be appreciated by those skilled in the art that the design of the expression vector can depend on such factors as the choice of the host cell to be transformed, the level of expression of protein desired as well as timing and location of expression, etc. The expression vectors of the invention can be introduced into host cells to thereby produce proteins or peptides, including fusion proteins or peptides, encoded by nucleic acids as described herein (e.g., PK220 proteins, mutant forms of PK220 proteins, fusion proteins, etc.).

The recombinant expression vectors of the invention can be designed for expression of PK220 genes, PK220 proteins, or portions thereof, in prokaryotic or eukaryotic cells. For example, PK220 genes or PK220 proteins can be expressed in bacterial cells such as *Escherichia coli*, insect cells (using baculovirus expression vectors,) yeast cells, plant cells or mammalian cells. Suitable host cells are discussed further in Goeddel (1990). Alternatively, the recombinant expression vector can be transcribed and translated in vitro, for example using T7 promoter regulatory sequences and T7 polymerase.

In one embodiment, a nucleic acid of the invention is expressed in plants cells using a plant expression vector. Examples of plant expression vectors systems include tumor inducing (Ti) plasmid or portion thereof found in *Agrobacterium*, cauliflower mosaic virus (CaMV) DNA and vectors such as pBI121.

For expression in plants, the recombinant expression cassette will contain in addition to the PK220 nucleic acids, a promoter region that functions in a plant cell, a transcription initiation site (if the coding sequence to transcribed lacks one), and optionally a transcription termination/polyadenylation sequence. The termination/polyadenylation region may be obtained from the same gene as the promoter sequence or may be obtained from different genes. Unique restriction enzyme sites at the 5' and 3' ends of the cassette are typically included to allow for easy insertion into a pre-existing vector.

Examples of suitable promoters include promoters from plant viruses such as the 35S promoter from cauliflower mosaic virus (CaMV) (Odell et al., 1985), promoters from genes such as rice actin (McElroy et al., 1990), ubiquitin (Christensen et al., 1992; pEMU (Last et al., 1991), MAS (Velten et al., 1984), maize H3 histone (Lepetit et al., 1992); and Atanassvoa et al., 1992), the 5'- or 3'-promoter derived from T-DNA of *Agrobacterium tumefaciens*, the Smas promoter, the cinnamyl alcohol dehydrogenase promoter (U.S. Pat. No. 5,683,439), the Nos promoter, the rubisco promoter, the GRP1-8 promoter, ALS promoter, (WO 96/30530), a synthetic promoter, such as Rsyn7, SCP and UCP promoters, ribulose-1,3-diphosphate carboxylase, fruit-specific promoters, heat shock promoters, seed-specific promoters and other transcription initiation regions from various plant genes, for example, including the various opine initiation regions, such as for example, octopine, mannopine, and nopaline. In some cases a promoter associated with the gene of interest (e.g. PK220) may be used to express a construct targeting the gene of interest, for example the native AtPK220 promoter ($P_{PK}$). Additional regulatory elements that may be connected to a PK220 encoding nucleic acid sequence for expression in plant cells include terminators, polyadenylation sequences, and nucleic acid sequences encoding signal peptides that permit localization within a plant cell or secretion of the protein from the cell. Such regulatory elements and methods for adding or exchanging these elements with the regulatory elements of PK220 gene are known and include, but are not limited to, 3' termination and/or polyadenylation regions such as those of the *Agrobacterium tumefaciens* nopaline synthase (nos) gene (Bevan et al., 1983); the potato proteinase inhibitor II (PINII) gene (Keil et al., 1986) and hereby incorporated by reference); and An et al. (1989); and the CaMV 19S gene (Mogen et al., 1990).

Plant signal sequences, including, but not limited to, signal-peptide encoding DNA/RNA sequences which target proteins to the extracellular matrix of the plant cell (Dratewka-Kos et al., 1989) and the *Nicotiana plumbaginifolia* extension gene (De Loose et al., 1991), or signal peptides which target proteins to the vacuole like the sweet potato sporamin gene (Matsuoka et al., 1991) and the barley lectin gene (Wilkins et al., 1990), or signals which cause proteins to be secreted such as that of PRIb (Lund et al., 1992), or those which target proteins to the plastids such as that of rapeseed enoyl-ACP reductase (Verwoert et al., 1994) are useful in the invention.

In another embodiment, the recombinant expression vector is capable of directing expression of the nucleic acid preferentially in a particular cell type (e.g., tissue-specific regulatory elements are used to express the nucleic acid). Tissue-specific regulatory elements are known in the art. For example, the promoter associated with a coding sequence identified in the TAIR data base as At2g44790 ($P_{4790}$) is a root specific promoter. Especially useful in connection with the nucleic acids of the present invention are expression systems which are operable in plants. These include systems which are under control of a tissue-specific promoter, as well as those which involve promoters that are operable in all plant tissues.

Organ-specific promoters are also well known. For example, the chalcone synthase-A gene (van der Meer et al., 1990) or the dihydroflavonol-4-reductase (dfr) promoter (Elomaa et al., 1998) direct expression in specific floral tissues. Also available are the patatin class I promoter is transcriptionally activated only in the potato tuber and can be used to target gene expression in the tuber (Bevan, 1986). Another potato-specific promoter is the granule-bound starch synthase (GBSS) promoter (Visser et al., 1991).

Other organ-specific promoters appropriate for a desired target organ can be isolated using known procedures. These control sequences are generally associated with genes uniquely expressed in the desired organ. In a typical higher plant, each organ has thousands of mRNAs that are absent from other organ systems (reviewed in Goldberg, 1986).

The resulting expression system or cassette is ligated into or otherwise constructed to be included in a recombinant vector which is appropriate for plant transformation. The vector may also contain a selectable marker gene by which transformed plant cells can be identified in culture. The marker gene may encode antibiotic resistance. These markers include resistance to G418, hygromycin, bleomycin, kanamycin, and gentamicin. Alternatively the marker gene may encode a herbicide tolerance gene that provides tolerance to glufosinate or glyphosate type herbicides. After transforming the plant cells, those cells having the vector will be identified by their ability to grow on a medium containing the particular antibiotic or herbicide. Replication sequences, of bacterial or viral origin, are generally also included to allow the vector to be cloned in a bacterial or phage host, preferably a broad host range prokaryotic origin of replication is included. A selectable marker for bacteria should also be included to allow selection of bacterial cells bearing the desired construct. Suitable prokaryotic selectable markers also include resistance to antibiotics such as kanamycin or tetracycline.

Other DNA sequences encoding additional functions may also be present in the vector, as is known in the art. For instance, in the case of *Agrobacterium* transformations, T-DNA sequences will also be included for subsequent transfer to plant chromosomes.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell.

A host cell of the invention, such as a prokaryotic or eukaryotic host cell in culture, can be used to produce (i.e., express) a polypeptide of the invention encoded in an open reading frame of a polynucleotide of the invention. Accordingly, the invention further provides methods for producing a polypeptide using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

A number of cell types may act as suitable host cell for expression of a polypeptide encoded by an open reading frame in a polynucleotide of the invention. Plant host cells include, for example, plant cells that could function as suitable hosts for the expression of a polynucleotide of the invention include epidermal cells, mesophyll and other ground tissues, and vascular tissues in leaves, stems, floral organs, and roots from a variety of plant species, such as *Arabidopsis thaliana, Nicotiana tabacum, Brassica napus, Zea mays, Oryza sativa, Gossypium hirsutum* and *Glycine max.*

Expression of PK220 nucleic acids encoding a PK220 protein that is not fully functional can be useful in a dominant/negative inhibition method. A PK220 variant polypeptide, or portion thereof, is expressed in a plant such that it has partial functionality. The variant polypeptide may for example have the ability to bind other molecules but does not permit proper activity of the complex, resulting in overall inhibition of PK220 activity.

Transformed Plants Cells and Transgenic Plants

The invention includes a protoplast, plants cell, plant tissue and plant (e.g., monocot or dicot) transformed with a PK220 nucleic acid, a vector containing a PK220 nucleic acid or an expression vector containing a PK220 nucleic acid. As used herein, "plant" is meant to include not only a whole plant but also a portion thereof (i.e., cells, and tissues, including for example, leaves, stems, shoots, roots, flowers, fruits and seeds).

The plant can be any plant type including, for example, species from the genera *Arabidopsis, Brassica, Oryza, Zea, Sorghum, Brachypodium, Miscanthus, Gossypium, Triticum, Glycine, Pisum, Phaseolus, Lycopersicon, Trifolium, Cannabis, Cucurbita, Rosa, Vitis, Juglans, Fragaria, Lotus, Medicago, Onobrychis, Trigonella, Vigna, Citrus, Linum, Geranium, Manihot, Daucus, Raphanus, Sinapis, Atropa, Capsicum, Datura, Hyoscyamus, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Lolium, Avena, Hordeum, Secale, Picea, Caco,* and *Populus.*

The invention also includes cells, tissues, including for example, leaves, stems, shoots, roots, flowers, fruits and seeds and the progeny derived from the transformed plant.

Numerous methods for introducing foreign genes into plants are known and can be used to insert a gene into a plant host, including biological and physical plant transformation protocols (See, for example, Miki et al., (1993) "Procedure for Introducing Foreign DNA into Plants", In: Methods in Plant Molecular Biology and Biotechnology, Glick and Thompson, eds., CRC Press, Inc., Boca Raton, pages 67-88; and Andrew Bent in, Clough S J and Bent A F, (1998) "Floral dipping: a simplified method for *Agrobacterium*-mediated transformation of *Arabidopsis thaliana*"). The methods chosen vary with the host plant, and include chemical transfection methods such as calcium phosphate, polyethylene glycol (PEG) transformation, microorganism-mediated gene transfer such as *Agrobacterium* (Horsch et al., 1985), electroporation, protoplast transformation, micro-injection, flower dipping and biolistic bombardment.

*Agrobacterium*-Mediated Transformation

The most widely utilized method for introducing an expression vector into plants is based on the natural transformation system of *Agrobacterium* tumefaciens and *A. rhizogenes* which are plant pathogenic bacteria which genetically transform plant cells. The Ti and Ri plasmids of *A. tumefaciens* and *A. rhizogenes*, respectfully, carry genes responsible for genetic transformation of plants (See, for example, Kado, 1991). Descriptions of the *Agrobacterium* vector systems and methods for *Agrobacterium*-mediated gene transfer are provided in Gruber et al. (1993). and Moloney et al., (1989).

Transgenic *Arabidopsis* plants can be produced easily by the method of dipping flowering plants into an *Agrobacterium* culture, based on the method of Andrew Bent in, Clough S J and Bent A F, 1998. Floral dipping: a simplified method for *Agrobacterium*-mediated transformation of *Arabidopsis thaliana*. Wild type plants are grown until the plant has both developing flowers and open flowers. The plants are inverted for 1 minute into a solution of *Agrobacterium* culture carrying the appropriate gene construct. Plants are then left horizontal in a tray and kept covered for two days to maintain humidity and then righted and bagged to continue growth and seed development. Mature seed is bulk harvested.

Direct Gene Transfer

A generally applicable method of plant transformation is microprojectile-mediated transformation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes. (Sanford et al., 1993; Klein et al., 1992).

Plant transformation can also be achieved by the Aerosol Beam Injector (ABI) method described in U.S. Pat. Nos. 5,240,842, 6,809,232. Aerosol beam technology is used to accelerate wet or dry particles to speeds enabling the particles to penetrate living cells. Aerosol beam technology employs the jet expansion of an inert gas as it passes from a region of higher gas pressure to a region of lower gas pressure through a small orifice. The expanding gas accelerates aerosol droplets, containing nucleic acid molecules to be introduced into a cell or tissue. The accelerated particles are positioned to impact a preferred target, for example a plant cell. The particles are constructed as droplets of a sufficiently small size so that the cell survives the penetration. The transformed cell or tissue is grown to produce a plant by standard techniques known to those in the applicable art.

Regeneration of Transformants

The development or regeneration of plants from either single plant protoplasts or various explants is well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by *Agrobacterium* from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983). In particular, U.S. Pat. No. 5,349,124 (specification incorporated herein by reference) details the creation of genetically transformed lettuce cells and plants resulting therefrom which express hybrid crystal proteins conferring insecticidal activity against Lepidopteran larvae to such plants.

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, or pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

A preferred transgenic plant is an independent segregate and can transmit the PK220 gene construct to its progeny. A more preferred transgenic plant is homozygous for the gene construct, and transmits that gene construct to all offspring on sexual mating. Seed from a transgenic plant may be grown in the field or greenhouse, and resulting sexually mature transgenic plants are self-pollinated to generate true breeding plants. The progeny from these plants become true breeding lines that are evaluated for decreased expression of the PK220 gene.

Method of Producing Transgenic Plants

Also included in the invention are methods of producing a transgenic plant having increased water use efficiency, reduced sensitivity to cold temperature and reduced inhibition of seedling growth in low nitrogen conditions, relative to a wild type plant. The method includes introducing into one or more plant cells a compound that inhibits or reduces PK220 expression or activity in the plant to generate a transgenic plant cell and regenerating a transgenic plant from the transgenic cell. The compound can be, e.g., (i) a PK220 polypeptide; (ii) a PK220 nucleic acid, analog, homologue, orthologue, portion, variant or complement thereof; (iii) a nucleic acid that decreases expression of a PK220 nucleic acid. A nucleic acid that decreases expression of a PK220 nucleic acid may include promoters or enhancer elements. The PK220 nucleic acid can be either endogenous or exogenous, for example an *Arabidoposis* PK220 nucleic acid may be introduced into a *Brassica* or corn species. Preferably, the compound is a PK220 nucleic acid sequence endogenous to the species being transformed. Alternatively, the compound is a PK220 nucleic acid sequence exogenous to the species being transformed and having at least 70%, 75%, 80%, 85%, 90% or greater homology to the endogenous target sequence.

In various aspects the transgenic plant has an altered phenotype as compared to a wild type plant (i.e., untransformed). By altered phenotype is meant that the plant has a one or more characteristic that is different from the wild type plant. For example, when the transgenic plant has been contacted with a compound that decreases the expression or activity of a PK220 nucleic acid, the plant has a phenotype such as increased water use efficiency, reduced sensitivity to cold temperature and reduced inhibition of seedling growth in low nitrogen conditions, relative to a wild type plant.

The plant can be any plant type including, for example, species from the genera *Arabidopsis, Brassica, Oryza, Zea, Sorghum, Brachypodium, Miscanthus, Gossypium, Triticum, Glycine, Pisum, Phaseolus, Lycopersicon, Trifolium, Cannabis, Cucurbita, Rosa, Vitis, Juglans, Fragaria, Lotus, Medicago, Onobrychis, Trigonella, Vigna, Citrus, Linum, Geranium, Manihot, Daucus, Raphanus, Sinapis, Atropa, Capsicum, Datura, Hyoscyamus, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio,*

Salpiglossis, Cucumis, Browaalia, Lolium, Avena, Hordeum, Secale, Picea, Caco, and Populus.

EXAMPLES

Identification of High Water Use Efficiency Mutant hwe116

An Arabidopsis EMS mutant (Columbia background) was identified initially as having drought tolerant properties. The mutant was tested for water use efficiency under optimal and drought conditions. The result showed that the drought tolerant nature of this mutant is due to its higher water use efficiency under both water stressed and optimal water conditions. Thus, this mutant is named hwe116.

Map Based Cloning of Hwe116

A F2 population was generated by crossing the hwe116 mutant to the Landsberg erecta (Ler) ecotype of Arabidopsis thaliana and the resulting population was used for map-based cloning by assaying for drought tolerance and subsequently confirming the presence of the higher water use efficiency trait in the mutant. The water-loss per unit dry weight of the F2 plants was measured over a 5-day drought treatment and the data was normalized for QTL analysis relative to the hwe116 mutant and the two wild type ecotypes, Landsberg erecta and Columbia. Leaf tissues were collected from all F2 and control plants used in the phenotyping experiments for genotyping. QTL analysis was conducted using MAPMAKER 3.0 and WinQTLCart 2.5. To further specify the mutations within the QTL peak, celery endonuclease I (CEL I) was used.

Mutation Detection Using CEL I Nuclease

Celery endonuclease I (CEL I), cleaves DNA with high specificity at sites of base-pair substitution that creates a mismatch between wild type and mutant alleles and has been reportedly used for detecting mutations in EMS mutants (Yang et al., 2000; Oleykowski et al., 1998).

DNA fragments of about 5 kb were amplified by optimized PCR using hwe116 or parent Columbia genomic DNA as template. Equal amounts of the amplified products were mixed together and then subjected to a cycle of denaturing and annealing to form heteroduplex DNA. Incubation with CEL I at 42° C. for 20 minutes cleaves the heteroduplex DNA at points of mutation, and DNA fragments were visualized by 1% agarose gel electrophoresis and ethidium bromide staining.

Using this method a 5 kb PCR product was amplified using primers SEQ ID NO:102 and SEQ ID NO:104, and templates: hwe116, and the control Columbia type. The heteroduplexes formed PCR products resulted in smaller fragments (1.4 and 3.6 kb) after CEL I digestion. Overlapping sub-fragments (about 3 kb) were amplified using primers SEQ ID NO:104 and SEQ ID NO:105 to more narrowly define the mutation location. The sub-fragment was sequenced and a C nucleotide was found to have been mutated to T nucleotide in hwe116.

The mutation of interest was identified as a C to T conversion at nucleotide position 874 of SEQ ID NO's:1 and 3 that resulted in an amino acid change from a Leucine (L) codon (CTT) to a Phenylalanine (F) codon (TTT) at amino acid position 292. The gene harboring the mutation was identified as a Serine/Threonine protein kinase (Ser/Thr PK). The wild type gene was identified as being identical to Genbank Accession Number At2g25220. This Ser/Thr protein kinase is referred to as AtPK220 herein, and the mutated form identified in hwe116 is referred to as AtPK220L292F.

Transcriptional Evaluation

Northern analysis and RT-PCR indicate that the expression level and transcript size of the AtPK220 gene in hwe116 is unchanged relative to the wild type control.

Initial Cloning of Partial AtPK220L292F and AtPK220 Sequences

Based on the TAIR annotation, partial sequences of AtPK220L292F (AtPK220L292F(p)) and partial AtPK220 (AtPK220(p)) were amplified by RT-PCRs using the primers SEQ ID NO:106 and SEQ ID NO:107 which included BamHI and PstI restriction sites for cloning and template RNA isolated from hwe116 and the control plant (Columbia), respectively). The resulting partial AtPK220L292F nucleotide sequence is shown as SEQ ID NO:5 and the corresponding amino acid sequence as SEQ ID NO:6. The resulting partial AtPK220 nucleotide sequence is shown as SEQ ID NO:7 and the corresponding amino acid sequence as SEQ ID NO:8.

Kinase Activity Assay of a Partial AtPK220L292F Protein Expressed in E. coli

The PCR products were digested with BamHI and PstI, and inserted into the expression vector: pMAL-c2 (New England Biolabs, Beverly, MA) to form an in-frame fusion protein with the malE gene for expression of the maltose-binding protein: MBP-AtPK220L292F(p) and MBP-AtPK220(p). The fusion proteins were expressed in E. coli and purified using amylose-affinity chromatography as described by the manufacturer (New England Biolabs). Fractions containing the fusion proteins were pooled and concentrated (Centriprep-30 concentrator, Amicon). SDS-PAGE was used to analyze the expression level, size and purity of the fusion proteins.

Activity assays were carried out according to (Huang et al., 2000). The kinase autophosphorylation assay mixtures (30 µl) contained kinase reaction buffer (50 mM Tris, pH 7.5, 10 mM $MgCl_2$, 10 mM $MnCl_2$), 1 µCi [$\gamma$-$^{32}$P] ATP and 10 ng of purified AtPK220L292F(p) or MBP-AtPK220(p). For the trans-phosphorylation assays, myelin basic protein (3 µg) was added to each assay. The reactions were started by the addition of the enzymes. After incubation at room temperature for 30 min, the reactions were terminated by the addition of 30 µl of Laemmli sample buffer (Laemmli, 1970). The samples were heated at 95° C. for 5 min and then loaded on a 15% SDS-polyacrylamide gel. The gels were stained with Coomassie blue R-250, then de-stained and dried. The $^{32}$P-labeled bands were detected using Kodak X-Omat AR film.

The wild type MBP-AtPK220(p) fusion protein was able to phosphorylate the artificial substrate in the in vitro activity assay, indicating that the assay system was effective and the MBP-AtPK220(p) fusion protein was capable of activity. In contrast, the hwe116 mutant form, MBP-AtPK220L292F(p), was unable to catalyse phosphorylation of the model substrate. The single point mutation is sufficient to abolish activity of the AtPK220(p) gene from hwe116.

Isolation of Full-Length cDNA Sequence of AtPK220

The annotation of AtPK220 (At2g25220) in the TAIR database identifies a 5' start codon, termination signal and 3' UTR sequence. Analysis of the 5' portion of the annotated sequence suggested an alternative 5' sequence and start codon location. To determine the AtPK220 genes' 5' region and the likely start codon SMART RACE (Rapid Amplification of cDNA Ends, CloneTech) was performed.

A specific primer, SEQ ID NO:108, was designed for 5' RACE and yielded a 450 bp PCR product. Sequence data obtained of the 450 bp 5' RACE product indicated that the TAIR annotation of AtPK220 was missing the 5' 186 bp that included 39 bp of 5' UTR sequence and 147 bp of coding sequence. An intron of 324 bp, located 8 bp upstream of the TAIR identified ATG start codon of AtPK220 was also missing from the genomic annotation in TAIR.

Compiling the 5' RACE results and TAIR database annotation yields the full-length cDNA of AtPK220 (SEQ ID NO:9). The sequence was determined to be 1542 bp in length, which included 39 bp of 5' UTR, 204 bp of 3'UTR, and 1299 bp of coding region. The AtPK220 coding region is identified as SEQ ID NO:1 and encodes a protein of 432 amino acids and is identified as SEQ ID NO:2. Comparison of AtPK220 to its closest homolog, At4g32000, shows an additional sequence of 51 bp is present in AtPK220, that includes the sequence of nucleotides 368-418 of SEQ ID NO:9. This sequence provides a target sequence for down-regulation constructs designed to specifically down-regulate the AtPK220 gene but not non-target genes such as At4g32000.

Sequence analysis of AtPK220 indicates that this Ser/Thr PK belongs to a receptor-like protein kinase family, possessing a signal peptide (1-29), an extracellular domain (30-67), a single transmembrane domain (68-88), an ATP-binding domain (152-175 as determined by Prosite) a Ser/Thr protein kinase active-site domain (267-279 as determined by the InterPro method) and an activation loop(289-298, 303-316).

Rescue of the hwe116 Mutant by AtPK220

Constructs for the expression of wild-type AtPK220 were generated and transformed into the hwe116 mutant. The construct was constitutively expressed from a CaMV 35S promoter and referred to as 35S-AtPK220.

35S-AtPK220

The primer pair SEQ ID NO:109 and SEQ ID NO:110 was used to amplify a fragment comprising the full length open reading frame (ORF) of AtPK220. The primer pair SEQ ID NO:111 and SEQ ID NO:110 was used to amplify a fragment comprising a portion of AtPK220 ORF. The amplified fragments were digested with restriction enzymes SmaI and BamHI and cloned into a pEGAD vector digested with the same restriction enzymes. The fragment comprising the full length open reading frame of AtPK220 resulting from the PCR and subsequent restriction digestion is disclosed as SEQ ID NO:10. The fragment comprising a portion of the AtPK220 ORF resulting from the PCR and subsequent restriction digestion is disclosed as SEQ ID NO:11.

The 35S-AtPK220 construct was transformed into *Arabidopsis* hwe116. The transgenic lines were recovered and advanced to T3 homozygous lines. These lines are tested for their drought tolerance and water use efficiency characteristics. The 35S-AtPK220 construct restores the wild type phenotypes.

T-DNA Knockout Lines and Physiology Assessment

SALK T-DNA knockout lines of AtPK220 and two close homologous genes in which are identified as TAIR Accession numbers AT4G32000 (SEQ ID NO:16) and AT5G11020 (SEQ ID NO:18) were obtained from ABRC and advanced to homozygosity. They are listed as follows;

AtPK220: SALK_147838;
AtPK32000 (AT4G32000): SALK_060167, SALK_029937 and SALK_121979;
AtPK11020 (AT5G11020): SAIL 1260_H05.

Analysis of gene expression levels by either RT-PCR or Northern analysis demonstrated that the target genes in the knockout lines was either significantly reduced or completely abolished. These knockout lines were used for physiological assessment. Only the knockout line of AtPK220 (SALK_147838) showed significant drought tolerance and higher water use efficiency, indicating that AtPK220 is the target gene and responsible for the water use efficiency phenotype of hwe116. The closely related genes AT4G32000 and AT5G11020 are not functionally redundant and inhibition of these genes is insufficient to generate the hwe116 phenotype.

Inhibition of the Protein Activity for PK220 in *Arabidopsis*

Inhibition of gene activity can be achieved by a variety of technical means, for example, antisense expression, RNAi or hairpin constructs, in vivo mutagenesis, dominant negative approaches or generation of a mutant population and selection of appropriate lines by screening means. Provided are examples of said means to produce plants having inhibited PK220 gene expression and or activity.

Down-Regulation of PK220 by RNAi

Constructs were designed for RNAi inhibition of PK220 using hairpin (HP) constructs. The constructs comprised a 288 bp or a 154 bp of AtPK220 cDNA sequence to produce constructs referred to as (270)PK220 and (150)PK220. The 288 bp (270)PK220 fragment comprises 10 bp of intron sequence that was included in the PCR primer during construction of these PCR products. Vector constructs using these fragments can be made to drive expression under the control of a promoter of choice that will be apparent to one of skill in the art. In these examples a constitutive promoter (35S CaMV), or the native AtPK220 promoter ($P_{PK}$) was used. Two fragments, or portions, of the AtPK220 gene were selected, first a 288 bp fragment At(270)PK220 (SEQ ID NO:13) and second a 154 bp fragment At(150)PK220 (SEQ ID NO:12) were selected from a divergent region of AtPK220 as compared to its closest homologue At4g32000.

35S-HP-At(270)PK220 and 35S-HP-At(150)PK220

The hairpin constructs (HP) 35S-HP-At(270)PK220 and 35S-HP-At(150)PK220 constructs were generated as follows. The sense fragments of (270)PK220 and (150)PK220 were amplified by RT-PCR using primer pairs of SEQ ID NO:134/SEQ ID NO:115 and SEQ ID NO:114/SEQ ID NO:115, respectively. The PCR products were digested with SacI, and inserted into a binary vector pBI121tGUS at the SacI site, respectively. The resulting vectors were then used to subclone the antisense fragments of (270)PK220 and (150)PK220 that were derived from RT-PCR products amplified using primer pairs of SEQ ID NO:112/SEQ ID NO:117, and SEQ ID NO:116/SEQ ID NO:117, respectively. Both the vector and PCR products were digested with BamHI and XbaI for subcloning.

$P_{PK}$-HP-At(270)PK220 and $P_{PK}$-HP-At(150)PK220

The $P_{PK}$-HP-At(270)PK220 and $P_{PK}$-HP-At(150)PK220 constructs were made from 35S-HP-At(270)PK220 or 35S-HP-At(150)PK220 respectively by replacing the 35S promoter sequence with AtPK220 promoter sequence (SEQ ID NO:14). The 35S promoter sequence was removed from 35S-HP-At(270)PK220 and 35S-HP-At(150)PK220 by Hind III and Xba I double digestion. The linearized plasmid was then treated with Klenow fragment of DNA polymerase I to generate blunt ends and self-ligated to form a new plasmid, in which XbaI site was restored while Hind III was gone. By using this restored XbaI site, a Nhe I DNA fragment of AtPK220 promoter was cloned upstream of HP-At(270) and HP-At(150) sequence to produce the final plasmids of $P_{PK}$-HP-At(270)PK220 and $P_{PK}$-HP-At(150) PK220. AtPK220 promoter sequence (SEQ ID NO:14) was amplified by PCR from *Arabidopsis* (Columbia) genome using primer pairs of SEQ ID NO:135/SEQ ID NO:136.

$P_{4790}$-HP-At(270)PK220

To specifically down-regulate endogenous AtPK220, a strong root promoter $P_{4790}$ was identified and found to be highly expressed in the roots of *Arabidopsis*, particularly in the endodermis, pericycle, and stele. The $P_{4790}$ promoter is associated with a coding sequence identified as At2g44790 and the expression characteristics of $P_{4790}$ are similar to that of wild type AtPK220 expression. The $P_{4790}$ was used to replace the constitutive 35S promoter in 35S-HP-At(270) PK220. The promoter of At2g44790 was amplified using *Arabidopsis* (Col) genomic DNA as template and primers SEQ ID NO:151 and SEQ ID NO:152. The amplified promoter fragment has the length of 1475 base-pairs right upstream the ATG start codon of At2g44790 according to TAIR annotation. The 1475 bp-$P_{4790}$ fragment is identified a SEQ ID NO:150. Hind III and Xba I restriction sites were introduced to the 5' and 3' end of the promoter fragment by primer design. The promoter sequence was then used to replace the 35S promoter in 35S-HP-At(270)PK plasmids by HindIII/XbaI double digestion, which resulted in the final constructs of pBI-P4790-HP-At(270)PK.

Down-Regulation of BnPK220 in *Brassica* using RNAi 35S-HP-Bn(340)PK

To down-regulate the AtPK220 homolog in *Brassica* species, a hairpin construct was made using a 338 bp fragment of BnPK220 (SEQ ID NO;153) as the sense and anti-sense portions, and pBI300tGUS as the vector. Two pairs of primers SEQ ID NO:154 and SEQ ID NO:155; and SEQ ID NO:156 and SEQ ID NO:157 with unique restriction sites were designed according to BnPK220 sequence. A PCR fragment of 338 bp in length was amplified using *Brassica napus* cDNA as the template and the two pairs of primers, respectively. The SacI fragment was then inserted into pBI300tGUS at the SacI site downstream of the tGUS spacer in an antisense orientation. The resulting plasmid was subsequently used for cloning of a XbaI-BamI fragment in a sense orientation at the XbaI and BamHI sites. The vector pBI121tGUS was modified within the NPT II selectable marker gene and named pBI300. The NPT II gene in the vector pBI121 contains a point mutation (G to T at position 3383, amino acid change E182D). To restore the gene with its WT version, the NheI-BstBI fragment (positions 2715-3648) was replaced with the corresponding NheI-BstBI fragment from plasmid pRD400 (PNAS, 87:3435-3439, 1990; Gene, 122:383-384, 1992).

$P_{4790}$-HP-Bn(340)PK

The $P_{4790}$ promoter of At2g44790 was used to control expression of a hairpin construct to down-regulate endogenous BnPK220 in *Brassica*. The plasmid of 35S-HP-Bn (340)PK was digested with HindIII and XbaI to replace the 35S promoter with the $P_{4790}$ promoter.

Down-Regulation of PK220 by Antisense

The construct 35S-antisenseAtPK220 was made to down-regulate expression of AtPK220 via antisense. The antisense fragment was generated using PCR and the primer pair SEQ ID NO:106/SEQ ID NO:113. The synthesised product was digested with BamHI and XbaI to yield a 1177 bp sequence comprising 1160 bp of AtPK220 (SEQ ID NO:11). Included at the 5' end were 10 bp of intron sequence and at the 3' end, 7 bp of 3' UTR sequence, which were retained from the PCR primers. The 1177 bp fragment was cloned in an antisense orientation to the 35S promoter in pBI121w/o GUS at the BamHI and XbaI.

Down-Regulation of PK220 by AmiRNA

An artificial microRNA (amiRNA) construct was also made to down-regulate the expression of AtPK220 in *Arabidopsis*. An *Arabidopsis* genomic DNA fragment containing microRNA319a gene (SEQ ID NO:148), was amplified by PCR using *Arabidopsis* (Col) genomic DNA as template and primers listed as SEQ ID NO:141 and SEQ ID NO:142. The backbone of miR319a was then used to construct amiRPK220 (SEQ ID NO:149), in which a 21 bp fragment of miRNA319a gene in both antisense and sense orientations was replaced by a 21 bp DNA fragment of AtPK220 using recombinant PCR. Three pairs of primers: SEQ ID NO:141/ SEQ ID NO:144; SEQ ID NO:143/SEQ ID NO:146 and SEQ ID NO:145/SEQ ID NO:142 were designed for the construction. The final PCR product was digested with BamHI and XbaI, and subsequently cloned into pBI121w/o GUS for transformation into *Arabidopsis* or other plant species of choice.

Inhibition of PK220 Via Dominant-Negative Strategy 35S-AtPK220L292F

For expression of a non-functional AtPK220 sequence the AtPK220L292F from hwe116 was PCR amplified by RT-PCR using forward and reverse primers SEQ ID NO:118 and SEQ ID NO:110. The PCR product was digested with the restriction enzymes BamHI and XbaI (SEQ ID NO:121) and ligated into the binary vector pBI121w/o GUS. The sequence of SEQ ID NO:121 comprises the AtPK220L292F open reading frame (SEQ ID NO:3) and an additional 3 bp at the 5' end and 7 bp at the 3' end that are derived from UTR sequences (SEQ ID NO:121). The final construct, 35S-AtPK220L292F, was used to generate *Arabidopsis* and *Brassica* transgenic plants that were advanced to homozygosity for physiology assessment. Additionally, the vector is used to transform a plant species of choice and can be a dicot or a monocot.

$P_{4790}$-AtPK220L292F

The HindIII-XbaI fragment of the root promoter $P_{4790}$ was used to replace 35S promoter in pBI300, and then AtPK220L292F sequence was put downstream $P_{4790}$ by XbaI and BamHI digestion to generate the $P_{4790}$-driven dominant-negative construct. The resulting plasmid was then used for *Brassica* transformation. Additionally, the vector is used to transform a plant species of choice and can be a dicot or a monocot.

Down-Regulation of AtPK220 Homologs in a Monocot Species Using RNAi $P_{BdUBQ}$-HP-Bd(272)PK An expression cassette was constructed and inserted into two different vector backbones, the first being into the PacI-AscI sites of pUCAP and the second being into the PacI-AscI sites of pBF012. pBF012 is identical to pBIN-PLUS/ARS except that the potato-Ubi3 driven NPTII cassette has been excised via FseI digestion followed by self-ligation.

*Brachypodium distachyon* PK220 (BdPK220) was amplified using primer combinations SEQ ID NO:158 (bWET XbaI F) plus SEQ ID NO:159 (bWET BamHI R) having XbaI or BamHI sites respectively in the primers and SEQ ID NO:158 (bWET XbaI F) plus SEQ ID NO:160 (bWET ClaI R) having XbaI or ClaI sites respectively in the primers. PCR products were digested with the indicated restriction enzymes giving a 272 bp fragment (SEQ ID NO:161).

The hairpin spacer sequence, BdWx intron 1 (SEQ ID NO:164), was amplified with SEQ ID NO:162 (bWx BamHI F) plus SEQ ID NO:163 (bWx ClaI R) primers having BamHI or ClaI sites respectively in the primers and digested with the indicated restriction enzymes. The *B. distachyon* Wx gene is a homologue of the rice GBSS waxy gene, although the introns show little conservation.

The three fragments were ligated together into the XbaI site of the pUCAP MCS resulting in BdWx intron 1 sequence being flanked by Bd(272)PK220 target sequences in opposite orientations. The *B. distachyon* ubiquitin (BdUBQ) promoter contains an internal BamHI site, so the RNAi cassette was amplified with primers SEQ ID NO:200 (bWET BamHI end1) and SEQ ID NO:165 (bWET BamHI end2) which create BamHI cohesive ends without the need for BamHI digestion. The BamHI RNAi fragment was then ligated into the BamHI site of pUCAP already containing BdUBQ promoter and BdUBQT terminator resulting in the intermediate clone pBF067. The pBF067 complete insert was amplified with SEQ ID NO:166 (BdUBQ PvuI F) and SEQ ID NO:167 (BdUBQT PacI R), digested with PvuI and PacI and subsequently ligated into the PacI site of pUCAP or pBF012 vectors already containing a BdGOS2 driven mutant NPTII selectable marker in the AscI-PacI sites, resulting in pBF108 and pBF109, respectively. This mutant NPTII gene is commonly found in cloning vectors. There is only a single base pair difference from the wild type.

This cassette is in the PacI-AscI sites of pUCAP for the shuttle/bombardment vector pBF108 and in the Pac-AscI sites of pBF012 for the binary vector pBF109.

$P_{BdUBQ}$-HP-Pv(251)PK

An expression cassette was constructed and inserted into two different vector backbones, the first being into the PacI-AscI sites of pUCAP and the second being into the PacI-AscI sites of pBF012. A fragment of *Panicum virgatum* PK220 being 251 bp in length (Pv(251)PK220) and identified as SEQ ID NO:168 was amplified using primer combinations SEQ ID NO:169 (PvWET XbaI F) plus SEQ ID NO:170 (PvWET BamHI R) and SEQ ID NO:169 (PvWET XbaI F) plus SEQ ID NO:171 (PvWET ClaI R). PCR products were digested with the indicated restriction enzymes. No sequence information exists regarding the PvWx intron 1 so the BdWx intron 1 was used as the spacer sequence in this construct. This sequence was amplified with SEQ ID NO:162 (bWx BamHI F) plus SEQ ID NO:163 (bWx ClaI R) primers and digested with the indicated restriction enzymes.

The three fragments were then ligated together into the XbaI site of the pUCAP MCS resulting in BdWx intron 1 sequence being flanked by Pv(251)PK220 target sequences in opposite orientations. No PvUBQ promoter sequence was available so the BdUBQ promoter and terminator are used in this construct. The BdUBQ promoter contains an internal BamHI site, so the RNAi cassette was amplified with primers SEQ ID NO:172 (PvWET BamHI end1) and SEQ ID NO:173 (PvWET BamHI end2) which create BamHI cohesive ends without the need for BamHI digestion. The BamHI RNAi fragment was then ligated into the BamHI site of pUCAP already containing BdUBQ promoter and BdUBQT terminator resulting in the intermediate clone pBF152. The pBF152 complete insert was amplified with SEQ ID NO:166 (BdUBQ PvuI F) and SEQ ID NO:167 (BdUBQT PacI R), digested with PvuI and PacI and subsequently ligated into the PacI site of pUCAP or pBF012 vectors already containing BdGOS2 driven wildtype NPTII in the AscI-PacI sites, resulting in pBF169 and pBF170, respectively.

$P_{SbUBQ}$-HP-Sb(261)PK

An expression cassette was constructed and inserted into two different vector backbones, the first being into the PacI-AscI sites of pUCAP and the second being into the PacI-AscI sites of pBF012. A fragment of *Sorghum bicolor* PK220 (SbPK220) being 261 bp in length (Sb(261)PK220) and identified as SEQ ID NO:174 was amplified using primer combinations SEQ ID NO:175 (SbWET XbaI F) plus SEQ ID NO:176 (SbWET BamHI R) and SEQ ID NO:175 (SbWET XbaI F) plus SEQ ID NO:177 (SbWET ClaI R). PCR products were digested with the indicated restriction enzymes to give a Sb(261)PK220 fragment. The hairpin spacer sequence, SbWx intron 1 (SEQ ID NO:178), was amplified with primers SEQ ID NO:179 (SbWx BamHI) plus SEQ ID NO:180 (SbWx ClaI R) and digested with the indicated restriction enzymes. The three fragments were then ligated together into the XbaI site of the pUCAP MCS resulting in SbWx intron 1 sequence being flanked by SbWET target sequences in opposite orientations. BamHI cohesive ends were added to the RNAi cassette via amplification with primers SEQ ID NO:181 (SbWET BamHI end1)and SEQ ID NO:182 (SbWET BamHI end2). The BamHI RNAi fragment was then ligated into the BamHI site of pUCAP already containing SbUBQ promoter and SbUBQT terminator resulting in the intermediate clone pBF151. The pBF151 complete insert was amplified with SEQ ID NO:192 (SbUBQ PvuI F) and SEQ ID NO:167 (BdUBQT PacI R), digested with PvuI and PacI and subsequently ligated into the PacI site of pUCAP or pBF012 vectors already containing BdGOS2 driven wildtype NPTII in the AscI-PacI sites, resulting in pBF158 and pBF171, respectively.

A SbGOS2 promoter was identified from the *Sorghum* genome sequence was amplified and using the primer pair SEQ ID NO:184 (SbGOS2 HindIII F) and SEQ ID NO:185 (SbGOS2 HindIII R) a 1000 bp fragment of the GOS2 promoter, identified as SEQ ID NO:183, was PCR amplified and cloned using the HindIII restriction sites.

A SbUBQ promoter was identified from the *Sorghum* genome sequence was amplified and using the primer pair SEQ ID NO:187 (SbUBQ PstI F) and SEQ ID NO:188 (SbUBQ PstI R) a 1000 bp fragment of the UBQ promoter, identified as SEQ ID NO:186, was PCR amplified and cloned using the PstI restriction sites.

A SbUBQ terminator was identified from the *Sorghum* genome sequence was amplified and using the primer pair SEQ ID NO:190 (SbUBQT KKpnI F) and SEQ ID NO:191 (SbUBQT KKpnI R) a 239 bp fragment of the UBQ terminator, identified as SEQ ID NO:189, was PCR amplified and cloned using the KKpnI restriction sites.

*Miscanthus giganteus* (MgPK220) RNAi

Expression constructs designed to down regulate via a hairpin strategy can be devised following the same strategy as described above. Resulting in a construct that may comprise the following elements, a BdGOS2-wtNPTII-BdUBQT selectable marker cassette and a BdUBQ-(MgPK220 hairpin-RNAi cassette)-BdUBQT in a vector of choice such as pUCAP and pBF012

AtPK220 Promoter Isolation and Cloning

The AtPK220 promoter was isolated using a PCR approach using *Arabidopsis* (Columbia ecotype) genomic DNA as template. The 5' primer, SEQ ID NO:119, was designed near the adjacent gene and the 3' primer, SEQ ID NO:120, located 25 bp upstream of the ATG start codon of the AtPK220 gene. The amplified product was digested with BamHI and SmaI and cloned into pBI101. The digested fragment, SEQ ID NO:14, was 1510 bp in length. The resulting construct was named $P_{AtPK220}$-GUS.

AtPK220 Promoter Activity Analysis Using GUS Assay $P_{AtPK220}$-GUS was transformed into *Arabidopsis* plants using flower dipping, and the transgenic plants were advanced to T3 homozygosity. Various tissues including young seedlings and leaves, stems, flowers, siliques, and roots from T3 flowering plants were collected, stained in X-Gluc solution at 37 C overnight, de-stained with ethanol solution, and examined under a microscope. The results showed that the promoter of AtPK220 was expressed mainly in endodermis and pericycle cells of root tissue and was also found in leaf trichomes and seed coat of developing seeds. Of significance was the observation that expression of $P_{AtPK220}$-GUS was suppressed by water stress.

Sub-Cellular Localisation of AtPK220 Proteins in *Arabidopsis*

Expression of a full length wild type AtPK220-GFP fusion protein in transgenic *Arabidopsis* was used to locate the sub-cellular localization of the native protein. The primer pair SEQ ID NO:109 and SEQ ID NO:110 produced a fragment that was digested with SmaI and BamHI to yield a fragment comprising the full length open reading frame of AtPK220 and is disclosed as SEQ ID NO:10 and cloned downstream, in frame with the green fluorescence protein (GFP) in a pEGAD plasmid at the SmaI and BamHI sites. Additionally, the AtPK220 coding sequence was amplified using primer pair SEQ ID NO:198 and SEQ ID NO:199 and inserted upstream and in frame with GFP by AgeI digestion of pEGAD plasmid and the amplified AtPK220 fragment.

The 35S-GFP-AtPK220 and 35S-AtPK220-GFP constructs were transformed into *Arabidopsis* plants and homozygous transgenic plants (root tissues) were used for visual screening of GFP signal under confocal microscope. Green fluorescence was detected along plasma membrane, suggesting that AtPK220 protein was associated with plasma membrane in roots and that AtPK220 possibly functions as receptor kinase to sense or transduce environmental signals.

Isolation of BnPK220 from *Brassica napus* by 5' and 3' RACE

To isolate the homologous gene of AtPK220 from canola, a blast search (BLASTn) of NCBI Nucleotide Collection (nr/nt, est) and TIGR (DFCI) *Brassica napus* EST Database was done using AtPK220 sequence. Based on the sequences with highest similarity, a pair of primers, SEQ ID NO:122 and SEQ ID NO:123 were designed and used to PCR amplify a partial fragment of BnPK220. Both mRNA and genomic DNA isolated from *Brassica* leaves were used as template for these amplifications. A DNA fragment of about 500 bp was obtained by PCR from canola genomic DNA template. Sequence analysis of this PCR product showed that it shares a high identity with AtPK220 in nucleotide sequence as well in the intron organisation.

Based on the partial sequence of BnPK220, 5' and 3' RACE was performed to isolate the full length BnPK220 cDNA. For 3' RACE a forward primer, SEQ ID NO:124 and a nested primer, SEQ ID NO:125, were used. For 5' RACE a reverse primer, SEQ ID NO:126, and its nest primer, SEQ ID NO:127, were designed. RACE-ready cDNA for either 5' RACE or 3' RACE was made from RNA isolated from young *Brassica* leaves.

The 5' RACE yielded an amplified DNA of about 650 bp in length; and 3' RACE yielded a DNA of about 1 kb in size. Sequencing of these two RACE fragments showed high sequence similarity with AtPK220. A full-length mRNA of BnPK220 sequence was assembled by combining 5'RACE, partial BnPK220 fragment and 3' RACE results.

A full length BnPK220 cDNA was amplified by RT-PCR using the PCR primers SEQ ID NO:128 and SEQ ID NO:129. This cDNA comprises an ORF of 1302 nucleotides (SEQ ID NO:25) and encodes a protein of 433 amino acids (SEQ ID NO:26). Another full length BnPK220 cDNA was also amplified by the RT-PCR using cDNA made from *B. napus*. This cDNA (SEQ ID NO: 193) is 98.6% identical to SEQ ID NO:25, and encodes a protein (SEQID NO:194) of 99.3% identical to SEQ ID NO:26.

Isolation of Full-Length GmPK220 from Soybean by 5' RACE

A Blastn search of NCBI EST database, a homolog of AtPK220 was found as a soybean (*Glycine max*) EST, CX709060.1. From this homolog, a unigene cluster of 13 ESTs was retrieved from a soybean EST database. A contig was then assembled from these 13 ESTs, which covers a majority of the gene sequence.

The full-length sequence of GmPK220 (SEQ ID NO:41) was determined by combining the assembled contig, 5' RACE and 3' RACE results. The 5' RACE was performed using the primers of SEQ ID NO:130 for primary RACE PCR and SEQ ID NO:131 for nested RACE PCR. The 3' RACE was performed using the primers of SEQ ID NO:137 for primary RACE PCR and SEQ ID NO:138 for nested RACE PCR. GmPK220 encodes a protein as shown in SEQ ID NO:42.

Isolation of OsPK220 (Rice) Sequence by Database Mining

The rice genome (*Oryza sativa*, japonica cultivar) has been completely sequenced and is publically available. The homolog of AtPK220 in rice was determined by BLAST search of a rice EST database and by BLASTP search of a genomic sequence database. The target having the highest score was identified as Accession number Os05g0319700.

Os05g0319700 is abbreviated as OsPK220, and disclosed as SEQ ID NO:59, which encodes a protein disclosed as SEQ ID NO:60.

Isolation of ZmPK220 (Corn) Sequence

Two candidate homologs were found by BLAST search of the TIGR EST database, one a unigene Accession number TC333547 and the second Accession number CO439063.

Accession number TC333547 is 2125 nucleotides in length and contains an open reading frame of 1377 nucleotides (SEQ ID NO:77) encoding a protein of 458 amino acids (SEQ ID NO:78). This translated protein is full-length and is larger than AtPK220 protein. The C-terminal kinase domain is highly conserved between the *Arabidopsis* and corn protein sequence, however, the N-terminal sequence is more variable.

CO439063 is a short EST sequence and is missing 5' terminal sequence. The missing sequence was obtained by RACE methods. Two 5' RACE primers were designed based on the alignment between AtPK220 and CO439063. The primary 5' RACE primer is SEQ ID NO:132 and the nested 5' RACE primer is SEQ ID NO:133. The 3' RACE was also performed using the primers of SEQ ID NO:139 for primary RACE PCR and SEQ ID NO:140 for nested RACE PCR. The ZmPK220 (SEQ ID NO:79) sequence was assembled based on 5' RACE, 3' RACE results and CO439063 EST sequences. The corresponding protein sequence was listed as SEQ ID NO:80.

Sequence analysis shows that CO439063 has higher sequence similarity with rice OsPK220 than TC333547.

Isolation of BdPK220 Sequence from *Brachipodium distachyon* (Bd)

*Brachipodium* is one of the model monocot plants for functional genomic research. A contig was assembled from public ESTs or GSSs, and it covers a 3'portion of BdPK220 according to homologue alignment. RACE using Bd81RAR1 primer (SEQ ID NO: 195) and Bd81RAR2 primer (SEQ ID NO: 196) designed from the contig and using *Brachipodium* leaf cDNA produced a unique fragment of about 650 bp. The assembling of the RACE sequence and the contig gave the full length BdPK220 sequence (SEQ ID NO:24), which encodes a protein of 461 amino acids (SEQ ID NO: 197).

Determination of GsPK220 (Cotton) Sequence by Database Mining

A BLAST search of a cotton (*Gossypium*) TIGR-EST database identified a sequence cluster identified as Accession number TC79117, that has high similarity with AtPK220. This cluster has two overlapping ESTs, TC79117 which is referred herein as GsPK220) and consists of an open reading frame of 1086 nucleotides (SEQ ID NO:81). The largest open reading frame encodes a protein of 361 amino acids (SEQ ID NO:82).

Drought Tolerant Phenotype of hwe116 Mutant Found Under Water Limited Conditions and High Water Use Efficiency Under Both Drought and Optimal Conditions Two groups of plants were grown (5 plants per 3" pot filled with the same amount of soil-less mix) under optimal conditions in a growth chamber (22 C, 18 hr light, 150 uE, 70% relative humidity) until first day of flower (n=6 per entry per treatment). At first flower all plants were supplied with the same amount of water (optimal levels) but one group of plants was used for the optimal treatment and the other for drought treatments. In the optimal treatment the pots were weighed daily to determine daily water loss and then watered back up to optimal levels. In the drought treatment, pots were weighed daily to determine water loss and allowed to dry out. Plants were harvested on days 0, 2 and 4 of drought and optimal treatments for shoot biomass determinations. Lower water loss relative to shoot dry weight (DW) as compared to control, under drought conditions indicates a drought tolerant phenotype. The ratio of shoot dry weight accumulated to water lost during the treatment period provides a measure of water use efficiency (WUE). The hwe116 plants were delayed in flowering by 1 to 2 days. Water loss relative to shoot biomass was significantly lower (by 22%) in hwe116 than parent control under drought conditions. This result indicates that the mutant is drought tolerant. It has also been found that under optimal conditions the water loss relative to shoot DW was also significantly lower in the mutant (by 41%) as compared to the parent control. This result is consistent with higher water use efficiency phenotype. Calculations of water use efficiency showed that under both drought (Table 1) and optimal (Table 2) conditions hwe116 mutant uses water more efficiently because it accumulated more shoot biomass with less water (drought) or the same amount of biomass with less water (optimal).

TABLE 1

Water Use Efficiency (WUE) under drought conditions

| Entry | shoot DW accumulated- day 0 to 4 (g) | water lost - day 0 to 4 (g) | WUE (g shootDW acc/ kg water lost) |
|---|---|---|---|
| hwe116 | 0.146 | 56.5 | 2.58 (+13%) |
| Parent | 0.134 | 58.6 | 2.28 |

TABLE 2

Water Use Efficiency (WUE) under optimal conditions

| entry | shoot DW accumulated- day 0 to 4 (g) | water lost - day 0 to 4 (g) | WUE (g shootDW acc/ kg water lost) |
|---|---|---|---|
| hwe116 | 0.276 | 92.3 | 2.99 (+22%) |
| Parent | 0.271 | 110.6 | 2.45 |

The final result of enhanced water use efficiency in the mutant is greater shoot DW biomass as shown in Table 3 (harvested on day 4 from 1$^{st}$ flower).

TABLE 3

| | Final shoot DW biomass | | | |
|---|---|---|---|---|
| | Drought - shoot DW (g) | | Optimal - shoot DW (g) | |
| entry | Mean | S.E. | Mean | S.E. |
| hwe116 | 0.354 | 0.014 | 0.449 | 0.017 |
| parent | 0.300 | 0.011 | 0.414 | 0.011 |
| hwe116 as % of parent | 118% | | 108% | |

The hwe116 Mutant Maintains Higher Soil Water Content During Drought Treatment, Reaches Water-Stress Conditions Later and Shows Yield Protection Following Drought Stress During Flowering Relative to Control Plants.

An experiment was set up with 5 plants per 4" pot filled with the same amount of soilless mix. Two groups of plants (optimal and drought) were grown under optimal conditions in a growth chamber (22 C, 18 hr light, 150 uE, 70% relative humidity) until first day of flower (n=9 per entry and per group). At first flower all plants were supplied with the same amount of water and further water was withdrawn for the drought treated group of plants. The optimal group was watered daily as before. Pots in the drought treated group were weighed daily for 6 days of treatment to determine soil water content. After 6 days of drought treatment plants were re-watered and allowed to complete their lifecycle as the optimal group under optimal conditions. At maturity the seeds were harvested from each pot and the seed yield was determined for both optimal and drought treated plants. The results of changes in soil water content during the drought treatments were determined. Soil water content was measured as percentage of initial amount of water in the pot. The results indicate that the mutant was able to retain water in pots longer and therefore it reached the stress level (around 25% soil water content) 1 day later and wilted 1 day later than control. This treatment caused a yield reduction of 17% from optimal levels in the mutant, whereas in control the yield reduction was 41%. Therefore the mutant demonstrated a yield protection of 24% relative to control, following a drought treatment.

The hwe116 Mutant Seedlings Showed Less Sensitivity to Cold Stress.

Two groups of plants with 8 replicates per entry were grown with 3 plants per 3" pot under optimal conditions of 22° C. and short days to prolong vegetative growth and delay flowering (10 hr light 150 uE, and 14 hr dark), 70% relative humidity in a growth chamber. At 10 days of age (3 days post-transplanting of seedlings into soil from agar plates) the cold treatment group was placed in a chamber at 8° C. for 11 more days of growth while the optimal group was maintained at 22° C. Plants were harvested for shoot dry weight (DW) determinations at 21 days of age. The results are shown in Table 4. The hwe116 mutant had smaller seedlings under optimal conditions than those of controls but after cold exposure the shoot DW was equivalent to that of the parent and as percentage of the optimal DW it was higher than that of both controls by 9 and 15% indicating that the growth of the mutant was not as inhibited by cold as that of controls.

TABLE 4 shoot dry weight under optimal and cold conditions.

| | optimal (22° C.) | | Cold (8° C.) | | |
|---|---|---|---|---|---|
| | shoot DW (mg) | | shoot DW (mg) | | shoot DW |
| Entry | Mean | S.E. | Mean | S.E. | % of optimal |
| hwe116 | 6.65 | 0.30 | 2.85 | 0.13 | 43% |
| parent | 9.16 | 0.21 | 2.58 | 0.11 | 28% |
| WT | 9.30 | 0.20 | 3.18 | 0.21 | 34% |

The hwe116 Mutant has Thicker Leaves and Higher Chlorophyll Content Per Leaf Area. The Mutant Showed Delayed Leaf Senescence and Resistance to Oxidative Stress.

Plants were grown 1 per 3" pot under optimal growth conditions in a growth chamber (16 hr light, 300 uE, 22° C., 70% relative humidity). Early into flowering three leaf disks (86.6 um2 each) were taken from three youngest fully developed leaves and placed in petri dishes containing filter paper with 5 uM N,N'-Dimethyl-4,4'-bipyridinium dichloride (paraquat) solution as an oxidizing agent. Plates with leaf disks were placed under continuous light of 150 uE for 25 hours. This resulted in chlorophyll bleaching. The differences between the mutant and controls in the extent of bleaching were quantified by measuring chlorophyll content of the leaf disks. A leaf disk was also removed from leaves that have not been exposed to paraquat treatment and optimal chlorophyll content was determined. These disks were also weighed. The results showed that the mutant had higher total chlorophyll content per leaf surface area (Table 5), however the leaves of this mutant are thicker (leaf disks were 15 to 24% heavier in the mutant compared to those of controls). Chlorophyll content per gram of fresh leaf tissue was, therefore, not different. There were no differences between chlorophyll a to b ratios between the mutant and controls. The hwe116 mutant showed resistance to the oxidative stress as indicated by 5 to 7% higher chlorophyll content following paraquat treatment (Table 5). Leaf senescence was also delayed in the hwe116 mutant (data not shown).

TABLE 5

Effect of oxidative stress on chlorophyll content of leaves.

| | Optimal | | 5 uM paraquat in 24 hr light | | |
|---|---|---|---|---|---|
| | Chl (a + b) - (mg/m2) | | Chl (a + b) - (mg/m2) | | % of |
| Entry | Mean | Std Err | Mean | Std Err | opt |
| hwe116 | 303.7 | 6.7 | 67.9 | 4.4 | 20% |
| Parent | 259.6 | 4.3 | 39.5 | 5.9 | 15% |
| WT | 250.2 | 5.7 | 32.1 | 2.9 | 13% |

The Growth of Mutant hwe116 Seedlings Showed Less Inhibition on Low Nitrogen Containing Media.

Twelve seedlings were grown on an agar plate (6 plates per entry) containing ½ MS growth media with optimal (20 mM) or low (0.3 mM) nitrogen content. Plates were placed in a growth room with an 18 hr light period (100 uE) for 6 days in a vertical position, then plates were placed horizontally and seedlings were grown for another 4 days before the shoots were harvested. The average seedling shoot DW after 10 days of growth was calculated per plate. The results are shown in Table 6. The shoot DW of hwe116 mutant grown under optimal conditions was significantly reduced but when grown on low nitrogen there were no differences. The shoot DW on low nitrogen in the mutant was 3 to 7% greater than in controls when compared to the optimal nitrogen levels. This indicates that the mutant may have better nitrogen use efficiency.

TABLE 6

Effect of nitrogen on seedling shoot DW

| | Average seedling shoot DW (mg) | | | | |
|---|---|---|---|---|---|
| | Optimal nitrogen | | Low nitrogen | | |
| Entry | Mean | S.E. | Mean | S.E. | % Opt |
| hwe116 | 1.03 | 0.03 | 0.23 | 0.01 | 22 |
| Parent | 1.34 | 0.04 | 0.20 | 0.01 | 15 |
| WT | 1.22 | 0.03 | 0.23 | 0.02 | 19 |

Knockout Mutant of PK220 Showed Drought Tolerant Trends and Higher Water Use Efficiency Under Drought Treatment.

Plant lines obtained from the SALK institute that were T-DNA knockouts in the AtPK220 gene (SALK_147838) were grown (5 per 3"pot) under optimal conditions in a growth chamber (18 hr light, 150 uE, 22° C., 60% relative humidity) until first open flower (n=8 per entry and per harvest). The drought treatment was started by watering all plants with the same amount of water and cessation of further watering. Pots were weighed daily and plants were harvested for shoot DW determinations on days 0, 2 and 4 of the drought treatment. The result showed that water lost from pots in 2 days relative to shoot DW on day 2 was significantly lower (by 13%) for the knockout mutant and its shoot DW was also significantly greater (by 24%) on day 2 as compared to control wild-type. This result is consistent with drought tolerant phenotype.

The results showed that the water use efficiency of the knockout mutant was greater than that of the control-WT as the knockout mutant was able to accumulate more shoot biomass in the 2 days of treatment while using the same amount of water as control (Table 7).

TABLE 7

Water use efficiency under drought treatment

| entry | g water lost | g shoot DW gain | WUE (g shoot/kg water) |
|---|---|---|---|
| PK220-knockout | 43.1 | 0.059 | 1.37 |
| WT | 42.9 | 0.035 | 0.82 |

Transgenic Lines of 35S-HP-At(270)PK220 Construct in *Arabidopsis* Showed Drought Tolerance.

Plants were grown (5 per 3" pot and 8 pots per entry per harvest) under optimal conditions in a growth chamber (18 hr light, 150 uE, 22° C., 60% relative humidity) until first day of flower. The drought treatment was started by watering all pots with the same amount of water and cessation of further watering. Pots were weighed daily for water loss determinations and plants were harvested for shoot biomass on day 4 of drought treatment. The results (Table 8) showed that 11 out of 13 transgenic lines demonstrated a drought tolerant phenotype (having a lower water loss over 2 days relative to shoot biomass on day 4). Four of the lines showed a slight delay in flowering (1 day), as did the hwe116 mutant. The final shoot biomass on day 4 was greater for most of the transgenic lines as compared to control WT. These results are indicative of a drought tolerant phenotype in the transgenic lines down-regulated in PK220 expression. As examples, the reduction in expression level of AtPK220 for the top 3 performing lines: 65-4, 38-5, and 59-3, are 75%, 47% and 58%.

TABLE 8

Drought tolerance and shoot DW (day 4) for 35S-HP-At(270)PK220 transgenic lines relative to wild type (WT) and the hwe116 mutant relative to parent control.

| entry | drought tolerance % of control | shoot DW % of control |
|---|---|---|
| 65-4 | 119% | 132% |
| 38-5 | 116% | 124% |
| 59-3 | 112% | 119% |
| 33-7 | 111% | 114% |
| 54-11 | 108% | 115% |
| 56-3 | 107% | 115% |
| 43-11 | 107% | 113% |
| 23-8 | 106% | 111% |
| 12-2 | 106% | 110% |
| 63-4 | 104% | 110% |
| 32-1 | 104% | 109% |
| 30-3 | 101% | 104% |
| 74-2 | 101% | 107% |
| WT | 100% | 100% |
| hwe116 | 186% | 106% |
| parent | 100% | 100% |

Drought Tolerance of 35S-HP-At(270)PK220 Transgenic Lines in *Arabidopsis* and Enhanced Water Use Efficiency were Confirmed.

The transgenic lines of 35S-HP-At(270)PK220 were grown with 5 per 3" pot under optimal conditions in a growth chamber (18 hr light, 150 uE, 22° C., 60% relative humidity) until first flower (n=8). Drought treatment was started at first flower by watering all the pots with the same amount of water and cessation of further watering. The pots were weighed daily for the 4 days of drought treatment and plants were harvested on days 0, 2 and 4 of treatment. The results confirmed that water lost in 2 days relative to shoot biomass on day 2 was lower in five transgenic lines relative to controls, confirming their drought tolerant phenotype (Table 9). The shoot DW on day 2 was greater in 5 of the transgenic lines.

TABLE 9

Drought tolerance and shoot DW for 35S-HP-At(270)PK220 transgenic lines

| entry | drought tolerance % of WT | shoot DW % of WT |
|---|---|---|
| 59-3 | 110% | 105% |
| 65-4 | 110% | 98% |
| 38-5 | 107% | 109% |
| 33-7 | 103% | 106% |
| 56-3 | 102% | 95% |
| 54-11 | 101% | 103% |
| null (65-1) | 99% | 99% |
| WT | 100% | 100% |

The water use efficiency was greater than that of controls during the 4 days of drought treatment for three transgenic lines and this enhanced water use efficiency was due to greater shoot DW accumulation (Table 10).

TABLE 10

Water use efficiency between day 0 and 4 of the drought treatment in transgenic lines of 35S-HP-At(270)PK220.

| entry | shoot DW accumulated (g) d 0-d 4 | water lost (g) d 0 to d 4 | WUE (g shoot/ kg water) d 0 to d 4 |
|---|---|---|---|
| 65-4 | 0.090 | 62.5 | 1.44 (+22 to 33%) |
| 12-2 | 0.079 | 62.2 | 1.27 (+7 to 17%) |
| 56-3 | 0.079 | 62.7 | 1.25 (+6 to 16%) |
| null (65-1) | 0.068 | 62.7 | 1.08 |
| WT | 0.073 | 61.9 | 1.18 |

Transgenic Lines of 35S-HP-At(270)PK220 in *Arabidopsis* had Lower Water Loss Relative to Shoot Biomass and Enhanced WUE Under Optimal Conditions.

Plants of 35S-HP-At(270)PK220 transgenic lines 65-7 and 59-5, WT Columbia, hwe116 mutant and its parent were grown (5 per 3" pot) under optimal conditions in a growth chamber (22° C., 18 hr light-200 uE, 60% relative humidity) until first flower (n=8 per entry, per harvest). At first flower all pots in the water limited group were watered with the same amount of water (to a pot weight of 120 g in first 4 days and to 130 g for last 3 days (as plants grew larger they required more water). Pots were weighed daily to determine daily water loss and plants were harvested on day 0 and day 7 of this treatment. Water use efficiency (WUE) was calculated from the ratio of shoot biomass accumulated to water lost. The results are shown in Table 11.

TABLE 11

Water Use Efficiency under optimal conditions

| entry | shoot DW accumulated (g) d 0-d 4 | water lost (g) d 0 to d 4 | WUE (g shoot/ kg water) d 0 to d 4 |
|---|---|---|---|
| 59-5 | 0.514 | 223 | 3.31 (+4%) |
| 65-4 | 0.671 | 276 | 2.43 (+9%) |
| WT | 0.517 | 232 | 2.23 |
| hwe116 | 0.420 | 191 | 2.19 (5%) |
| parent | 0.421 | 202 | 2.08 |

The results show that under optimal water conditions the two transgenic lines and the mutant had enhanced water use efficiency.

Growth Rates of the 35S-HP-At(270)PK220 Transgenic *Arabidopsis* Were Greater Than Those of Controls During Both Optimal and Water Limited Conditions.

Plants of 35S-HP-At(270)PK220 transgenic line 65-4 and WT Columbia were grown (5 per 3" pot) under optimal conditions in a growth chamber (22° C., 18 hr light-150 uE, 60% relative humidity) until first flower (n=8 per entry, per treatment and per harvest). At first flower all pots in the water limited group were watered with the same amount of water (to a pot weight of 95 g), and further watering was stopped for 2 days. It took 2 days for the water limited group of plants to reach about 30% of initial soil water content (about 55 g total pot weight), referred to as pre-treatment. At that time the water limited treatment was deemed to have started (day 0 of treatment) and plants were watered daily up to a total pot weight of 55 g for 3 days, and up to 65 g in the following 4 days (until day 7 of treatment). The optimal group was maintained under optimal conditions by watering the pots daily up to 100 g total pot weight in the 2 pre-treatment days, the first 3 days of treatment and then up to 130 g in the last 4 days of treatment (as plants grew larger they required more water). The daily water loss from the pots was measured for all the plants and plants in both groups were harvested on days 0, 1, 2, 3, 5, and 7 of treatment for shoot dry weight determinations. The water loss relative to the shoot biomass (drought tolerant phenotype) was calculated over the initial two days before the start of treatment, during the first 3 days of treatment and during the last 4 days of treatment. The results under both optimal (Table 12) and water limited (Table 13) conditions are shown. The transgenic line 65-4 lost less water relative to shoot biomass than WT in both optimal and water limited conditions. Under limited water conditions this is consistent with enhanced drought tolerance phenotype.

TABLE 12

Water loss in g/shoot DW in g under optimal conditions.

| Entry | pre-treatment | d 0-d 3 | d 3-d 7 |
|---|---|---|---|
| 65-4 | 231 ± 9 | 162 ± 3 | 237 ± 5 |
| WT | 275 ± 8 | 178 ± 7 | 243 ± 6 |

TABLE 13

Water loss in g/shoot DW in g and Drought tolerance (as percentage of WT) under water limited conditions.

| Entry | pre-treatment (drought toler. in % of WT) | d 0-d 3 (drought toler. in % of WT) | d 3-d 7 (drought toler. in % of WT) |
|---|---|---|---|
| 65-4 | 174 ± 2 (108%) | 83 ± 2 (115%) | 153 ± 6 (113%) |
| WT | 189 ± 4 (100%) | 97 ± 4 (100%) | 175 ± 4 (100%) |

Growth rates of the plants were calculated over the seven days of both treatments. The results showed that transgenic line 65-4 had larger plants (up to 24%) than the wild type throughout the treatment under both conditions. The growth rate (shoot dry weight accumulated per day over the 7 days of treatment) was slightly greater for the transgenic line under both optimal and water limited conditions (63.3 and 21.3 mg shoot/day, respectively) than that of WT control (58.3 and 20.4 mg shoot/day, respectively).

The Transgenic Line of 35S-HP-At(270)PK220 *Arabidopsis* and the hwe116 Mutant Grow Better Under Limited Nitrogen Conditions Than Controls.

The 35S-HP-At(270)PK220 transgenic line 65-5, its segregated null control (null 65-1) and wild-type (WT) plus the hwe116 mutant and its parent control were analyzed for growth characteristics of young seedling under optimal and limited nitrogen conditions. Nitrogen content refers to the available nitrogen for plant growth, including nitrate and ammonium sources. Seedlings were grown on agar plates (10 per plate and 5 plates per entry and per treatment) containing either optimal nutrients (including 20 mM nitrogen) or low (limiting to growth) nitrogen (optimal all nutrients except for nitrogen being 0.5 mM). Plates were placed in a growth chamber at 18 hr lights of 200 uE and 22° C. Seedlings were grown for 14 days before being harvested for shoot biomass (8 seedlings) and chlorophyll determinations (2 seedlings). On optimal plates there were no differences in average seedling shoot biomass except for the hwe116 mutant, as shown before had slightly smaller seedling shoot DW (not significant). On low nitrogen the hwe116 mutant had significantly bigger seedling shoot DW and showed 30% less inhibition in growth as compared to its parent. The transgenic line 65-5 showed slightly greater shoot DW than controls and was 5% to 7% less inhibited in growth than the controls (Table 14).

TABLE 14

Effect of nitrogen on seedling shoot DW

| | Average seedling shoot DW (mg) | | | | |
|---|---|---|---|---|---|
| | Optimal N (20 mM) | | Low N (0.5 mM) | | |
| entry | Mean | Std Err | Mean | Std Err | % of opt |
| 65-5 | 5.3 | 0.1 | 2.9 | 0.1 | 56% |
| WT | 5.5 | 0.3 | 2.8 | 0.1 | 51% |
| hwe116 | 4.8 | 0.2 | 3.8 | 0.3 | 80% |
| parent | 5.1 | 0.2 | 2.6 | 0.1 | 50% |

The total chlorophyll content of seedling shoots grown under low N levels reflected the shoot DW results. Chlorophyll content is very closely linked to available N and one of the major symptoms of N-deficiency in plants is leaf chlorosis or bleaching. Table 15 shows that chlorophyll content of the transgenic line 65-5 and the mutant hwe116 was reduced less than that of the controls.

TABLE 15

Effects of nitrogen on seedling shoot total chlorophyll content

| | seedling shoot chlorophyll content (ug/g) | | | | |
|---|---|---|---|---|---|
| | Optimal N (20 mM) | | Low N (0.5 mM) | | |
| entry | Mean | Std Err | Mean | Std Err | % of opt |
| 65-5 | 902 | 35 | 244 | 22 | 27% |
| WT | 854 | 102 | 156 | 17 | 18% |
| hwe116 | 1006 | 51 | 376 | 37 | 37% |
| parent | 836 | 59 | 208 | 47 | 25% |

These results confirmed that the hwe116 mutant grew better on limited nitrogen and the transgenic line showed the same trends. Therefore, down-regulation of the PK220 gene in plants appears to result in increased nitrogen use efficiency (accumulation of more biomass per unit of available nitrogen).

The Transgenic Line of 35S-HP-At(270)PK220 *Arabidopsis* and the hwe116 Mutant Germinate Faster and Have Higher Rates of Germination in the Cold.

Germination under cold (10° C.) conditions was assessed in the transgenic line 65-5 carrying the 35S-HP-At(270) PK220 construct relative to WT-control and that of the hwe116 mutant relative to its parental control on agar plates containing optimal growth media. Four plates per entry with 30 seeds each were prepared and placed in the chamber at 10° C., 18 hr light (200 uE). Germination (emergence of the radicle) scored as a percentage of viable seeds, was noted twice daily for 5 days starting with day 5 from placing of seeds on plates (no germination before day 5). Once no further changes were observed in germination all plates were placed in a chamber at 22° C. to check for viability of the seeds that had not germinated. All entries showed 98 to 100% seed viability, the hwe116 mutant had 94%. viability. The results of the germination assessment at 10° C. (Table 16) indicate that the transgenic line 65-5 germinated sooner than it's WT-control. The hwe116 mutant had higher rates of germination in the cold than its parent control. These data, together with the evidence that the mutant grows better under cold conditions are indicative of a greater seed and seedling vigor under cold stress

TABLE 16 percentage germination of viable seeds at 10° C.

| entry | #reps | \multicolumn{10}{c|}{Hours @ 10° C.} | % Viable Seed |
|---|---|---|---|---|---|---|---|---|---|---|---|---|
| | | 114.5 | 121 | 139 | 145 | 163 | 169 | 188.5 | 212.5 | 235 | 241 | |
| 65-5 | 4 | 15.1 | 32.8 | 75.7 | 80.7 | 90.0 | 90.8 | 90.8 | 92.5 | 93.3 | 94.2 | 99.2 |
| WT | 4 | 5.9 | 16.0 | 55.4 | 62.9 | 78.1 | 79.0 | 80.7 | 80.7 | 81.5 | 81.5 | 98.4 |
| hwe116 | 4 | 15.9 | 28.4 | 67.5 | 81.4 | 94.2 | 98.0 | 99.0 | 99.0 | 100.0 | 100.0 | 94.0 |
| Parent | 4 | 6.7 | 26.7 | 72.5 | 77.5 | 85.0 | 85.0 | 85.9 | 85.9 | 85.9 | 85.9 | 100.0 |

Gas Exchange Measurements Support Higher WUE in Transgenic 35S-HP-At(270)PK220 *Arabidopsis* Under Optimal Conditions Plants of two transgenic lines and WT were grown in four inch diameter pots (one per pot) under optimal conditions in a growth chamber at 18 hr light (200 uE), 22° C., 60% RH. Eight days from first open flower gas exchange measurements were made on the youngest, fully developed leaf of 10 to 11 replicates per entry. Photosynthesis and transpiration rates were measured inside the growth chamber at the ambient growth light and temperature conditions and 400 ppm carbon dioxide using Li-6400 and *Arabidopsis* leaf cuvette. From the ratio of photosynthesis to transpiration instantaneous water use efficiency (WUE) was calculated. The results are shown in Table 17. The WUE in the transgenic lines was 11 and 18% greater than that of the WT. This data is consistent with the WUE measurements over a period of few days using the ratio of biomass accumulated to water lost in transpiration.

TABLE 17

Photosynthesis (umol carbon dioxide/m2/s), transpiration (mmol H2O/m2/s) and WUE measured under optimal growth conditions.

| entry | Phots. (umol/m2/s) | Photos. (% WT) | Trans. (mmol/m2/s) | Trans. (% WT) | WUE (Photos/Trans) | WUE (% WT) |
|---|---|---|---|---|---|---|
| 59-6 | 3.9 ± 0.2 | 105% | 4.2 ± 0.5 | 95% | 1.03 ± 0.11 | 118% |
| 65-5 | 3.6 ± 0.2 | 97% | 3.8 ± 0.4 | 86% | 0.97 ± 0.13 | 111% |
| WT | 3.7 ± 0.2 | | 4.4 ± 0.2 | | 0.87 ± 0.05 | |

Drought Tolerance of 35S-HP-At(270)PK220 Transgenic *Arabidopsis* Results in Seed Yield and Biomass Protection Following Drought Stress.

Plants of two transgenic lines and the WT were grown (5 per 3 inch pot containing equal amount of soil) under optimal conditions in a growth chamber (22 C, 18 hr light of 200 uE, 60% RH) until first open flower. At first flower the drought treatment was applied to half of the plants while the other half was maintained under optimal conditions until maturity. The drought treatment consisted of watering all the plants to the same saturated water level. Plants were then weighed daily to monitor water loss from the pots and their water content was equalized daily by watering all pots to the level of the heaviest pot. As a result the soil water content was declining and reached stress levels with plants wilting on day 4. Plants were maintained at that stress level for another 2 days and on day 6 all plants were re-watered and maintained under optimal conditions for the rest of their life cycle. At maturity both optimal and drought plants were harvested for seed and shoot biomass. The impact of drought stress on both seed yield and shoot biomass was determined by comparing the optimal and drought treated plants. The results are shown in Table 18. Under optimal conditions the seed yield and the final shoot biomass of the transgenic lines was 7 to 10% higher than that of the WT. Following the drought stress during flowering the reduction in seed yield and the shoot biomass were not as great in transgenic plants as in the WT, resulting in seed yield protection of 5-7% and shoot biomass protection of 4%. The protection was calculated as the difference between the transgenics and WT in seed yield or shoot biomass a percentage of optimal.

TABLE 18

Seed yield and final shoot biomass from optimal and drought stressed plants, n = 10

| entry | Seed yield-opt (g) | Shoot DW-opt (g) | Seed yield-drought (g) | % of opt | Shoot DW-drought (g) | % of opt |
|---|---|---|---|---|---|---|
| 59-6 | 1.29 ± 0.05 | 2.96 ± 0.13 | 1.06 ± 0.03 | 82% | 2.37 ± 0.07 | 80% |
| 65-5 | 1.27 ± 0.03 | 2.89 ± 0.08 | 1.01 ± 0.02 | 80% | 2.32 ± 0.06 | 80% |
| WT | 1.18 ± 0.04 | 2.69 ± 0.10 | 0.89 ± 0.02 | 75% | 2.04 ± 0.05 | 76% |

Over-Expression of Wild Type AtPK220 in hwe116.2 Background can Restore the WT Phenotype Transgenic plants of 35S-AtPK220 (in hwe116.2) were grown (5 per 3 inch pot) under optimal conditions in a growth chamber as described above until the first open flower. Drought treatment was applied by watering all plants to the same saturated level. Further watering was withheld. Plants were weighed daily to determine the daily water loss and all plants were harvested on day 4 of treatment by which time all plants showed wilting. The water loss relative to final shoot biomass was used to calculate drought tolerance where that of WT was assumed at 100%. The data are shown in Table 19. Three transgenic lines showed a reduction in drought tolerance from the mutant levels as indicated by increased water loss relative to shoot biomass. The three transgenic lines also flowered earlier than the mutant line and similar to the time that the WT lines flowered. These results support the conclusion that the AtPK220 gene mutation in hwe116.2 is responsible for the altered phenotypes observed and expression of a WT gene restore the WT characteristics of a mutant plant.

TABLE 19

Water loss relative to shoot biomass and drought tolerance, n = 8

| entry | Days to flower | Water lost in 3 d/shoot DW d 4 | Drought tolerance (% of WT) |
|---|---|---|---|
| 28-4 | 20.9 ± 0.1 | 155.1 ± 3.1 | 111% |
| 2-4 | 21.8 ± 0.1 | 164.7 ± 2.4 | 105% |
| 7-11 | 21.6 ± 0.1 | 177.9 ± 4.4 | 97% |
| hwe116.2 | 23.1 ± 0.2 | 134.9 ± 3.6 | 117% |
| WT | 20.8 ± 0.2 | 173.4 ± 5.1 | 100% |

Down Regulation of AtPK220 with the AtPK220-Promoter ($P_{PK}$) in *Arabidopsis* Results in Enhanced Drought Tolerance of Plants

*Arabidopsis* plants of $P_{PK}$-HP-At(270)PK220 were grown (5 per 3 inch pot) under optimal conditions in a growth chamber as mentioned above until the first open flower. Drought treatment was applied then by watering all plants to the same saturated level. Further water was withheld. Plants were weighed daily to determine the daily water loss and all plants were harvested on day 4 of treatment (all plants were wilted). The water loss relative to final shoot biomass was used to calculate drought tolerance where that of WT was assumed at 100%. The results of this study are shown in Table 20.

TABLE 20

Water loss relative to shoot biomass and drought tolerance, n = 8

| entry | Days to flower | Water lost in 3 d/shootDW d 4 | Drought tolerance (% WT) |
|---|---|---|---|
| 14-04 | 22 | 158 ± 5 | 116% |
| 15-06 | 20 | 183 ± 8 | 104% |
| 45-3 | 20 | 185 ± 9 | 103% |
| WT | 20 | 190 ± 9 | 100% |

One of the transgenic lines, 14-04, showed significantly greater drought tolerance than the wild type control as indicated by lower water loss relative to shoot biomass. This result is supported by data from line 14-04 that showed nearly complete inhibition of PK220 gene expression. The expression of AtPK220 was reduced by nearly 96% in the roots compared to WT. These results indicate that down regulation of PK220 in the roots is sufficient to achieve significant drought tolerance phenotype and presumably enhanced water use efficiency.

Overexpression of *Brassica napus* PK220 in the *Arabidopsis* hwe116 Mutant Can Restore the WT Phenotype Transgenic plants of 35S-BnPK220 (in hwe116) plus two null controls (segregated siblings of the transgenic lines without the transgene, therefore hwe116 mutant) were grown (5 per 3 inch pot) under optimal conditions in a growth chamber as mentioned above until the first open flower. Drought treatment was applied then by watering all plants to the same saturated level. Further water was withheld. Plants were weighed daily to determine the daily water loss and all plants were harvested on day 4 of treatment (all plants were wilted). The water loss relative to final shoot biomass was used to calculate drought tolerance where that of WT was assumed at 100%. The results of this study are shown in Table 21. The results indicate that 6 lines had a reduction of 8% or more in drought tolerance as compared to the nulls (the hwe116 mutant background) and therefore restoration towards the WT phenotype. This indicates that BnPK220 is functional and can work in the *Arabidopsis*.

TABLE 21

Water loss relative to shoot DW and drought tolerance, n = 8

| entry | Water lost in 3 d/shoot DW d 4 | Drought tolerance (% of null) |
|---|---|---|
| 106-11 | 148 ± 6 | 98% |
| 67-6 | 150 ± 4 | 97% |
| 51-6 | 152 ± 4 | 96% |
| 5-1 | 152 ± 2 | 95% |
| 74-12 | 157 ± 5 | 92% |
| 38-7 | 160 ± 5 | 90% |

TABLE 21-continued

Water loss relative to shoot DW and drought tolerance, n = 8

| entry | Water lost in 3 d/shoot DW d 4 | Drought tolerance (% of null) |
|---|---|---|
| 70-2 | 161 ± 2 | 89% |
| 97-3 | 164 ± 5 | 87% |
| 31-6 | 165 ± 4 | 87% |
| 93-8 | 172 ± 4 | 82% |
| Null 38-10 | 146 ± 3 | 100% |
| Null 90-7 | 135 ± 5 | 107% |

Transgenic *Brassica* Lines having a 35S-AtPK220L292F Construct Showed Drought Tolerance and Higher Water Use Efficiency Down regulation of endogenous PK220 activity was demonstrated using a dominant negative strategy by expression of the mutant allele of the AtPK220 gene in *Brassica napus*. Three *Brassica napus* transgenic lines having the *Arabidopsis* mutant AtPK220L292F gene and one null control line (a segregated sibling of the transgenic line lacking the transgene) per line were grown in 4.5 inch diameter pots containing equal amounts of soilless mix (Sunshine Professional Organic Mix #7) under optimal conditions of 16 hr light (400 uE) and 22 C day/18 C night temperature. At the four leaf stage, two treatments were applied. In the optimal treatment plants were watered to saturation and pots were covered with plastic bags to prevent any water loss from the pots due to evaporation. These plants were weighed daily for 7 days to determine the water loss from the pots due to transpiration and the same amount of water was added back daily to each pot to maintain the plants under optimal water conditions. In the drought treatment all plants were watered to saturation levels. Pots were covered with plastic and were weighed daily. However, these pots were watered daily to the level of the heaviest pots. This treatment went for 7 days with the soil water content gradually reaching stress levels. Plants started to wilt by day 5. At the end of the 7 days both groups of plants were harvested for shoot biomass determinations.

Gas exchange measurements were done on drought treated plants of two transgenic lines plus their nulls on days 3 and 4 of the treatment. Photosynthesis and transpiration were measured on leaf 3 under steady state growth conditions of 400 uE light, 400 ppm carbon dioxide and 22 C using Li-6400. From the ratio of photosynthesis to transpiration, water use efficiency (WUE) was calculated. The drought treated plants were used to calculate the drought tolerance (as percentage of their nulls). This was done using the ratio of cumulative daily transpirational water loss between days 3 and 7, relative to the final shoot dry weight and normalizing it to the nulls (set at 100%).

The results in Table 22 indicate that transgenic lines had strong trends toward greater drought tolerance. This was a result of lower water loss relative to shoot dry weight, a phenotype present also under optimal conditions.

The gas exchange data (Table 23) showed that on both days 3 and 4 of the drought treatment the transgenic plants had slightly higher WUE than controls (4 to 16%).

Water use efficiency calculated from the ratio of photosynthesis to transpiration provides only a single point, instantaneous measurement rather than cumulative measurement over the period of treatment and as a result may be of lesser magnitude.

In conclusion, the data with transgenic 35S-AtPK220L292F *Brassica* plants indicate that water use efficiency technology is transferable to *Brassica* when using a AtPK220L292F gene from a heterologous species.

TABLE 22

Water loss between days 3 and 7 relative to final shoot dry weight under optimal and drought treatment. Drought tolerance (% of the appropriate null). n = 8

| entry | optimal - g water lost d 3-7/g shootDW d 7 | drought - g water lost d 3-7/g shootDW d 7 | Drought tolerance (% of null) |
|---|---|---|---|
| Tr-05 | 172 ± 6 | 121 ± 5 | 109% |
| Null-05 | 190 ± 4 | 133 ± 7 | 100% |
| Tr-27 | 194 ± 6 | 134 ± 7 | 113% |
| Null-27 | 205 ± 8 | 155 ± 11 | 100% |
| Tr-09 | 171 ± 10 | 129 ± 3 | 113% |
| Null-09 | 178 ± 17 | 149 ± 13 | 100% |

TABLE 23

Photosynthesis (umol carbon dioxide/m2/s), Transpiration (mmol H2O/m2/s) and WUE (Photos/Trans on days 3 and 4 of drought treatment. n = 8

| entry | Photos D3 | Trans. D3 | WUE D3 | Photos. D4 | Trans. D4 | WUE D4 |
|---|---|---|---|---|---|---|
| Tr-05 | 13.4 ± 1.2 | 2.1 ± 0.2 | 6.6 ± 0.2 (116% of null) | 11.6 ± 1.3 | 1.9 ± 0.2 | 6.1 ± 0.4 (104% of null) |
| Null-05 | 14.4 ± 1.1 | 2.5 ± 0.2 | 5.7 ± 0.2 | 12.6 ± 1.2 | 2.2 ± 0.2 | 5.9 ± 0.3 |
| Tr-27 | 14.1 ± 0.7 | 2.4 ± 0.2 | 5.9 ± 0.3 (105% of null) | 11.4 ± 1.6 | 1.9 ± 0.3 | 6.2 ± 0.5 (108% of null) |
| Null-27 | 14.1 ± 1.3 | 2.5 ± 0.1 | 5.6 ± 0.5 | 13.7 ± 1.0 | 2.4 ± 0.1 | 5.7 ± 0.4 |

| SPECIES | SEQ ID NO: | REFERENCE | | |
|---|---|---|---|---|
| ARABIDOPSIS THALIANA | SEQ ID NO: 1 | AtPK220 | NT | 1299 |
| ARABIDOPSIS THALIANA | SEQ ID NO: 2 | AtPK220 | AA | 432 |
| ARABIDOPSIS THALIANA | SEQ ID NO: 3 | AtPK220L292F | NT | 1299 |
| ARABIDOPSIS THALIANA | SEQ ID NO: 4 | AtPK220L292F | AA | 432 |
| ARABIDOPSIS THALIANA | SEQ ID NO: 5 | AtPK220L292F_partial | NT | 1160 |
| ARABIDOPSIS THALIANA | SEQ ID NO: 6 | AtPK220L292F_partial_orf | AA | 383 |
| ARABIDOPSIS THALIANA | SEQ ID NO: 7 | AtPK220_partial | NT | 1160 |
| ARABIDOPSIS THALIANA | SEQ ID NO: 8 | AtPK220_partial_orf | AA | 383 |
| ARABIDOPSIS THALIANA | SEQ ID NO: 9 | AtPK220_with_UTR | NT | 1542 |
| ARABIDOPSIS THALIANA | SEQ ID NO: 10 | AtPK220_for_35s-AtPK220 | NT | 1309 |
| ARABIDOPSIS THALIANA | SEQ ID NO: 11 | AtPK220_partial | NT | 1177 |
| ARABIDOPSIS THALIANA | SEQ ID NO: 12 | At(150)PK | NT | 154 |
| ARABIDOPSIS THALIANA | SEQ ID NO: 13 | At(270)PK | NT | 288 |
| ARABIDOPSIS THALIANA | SEQ ID NO: 14 | AtPK220_promoter | NT | 1510 |
| ARABIDOPSIS THALIANA | SEQ ID NO: 15 | At4g32000_UTR | NT | 157 |
| ARABIDOPSIS THALIANA | SEQ ID NO: 16 | At4g32000 | NT | 1257 |
| ARABIDOPSIS THALIANA | SEQ ID NO: 17 | At4g32000 | AA | 418 |
| ARABIDOPSIS THALIANA | SEQ ID NO: 18 | At5g11020 | NT | 1302 |
| ARABIDOPSIS THALIANA | SEQ ID NO: 19 | At5g11020 | AA | 433 |
| ARABIDOPSIS THALIANA | SEQ ID NO: 20 | At2g25440 | NT | 2016 |
| ARABIDOPSIS THALIANA | SEQ ID NO: 21 | At2g25440 | AA | 671 |
| ARABIDOPSIS THALIANA | SEQ ID NO: 22 | At2g23890 | NT | 1662 |
| ARABIDOPSIS THALIANA | SEQ ID NO: 23 | At2g23890 | AA | 553 |
| BRACHYPODIUM DISTACHYON | SEQ ID NO: 24 | BdPK220 | NT | 1386 |
| BRASSICA NAPUS | SEQ ID NO: 25 | BnPK220 | NT | 1302 |
| BRASSICA NAPUS | SEQ ID NO: 26 | BnPK220 | AA | 433 |
| CICHORIUM ENDIVIA | SEQ ID NO: 27 | EL362007.1 | NT | 657 |
| CICHORIUM ENDIVIA | SEQ ID NO: 28 | EL362007.1_ORF | AA | 218 |
| CITRUS CLEMENTINA | SEQ ID NO: 29 | CX290402.1 | NT | 474 |
| CITRUS CLEMENTINA | SEQ ID NO: 30 | CX290402.1_ORF | AA | 157 |
| CITRUS SINENSIS | SEQ ID NO: 31 | CK934154.1 | NT | 770 |
| CITRUS SINENSIS | SEQ ID NO: 32 | CK934154.1_ORF | AA | 257 |
| COFFEA CANEPHORA | SEQ ID NO: 33 | DV708241.1 | NT | 621 |
| COFFEA CANEPHORA | SEQ ID NO: 34 | DV708241.1_ORF | AA | 206 |
| EUCALYPTUS GUNNII | SEQ ID NO: 35 | CT986101.1 | NT | 411 |
| EUCALYPTUS GUNNII | SEQ ID NO: 36 | CT986101.1_ORF | AA | 136 |
| FESTUCA ARUNDINACEA | SEQ ID NO: 37 | DT714073 | NT | 522 |
| FESTUCA ARUNDINACEA | SEQ ID NO: 38 | DT714073_ORF | AA | 173 |
| GINKGO BILOBA | SEQ ID NO: 39 | EX942240.1 | NT | 740 |
| GINKGO BILOBA | SEQ ID NO: 40 | EX942240.1_ORF | AA | 247 |
| GLYCINE MAX | SEQ ID NO: 41 | GmPK220 | NT | 1254 |
| GLYCINE MAX | SEQ ID NO: 42 | GmPK220 | AA | 418 |
| HELIANTHUS ARGOPHYLLUS | SEQ ID NO: 43 | EE622910.1 | NT | 702 |
| HELIANTHUS ARGOPHYLLUS | SEQ ID NO: 44 | EE622910.1_ORF | AA | 233 |
| HELIANTHUS CILIARIS | SEQ ID NO: 45 | EL429543.1 | NT | 752 |
| HELIANTHUS CILIARIS | SEQ ID NO: 46 | EL429543.1_ORF | AA | 251 |
| HELIANTHUS EXILIS | SEQ ID NO: 47 | EE654885.1 | NT | 630 |
| HELIANTHUS EXILIS | SEQ ID NO: 48 | EE654885.1_ORF | AA | 209 |
| HORDEUM VULGARE | SEQ ID NO: 49 | TC151622 | NT | 780 |
| HORDEUM VULGARE | SEQ ID NO: 50 | TC151622_ORF | AA | 259 |
| IPOMOEA BATATAS | SEQ ID NO: 51 | EE883089.1 | NT | 816 |
| IPOMOEA BATATAS | SEQ ID NO: 52 | EE883089.1_ORF | AA | 272 |

-continued

| SPECIES | SEQ ID NO: | REFERENCE | | |
|---|---|---|---|---|
| LACTUCA SATIVA | SEQ ID NO: 53 | DW125133.1 | NT | 867 |
| LACTUCA SATIVA | SEQ ID NO: 54 | DW125133.1_ORF | AA | 288 |
| MEDICAGO TRUNCATULA | SEQ ID NO: 55 | Contig | NT | 804 |
| MEDICAGO TRUNCATULA | SEQ ID NO: 56 | Contig | AA | 267 |
| NICOTIANA TABACUM | SEQ ID NO: 57 | BP131484.1 | NT | 636 |
| NICOTIANA TABACUM | SEQ ID NO: 58 | BP131484.1 | AA | 211 |
| ORYZA SATIVA | SEQ ID NO: 59 | NM_001061720.1 | NT | 1437 |
| ORYZA SATIVA | SEQ ID NO: 60 | NP_001055185.1 | AA | 478 |
| PHYSCOMITRELLA | SEQ ID NO: 61 | EDQ75046.1_cds | NT | 891 |
| PHYSCOMITRELLA | SEQ ID NO: 62 | EDQ75046.1 | AA | 297 |
| PICEA | SEQ ID NO: 63 | TC12392 | NT | 1065 |
| PICEA | SEQ ID NO: 64 | TC12392_orf | AA | 354 |
| PINUS | SEQ ID NO: 65 | CT578985.1 | NT | 596 |
| PINUS | SEQ ID NO: 66 | CT578985.1_ORF | AA | 199 |
| POPULUS | SEQ ID NO: 67 | TC76879 | NT | 1377 |
| POPULUS | SEQ ID NO: 68 | TC76879_ORF | AA | 459 |
| SACCHARUM OFFICINARUM | SEQ ID NO: 69 | TC46535 | NT | 693 |
| SACCHARUM OFFICINARUM | SEQ ID NO: 70 | TC46535_ORF | AA | 230 |
| TRIPHYSARIA VERSICOLOR | SEQ ID NO: 71 | DR169688.1 | NT | 414 |
| TRIPHYSARIA VERSICOLOR | SEQ ID NO: 72 | DR169688.1_ORF | AA | 137 |
| TRITICUM AESTIVUM | SEQ ID NO: 73 | TC254793 | NT | 1140 |
| TRITICUM AESTIVUM | SEQ ID NO: 74 | TC254793_ORF | AA | 380 |
| VITIS VINIFERA | SEQ ID NO: 75 | CAO44295.1_cds | NT | 978 |
| VITIS VINIFERA | SEQ ID NO: 76 | CAO44295.1 | AA | 325 |
| ZEA MAYS | SEQ ID NO: 77 | TC333547 | NT | 1377 |
| ZEA MAYS | SEQ ID NO: 78 | TC333547_ORF | AA | 458 |
| ZEA MAYS | SEQ ID NO: 79 | ZmPK220 | NT | 1188 |
| ZEA MAYS | SEQ ID NO: 80 | ZmPK220 | AA | 396 |
| GOSSYPIUM | SEQ ID NO: 81 | TC79117 | NT | 1086 |
| GOSSYPIUM | SEQ ID NO: 82 | TC79117_ORF | AA | 361 |
| SOLANUM LYCOPERSICUM | SEQ ID NO: 83 | Contig3 | NT | 1089 |
| AQUILEGIA | SEQ ID NO: 84 | DR918821 | NT | 875 |
| AQUILEGIA | SEQ ID NO: 85 | DR918821_ORF | AA | 292 |
| CENTAUREA MACULOSA | SEQ ID NO: 86 | EL933228.1 | NT | 696 |
| CENTAUREA MACULOSA | SEQ ID NO: 87 | EL933228.1_ORF | AA | 231 |
| CICHORIUM INTYBUS | SEQ ID NO: 88 | EH693146.1 | NT | 842 |
| CICHORIUM INTYBUS | SEQ ID NO: 89 | EH693146.1_ORF | AA | 281 |
| CUCUMIS MELO | SEQ ID NO: 90 | AM742189.1 | NT | 495 |
| CUCUMIS MELO | SEQ ID NO: 91 | AM742189.1_ORF | AA | 164 |
| ERAGROSTIS CURVULA | SEQ ID NO: 92 | EH186232.1 | NT | 375 |
| ERAGROSTIS CURVULA | SEQ ID NO: 93 | EH186232.1_ORF | AA | 124 |
| GERBERA HYBRID | SEQ ID NO: 94 | AJ753651.1 | NT | 414 |
| GERBERA HYBRID | SEQ ID NO: 95 | AJ753651.1_ORF | AA | 137 |
| HELIANTHUS PARADOXUS | SEQ ID NO: 96 | EL488199.1 | NT | 498 |
| HELIANTHUS PARADOXUS | SEQ ID NO: 97 | EL488199.1_ORF | AA | 165 |
| IPOMOEA NIL | SEQ ID NO: 98 | BJ566706.1 | NT | 612 |
| IPOMOEA NIL | SEQ ID NO: 99 | BJ566706.1_ORF | AA | 203 |
| NUPHAR ADVENA | SEQ ID NO: 100 | DT603238.1 | NT | 708 |
| NUPHAR ADVENA | SEQ ID NO: 101 | DT603238.1_ORF | AA | 235 |
| SYNTHETIC PRIMER | SEQ ID NO: 102 | 747F | NT | 30 |
| SYNTHETIC PRIMER | SEQ ID NO: 103 | 747R | NT | 34 |
| SYNTHETIC PRIMER | SEQ ID NO: 104 | C747F2 | NT | 32 |
| SYNTHETIC PRIMER | SEQ ID NO: 105 | C747R2 | NT | 31 |
| SYNTHETIC PRIMER | SEQ ID NO: 106 | A220BamF1 | NT | 42 |
| SYNTHETIC PRIMER | SEQ ID NO: 107 | A220PstR | NT | 40 |
| SYNTHETIC PRIMER | SEQ ID NO: 108 | K188R | NT | 30 |
| SYNTHETIC PRIMER | SEQ ID NO: 109 | A220A1SmaF2 | NT | 53 |
| SYNTHETIC PRIMER | SEQ ID NO: 110 | A220BamR | NT | 38 |
| SYNTHETIC PRIMER | SEQ ID NO: 111 | A220SmaF | NT | 41 |
| SYNTHETIC PRIMER | SEQ ID NO: 112 | A220BamF2 | NT | 41 |
| SYNTHETIC PRIMER | SEQ ID NO: 113 | A220XbaR | NT | 39 |
| SYNTHETIC PRIMER | SEQ ID NO: 114 | K116SacF | NT | 35 |
| SYNTHETIC PRIMER | SEQ ID NO: 115 | K270SacR | NT | 37 |
| SYNTHETIC PRIMER | SEQ ID NO: 116 | K116BamF | NT | 37 |
| SYNTHETIC PRIMER | SEQ ID NO: 117 | K270XbaR | NT | 40 |
| SYNTHETIC PRIMER | SEQ ID NO: 118 | PK81A1XbaF | NT | 52 |
| SYNTHETIC PRIMER | SEQ ID NO: 119 | K81PmBamF | NT | 47 |
| SYNTHETIC PRIMER | SEQ ID NO: 120 | Pm81SmaR2 | NT | 41 |
| ARABIDOPSIS THALIANA | SEQ ID NO: 121 | AtPK220L292F_with_UTR | NT | 1309 |
| SYNTHETIC PRIMER | SEQ ID NO: 122 | Bn81F | NT | 25 |
| SYNTHETIC PRIMER | SEQ ID NO: 123 | Bn81R | NT | 32 |
| SYNTHETIC PRIMER | SEQ ID NO: 124 | Bn81RAF1 | NT | 32 |

-continued

| SPECIES | SEQ ID NO: | REFERENCE | | |
|---|---|---|---|---|
| SYNTHETIC PRIMER | SEQ ID NO: 125 | Bn81RAF2 | NT | 32 |
| SYNTHETIC PRIMER | SEQ ID NO: 126 | Bn81RAR1 | NT | 31 |
| SYNTHETIC PRIMER | SEQ ID NO: 127 | Bn81RAR2 | NT | 37 |
| SYNTHETIC PRIMER | SEQ ID NO: 128 | Bn81F1 | NT | 28 |
| SYNTHETIC PRIMER | SEQ ID NO: 129 | Bn81R1 | NT | 27 |
| SYNTHETIC PRIMER | SEQ ID NO: 130 | Gm81RAR1 | NT | 27 |
| SYNTHETIC PRIMER | SEQ ID NO: 131 | Gm81RAR2 | NT | 29 |
| SYNTHETIC PRIMER | SEQ ID NO: 132 | Cn81RAR1 | NT | 29 |
| SYNTHETIC PRIMER | SEQ ID NO: 133 | Cn81RAR2 | NT | 28 |
| SYNTHETIC PRIMER | SEQ ID NO: 134 | A220SacF | NT | 41 |
| SYNTHETIC PRIMER | SEQ ID NO: 135 | Pm81NheF | NT | 47 |
| SYNTHETIC PRIMER | SEQ ID NO: 136 | Pm81NheR | NT | 43 |
| SYNTHETIC PRIMER | SEQ ID NO: 137 | Gm81RAF1 | NT | 29 |
| SYNTHETIC PRIMER | SEQ ID NO: 138 | Gm81RAF2 | NT | 31 |
| SYNTHETIC PRIMER | SEQ ID NO: 139 | Zm81RAF1 | NT | 31 |
| SYNTHETIC PRIMER | SEQ ID NO: 140 | Zm81RAF2 | NT | 27 |
| SYNTHETIC PRIMER | SEQ ID NO: 141 | MiR319XbaF | NT | 31 |
| SYNTHETIC PRIMER | SEQ ID NO: 142 | MiR319BamR | NT | 33 |
| SYNTHETIC PRIMER | SEQ ID NO: 143 | MiPK220F1 | NT | 40 |
| SYNTHETIC PRIMER | SEQ ID NO: 144 | MiPK220R1 | NT | 35 |
| SYNTHETIC PRIMER | SEQ ID NO: 145 | MiPK220F2 | NT | 35 |
| SYNTHETIC PRIMER | SEQ ID NO: 146 | MiPK220R2 | NT | 42 |
| ARTIFICIAL SEQUENCE | SEQ ID NO: 147 | Synthesized_gene_fragment | NT | 21 |
| ARABIDOPSIS THALIANA | SEQ ID NO: 148 | At4g23713_w_genomic | NT | 399 |
| ARTIFICIAL SEQUENCE | SEQ ID NO: 149 | Artificial_micro_RNA_construct | NT | 399 |
| ARABIDOPSIS THALIANA | SEQ ID NO: 150 | Promoter At2g44790 | NT | 1475 |
| SYNTHETIC PRIMER | SEQ ID NO: 151 | P790-H3-F | NT | 31 |
| SYNTHETIC PRIMER | SEQ ID NO: 152 | P790-Xb-R | NT | 31 |
| BRASSICA NAPUS | SEQ ID NO: 153 | BnPK220 | NT | 338 |
| SYNTHETIC PRIMER | SEQ ID NO: 154 | Bn340BamF | NT | 38 |
| SYNTHETIC PRIMER | SEQ ID NO: 155 | Bn340XbaR | NT | 37 |
| SYNTHETIC PRIMER | SEQ ID NO: 156 | Bn340SacF | NT | 38 |
| SYNTHETIC PRIMER | SEQ ID NO: 157 | Bn340SacR | NT | 37 |
| SYNTHETIC PRIMER | SEQ ID NO: 158 | bWET XbaI F | NT | 24 |
| SYNTHETIC PRIMER | SEQ ID NO: 159 | bWET BamHI R | NT | 28 |
| SYNTHETIC PRIMER | SEQ ID NO: 160 | bWET ClaI R | NT | 28 |
| BRACHYPODIUM DISTACHYON | SEQ ID NO: 161 | BdPK220 | NT | 272 |
| SYNTHETIC PRIMER | SEQ ID NO: 162 | bWx BamHI F | NT | 31 |
| SYNTHETIC PRIMER | SEQ ID NO: 163 | bWx ClaI R | NT | 30 |
| BRACHYPODIUM DISTACHYON | SEQ ID NO: 164 | BdWx intron 1 | NT | 1174 |
| SYNTHETIC PRIMER | SEQ ID NO: 165 | bWET BamHI end2 | NT | 22 |
| SYNTHETIC PRIMER | SEQ ID NO: 166 | BdUBQ PvuI F | NT | 30 |
| SYNTHETIC PRIMER | SEQ ID NO: 167 | BdUBQT PacI R | NT | 28 |
| PANICUM VIRGATUM | SEQ ID NO: 168 | Pv(251)PK220 | NT | 251 |
| SYNTHETIC PRIMER | SEQ ID NO: 169 | PvWET XbaI F | NT | 27 |
| SYNTHETIC PRIMER | SEQ ID NO: 170 | PvWET BamHI R | NT | 27 |
| SYNTHETIC PRIMER | SEQ ID NO: 171 | PvWET ClaI R | NT | 27 |
| SYNTHETIC PRIMER | SEQ ID NO: 172 | PvWET BamHI end1 | NT | 25 |
| SYNTHETIC PRIMER | SEQ ID NO: 173 | PvWET BamHI end2 | NT | 21 |
| SORGHUN BICOLOR | SEQ ID NO: 174 | Sb(261)PK220 | NT | 261 |
| SYNTHETIC PRIMER | SEQ ID NO: 175 | SbWET XbaI F | NT | 26 |
| SYNTHETIC PRIMER | SEQ ID NO: 176 | SbWET BamHI R | NT | 28 |
| SYNTHETIC PRIMER | SEQ ID NO: 177 | SbWET ClaI R | NT | 28 |
| SORGHUN BICOLOR | SEQ ID NO: 178 | SbWx intron 1 | NT | 273 |
| SYNTHETIC PRIMER | SEQ ID NO: 179 | SbWx BamHI | NT | 30 |
| SYNTHETIC PRIMER | SEQ ID NO: 180 | SbWx ClaI R | NT | 34 |
| SYNTHETIC PRIMER | SEQ ID NO: 181 | SbWET BamHI end1 | NT | 24 |
| SYNTHETIC PRIMER | SEQ ID NO: 182 | SbWET BamHI end2 | NT | 21 |
| SORGHUN BICOLOR | SEQ ID NO: 183 | SbGOS2 promoter | NT | 1000 |
| SYNTHETIC PRIMER | SEQ ID NO: 184 | SbGOS2 HindIII F | NT | 28 |
| SYNTHETIC PRIMER | SEQ ID NO: 185 | SbGOS2 HindIII R | NT | 30 |
| SORGHUN BICOLOR | SEQ ID NO: 186 | SbUBQ promoter | NT | 1000 |
| SYNTHETIC PRIMER | SEQ ID NO: 187 | SbUBQ PstI F | NT | 26 |
| SYNTHETIC PRIMER | SEQ ID NO: 188 | SbUBQ PstI R | NT | 28 |
| SORGHUN BICOLOR | SEQ ID NO: 189 | SbUBQ terminator | NT | 239 |
| SYNTHETIC PRIMER | SEQ ID NO: 190 | SbUBQT KpnI F | NT | 27 |
| SYNTHETIC PRIMER | SEQ ID NO: 191 | SbUBQT KpnI R | NT | 27 |
| SYNTHETIC PRIMER | SEQ ID NO: 192 | SbUBQ PvuI F | NT | 34 |
| BRASSICA NAPUS | SEQ ID NO: 193 | BnPK220 | NT | 1302 |
| BRASSICA NAPUS | SEQ ID NO: 194 | BnPK220 | AA | 433 |
| SYNTHETIC PRIMER | SEQ ID NO: 195 | Bd81RAR1 | NT | 31 |
| SYNTHETIC PRIMER | SEQ ID NO: 196 | Bd81RAR2 | NT | 32 |
| BRACHYPODIUM DISTACHYON | SEQ ID NO: 197 | BdPK220 | AA | 461 |
| SYNTHETIC PRIMER | SEQ ID NO: 198 | A200A1AgeF | NT | 53 |

-continued

| SPECIES | SEQ ID NO: | REFERENCE | | |
|---|---|---|---|---|
| SYNTHETIC PRIMER | SEQ ID NO: 199 | A220AgeR | NT | 39 |
| SYNTHETIC PRIMER | SEQ ID NO: 200 | bWET BamHI end1 | NT | 18 |

LITERATURE

1. Altschul S F, Gish W, Miller W, Myers E W, Lipman D J. (1990) Basic local alignment search tool. J. Mol. Biol. 215: 403-410.
2. Altschul S F, Madden T L, Schäffer A A, Zhang J, Zhang Z, Miller W, Lipman D J. (1997) Gapped BLAST and PSI-BLAST: a new generation of protein database search programs. Nucl. Acid Res. 25: 3389-3402.
3. An G, Mitra A, Choi H K, Costa M A, An K, Thornburg R W, Ryan C A. (1989) Functional analysis of the 3' control region of the potato wound-inducible proteinase inhibitor II gene. Plant Cell 1: 115-122.
4. Araus L J, Slafer G A, Reynolds M P, Royo C (2002) Plant Breeding and drought in C3 cereals: What should we breed for? *Annals of Botany* 89: 925-940.
5. Atanassvoa R, Chaubet N, Gigot C (1992) A 126 bp fragment of a plant histone gene promoter confers preferential expression in meristems of transgenic *Arabidopsis*. Plant Journal 2(3): 291-300.
6. Beetham P R, Kipp P B, Sawycky X L, Arntzen C J, May G D (1999) A tool for functional plant genomics: chimeric RNA/DNA oligonucleotides cause in vivo gene-specific mutations. Proceedings of the National Academy of Science USA, 96: 8774-8778.
7. Bevan M, Barnes W M, Chilton M D (1983) Structure and transcription of the nopaline synthase gene region of T-DNA. Nucl. Acids Res. 12: 369-385.
8. Bevan M, Barker R, Goldsbrough A, Jarvis M, Kavanagh T, Iturriaga G. (1986) The structure and transcription start site of a major potato tuber protein gene. Nucleic Acids Research 14: 4625-4636.
9. Christensen A H, Sharrock R A, Quail P H. (1992) Maize polyubiquitin genes: structure, thermal perturbation of expression and transcript splicing, and promoter activity following transfer to protoplasts by electroporation. Plant Mol. Biol. 18: 675-689.
10. Condon A G, Richards R A, Rebetzke G J, Farquhar G D (2002) Improving Intrinsic Water-Use Efficiency and crop yield. *Crop Science* 42:122-131.
11. Davies W J, Wilkinson S, Loveys B R (2002) Stomatal control by chemical signalling and the exploitation of this mechanism to increase water use efficiency in agriculture. New Phytol. 153: 449-460.
12. De Loose M, Gheysen G, Tire C, Gielen J, Villarroel R, Genetello C, Van Montagu M, Depicker A, Inzé D (1991) The extensin signal peptide allows secretion of a heterologous protein from protoplasts. Gene 99: 95-100.
13. Dong C, Beetham P, Vincent K, Sharp P (2006) Oligonucleotide-directed gene repair in wheat using a transient plasmid gene repair assay system. Plant Cell Reports 25: 457-465.
14. Dratewka-Kos E, Rahman S, Grzelczak Z F, Kennedy T D, Murray R K, Lane B G (1989) Polypeptide structure of germin as deduced from cDNA sequencing. J. Biol. Chem. 264: 4896-4900.
15. Elomaa P, Mehto M, Kotilainen M, Helariutta Y, Nevalainen L, Teeri T H (1998) A bHLH transcription factor mediates organ, region and flower type specific signals on dihydroflavonol-4-reductase (dfr) gene expression in the inflorescence of Gerbera hybrida (Asteraceae). The Plant Journal 16(1): 93-99.
16. Farquhar G D and Sharky T D (1994) Photosynthesis and carbon assimilation (p187) in Physiology and Determination of Crop Yield, ASA, CSSA, SSSA, Madison Wisconsin USA.
17. Fraley R T, Rogers S G, Horsch R B, Sanders P R, Flick J S, Adams S P, Bittner M L, Brand L A, Fink C L, Fry J S, Galluppi G R, Goldberg S B, Hoffmann N L, Woo S C (1983) Expression of bacterial genes in plant cells. Proc Natl Acad Sci USA. 80(15): 4803-4807.
18. Goeddel, GENE EXPRESSION TECHNOLOGY: METHODS IN ENZYMOLOGY 185, Academic Press, San Diego, Calif. (1990).
19. Goldberg R B (1986) Regulation of plant gene expression. Philos Trans R Soc London Ser B 314: 343-353.
20. Greene E A, Codomo C A, Taylor N E, Henikoff J G, Till B J, Reynolds S H, Enns L C, Burtner C, Johnson J E, Odden A R, Comai L, Henikoff S (2003) Spectrum of chemically induced mutations from a large-scale reverse-genetic screen in *Arabidopsis*. Genetics 164(2):731-740.
21. Gruber et al. "Vectors for Plant Transformation" in Methods in Plant Molecular Biology and Biotechnology, Glick B. R. and Thompson, J. E. Eds. (CRC Press, Inc., Boca Raton, 1993) pages 89-119.
22. Hardie D G (1999) PLANT PROTEIN SERINE/THREONINE KINASES: Classification and Functions. Annu Rev Plant Physiol Plant Mol Biol. 50:97-131.
23. Henikoff S, and Henikoff J G (1992) Amino acid substitution matrices from protein blocks. Proc. Natl. Acad. Sci. USA 89: 10915-10919.
24. Horsch R, Fry J E, Hoffmann N, Eichholtz D, Rogers S, Fraley R T (1985) A simple and general method for transferring genes into plants. Science 227:1229-1231.
25. Huang Y, Li H, Gupta R, Morris P C, Luan S, Kieber J J. (2000) ATMPK4, an *Arabidopsis* homolog of mitogen-activated protein kinase, is activated in vitro by AtMEK1 through threonine phosphorylation. Plant Physiol. 122(4): 1301-1310.
26. Kado C I, Hooykaas P J (1991) Molecular mechanisms of crown gall tumorigenesis. Crit. Rev. Plant Sci. 10: 1-32.
27. Karaba A, Dixit S, Greco R, Aharoni A, Trijatmiko K R, Marsch-Martinez N, Krishnan A, Nataraja K N, Udayakumar M, Pereira A (2007) Improvement of water use efficiency in rice by expression of HARDY, an *Arabidopsis* drought and salt tolerant gene. Proc. Natl. Acad. Sci. USA 104: 15270-15272.
28. Keil M, Sanchez-Serrano J, Schell J, Willmitzer L (1986) Primary structure of a proteinase inhibitor II gene from potato (*Solanum tuberosum*). Nucl. Acids Res. 14: 5641-5650.
29. Laemmli, UK (1970) Cleavage of structural proteins during the assembly of the head of bacteriophage T4. Nature. 227(259): 680-685.
30. Last D I, Brettell R I, Chamberlain D A, Chaudhury A M, Larkin P J, Marsh E L, Peacock W J, Dennis E S (1991) pEmu: an improved promoter for gene expression in cereal cells Theor. Appl. Genet. 81: 581-588.
31. Lepetit M, Ehling M, Chaubet N, Gigot C (1992) A plant histone gene promoter can direct both replication-dependent and -independent gene expression in transgenic plants. Mol. Gen. Genet., 231: 276-285.
32. Lund P, Dunsmuir P (1992) A plant signal sequence enhances the secretion of bacterial ChiA in transgenic tobacco. Plant Mol. Biol. 18: 47-53.
33. McElroy D, Zhang W, Cao J, Wu R (1990) Isolation of an efficient actin promoter for use in rice transformation. Plant Cell 2(2): 163-171.
34. Mian M A R, Bailey M A, Ashley D A, Wells R, Carter T E Jr, Parrott W A, Boerma H R (1996) Molecular markers associated with water use efficiency and leaf ash in soybean. Crop Sci. 36: 1252-1257.
35. Martin B, Nienhuis J, King G, Schaefer A (1989) Restriction Fragment Length Polymorphisms Associated with Water Use Efficiency in Tomato. Science. 243(4899): 1725-1728.
36. Masle J, Gilmore S R, Farquhar G D (2005) The ERECTA gene regulates plant transpiration efficiency in Arabidopsis. Nature 436: 866-870
37. Matsuoka K, Nakamura K (1991) Propeptide of a precursor to a plant vacuolar protein required for vacuolar targeting. Proc. Nat'l Acad. Sci. USA 88: 834-838.
38. van der Meer I M, Spelt C E, Mol J N, Stuitje A R (1990) Promoter analysis of the chalcone synthase (chsA) gene of Petunia hybrida: a 67 bp promoter region directs flower-specific expression. Plant Molecular Biology 15(1): 95-109.
39. Mogen B D, MacDonald M H, Graybosch R, Hunt A G (1990) Upstream sequences other than AAUAAA are required for efficient messenger RNA 3'-end formation in plants. Plant Cell 2: 1261-1272.
40. Moloney M M, Walker J M, Sharma K K (1989) High efficiency transformation of Brassica napus using Agrobacterium vectors. Plant Cell Reports 8: 238-242.
41. Needleman S B, Wunsch C D (1970) A general method applicable to the search for similarities in the amino acid sequence of two proteins. J. Mol. Biol. 48: 443-453.
42. Odell J T, Nagy F, Chua N H (1985) Identification of DNA sequences required for activity of the cauliflower mosaic virus 35S promoter. Nature 313: 810-812.
43. Oleykowski C A, Bronson Mullins C R, Godwin A K, Yeung A T (1998) Mutation detection using a novel plant endonuclease. Nucleic Acids Res. 26(20): 4597-4602.
44. Sanford J C, Smith F D, Russell J A (1993) Optimizing the biolistic process for different biological applications. Methods Enzymol. 217: 483-509.
45. Klein T M, Arentzen R, Lewis P A, Fitzpatrick-McElligott S (1992) Transformation of microbes, plants and animals by particle bombardment. Biotechnology 10: 286-291.
46. Sambrook J, Fritsch E F, Maniatis T (1989) Molecular Cloning. A Laboratory Manual, 2$^{nd}$ Ed., Cold Spring Harbor Laboratory Press, New York
47. Sinclair T R (1994) Limits to crop yield. in Physiology and Determination of Crop Yield, ASA, CSSA, SSSA, Madison Wisconsin USA.
48. Price A H, Cairns J E, Horton P, Jones H G, Griffiths H (2002) Linking drought-resistance mechanisms to drought avoidance in upland rice using a QTL approach: progress and new opportunities to integrate stomatal and mesophyll responses. Journal of Experimental Botany 53: 989-1004.
49. Schwab R, Ossowski S, Riester M, Warthmann N, Weigel D (2006) Highly specific gene silencing by artificial microRNAs in Arabidopsis. Plant Cell 18(5): 1121-1133.
50. Shiu S H, Bleecker A B (2001) Receptor-like kinases from Arabidopsis form a monophyletic gene family related to animal receptor kinases. Proc Natl Acad Sci USA. 98(19): 10763-10768.
51. Stockinger E J, Mulinix C A, Long C M, Brettin T S, Iezzoni A F (1996) A linkage map of sweet cherry based on RAPD analysis of a microspore-derived callus culture population. J. Heredity 87: 214-218.
52. Thumma B R, Naidu B P, Chandra A, Cameron D F, Bahnisch L M, Liu C (2001) Identification of causal relationship among traits related to drought resistance in Stylosanthes scabra using QTL analysis. Journal of Experimental Botany 52: 203-214.
53. Torii K U, Mitsukawa N, Oosumi T, Matsuura Y, Yokoyama R, Whittier R F, Komeda Y (1996) The Arabidopsis ERECTA gene encodes a putative receptor protein kinase with extracellular leucine-rich repeats. Plant Cell. 8(4): 735-746.
54. Velten J, Velten L, Hain R, Schell J (1984) Isolation of a dual plant promoter fragment from the Ti plasmid of Agrobacterium tumefaciens. EMBO J. 3: 2723-2730.
55. Verwoert I I, Linden K H, Nijkamp H J, Stuitje A R (1994) Developmental specific expression and organelle targeting of the Escherichia coli fabD gene, encoding malonyl coenzyme A-acyl carrier protein transacylase in transgenic rape and tobacco seeds. Plant Mol. Biol. 26: 189-202.
56. Visser R G, Stolte A, Jacobsen E (1991) Expression of a chimaeric granule-bound starch synthase-GUS gene in transgenic potato plants. Plant Molecular Biology 17: 691-699.
57. Walling L L, Chang Y C, Demmin D S, Holzer F M (1988) Isolation, characterization and evolutionary relatedness of three members from the soybean multigene family encoding chlorophyll a/b binding proteins. Nucl. Acids Res. 16: 10477-10492.
58. Weissbach A and Weissbach H Eds. (1988) Methods for plant molecular biology. Academic Press (San Diego).
59. Wilkins T A, Bednarek S Y, Raikhel N V (1990) Role of propeptide glycan in post-translational processing and transport of barley lectin to vacuoles in transgenic tobacco. Plant Cell 2: 301-313.
60. Yang B, Wen X, Kodali N S, Oleykowski C A, Miller C G, Kulinski J, Besack D, Yeung J A, Kowalski D, Yeung A T (2000) Purification, cloning, and characterization of the CEL I nuclease. Biochemistry. 39(13): 3533-3541.

We claim:

1. A recombinant DNA construct comprising a polynucleotide sequence and a terminator sequence comprising the sequence set forth in SEQ ID NO: 189, wherein said terminator sequence functions as a transcriptional terminator in a plant cell, and wherein said polynucleotide sequence is heterologous to said terminator sequence.

2. A plant comprising the recombinant DNA construct of claim 1.

3. The plant of claim 2 wherein the plant is a monocot.

4. The plant of claim 2 wherein the plant is a maize plant.

5. A seed comprising the recombinant DNA construct of claim 1.

6. The seed of claim 5 wherein the seed is from a monocot plant.

7. The seed of claim 5 wherein the seed is from a maize plant.

8. A method of expressing a polynucleotide sequence in a plant, comprising the steps of:
   (a) introducing into a regenerable plant cell the recombinant DNA construct of claim 1, wherein said polynucleotide sequence is heterologous to said terminator sequence;
   (b) regenerating a transgenic plant from the regenerable plant cell of step (a), wherein the transgenic plant comprises the recombinant DNA construct of claim 5; and
   (c) obtaining a progeny plant or seed from the transgenic plant of step (b), wherein the progeny plant or seed comprises the recombinant DNA construct of claim 5 and exhibits expression of the heterologous polynucleotide.

9. The method of claim 8, wherein the plant is a monocot plant.

10. The method of claim 8, wherein the plant is a maize plant.

11. A transgenic seed produced by the method of claim 8.

* * * * *

UNITED STATES PATENT AND TRADEMARK OFFICE
CERTIFICATE OF CORRECTION

| | | |
|---|---|---|
| PATENT NO. | : 11,913,008 B2 | Page 1 of 1 |
| APPLICATION NO. | : 18/048002 | |
| DATED | : February 27, 2024 | |
| INVENTOR(S) | : Jiangxin Wan et al. | |

It is certified that error appears in the above-identified patent and that said Letters Patent is hereby corrected as shown below:

In the Claims

At Column 120, Claim number 8:
"(b) regenerating a transgenic plant from the regenerable plant cell of step (a), wherein the transgenic plant comprises the recombinant DNA construct of claim 5; and
(c) obtaining a progeny plant or seed from the transgenic plant of step (b), wherein the progeny plant or seed comprises the recombinant DNA construct of claim 5 and exhibits expression of the heterologous polynecleotide."

Should read:
--(b) regenerating a transgenic plant from the regenerable plant cell of step (a), wherein the transgenic plant comprises the recombinant DNA construct of claim 1; and
(c) obtaining a progeny plant or seed from the transgenic plant of step (b), wherein the progeny plant or seed comprises the recombinant DNA construct of claim 1 and exhibits expression of the heterologous polynecleotide.--

Signed and Sealed this
Seventeenth Day of September, 2024

Katherine Kelly Vidal
*Director of the United States Patent and Trademark Office*